United States Patent
Williams

(10) Patent No.: US 12,226,239 B2
(45) Date of Patent: Feb. 18, 2025

(54) SYSTEMS, DEVICES, AND METHODS FOR APPLICATIONS FOR COMMUNICATION WITH KETONE SENSORS

(71) Applicant: LINGO SENSING TECHNOLOGY UNLIMITED COMPANY, Dublin (IE)

(72) Inventor: Justin N. Williams, Oakland, CA (US)

(73) Assignee: LINGO SENSING TECHNOLOGY UNLIMITED COMPANY, Dublin (IE)

( * ) Notice: Subject to any disclaimer, the term of this patent is extended or adjusted under 35 U.S.C. 154(b) by 0 days.

(21) Appl. No.: 17/944,670

(22) Filed: Sep. 14, 2022

(65) Prior Publication Data

US 2023/0128193 A1    Apr. 27, 2023

Related U.S. Application Data

(60) Provisional application No. 63/405,666, filed on Sep. 12, 2022, provisional application No. 63/337,442, (Continued)

(51) Int. Cl.
G06F 3/04842    (2022.01)
A61B 5/00    (2006.01)
(Continued)

(52) U.S. Cl.
CPC .......... *A61B 5/743* (2013.01); *A61B 5/14546* (2013.01); *A61B 5/7435* (2013.01);
(Continued)

(58) Field of Classification Search
CPC ... A61B 5/743; A61B 5/7435; G06F 3/04817; G06F 3/04842
See application file for complete search history.

(56) References Cited

U.S. PATENT DOCUMENTS

| | | |
|---|---|---|
| 6,585,516 B1 | 7/2003 | Alabaster |
| 7,399,277 B2 | 7/2008 | Saidara et al. |

(Continued)

FOREIGN PATENT DOCUMENTS

| | | |
|---|---|---|
| WO | WO 2009/146445 A1 | 12/2009 |
| WO | WO 2015/153482 A1 | 10/2015 |
| WO | WO 2016/179559 A2 | 11/2016 |

OTHER PUBLICATIONS

EP, 13859365.2 Extended Search Report, Jul. 5, 2016.
(Continued)

*Primary Examiner* — William L Bashore
*Assistant Examiner* — Gregory A Distefano
(74) *Attorney, Agent, or Firm* — ONE LLP

(57) ABSTRACT

A software library for providing a uniform framework for various applications or third-party applications access to sensor data. The system further includes a sensor control module and a remote management module. The sensor control module includes logic for communicating with the sensors and receiving sensor data and to communicate that sensor data to the remote management module or various applications. The sensor control module may include a user interface that may display a banner containing numerous components. The content of the banner may differ depending on the host application. The system may further include a host application that incorporates the banner.

24 Claims, 50 Drawing Sheets

Related U.S. Application Data filed on May 2, 2022, provisional application No. 63/295,275, filed on Dec. 30, 2021, provisional application No. 63/276,396, filed on Nov. 5, 2021, provisional application No. 63/244,694, filed on Sep. 15, 2021.

(51) Int. Cl.
*A61B 5/145* (2006.01)
*G06F 3/04817* (2022.01)

(52) U.S. Cl.
CPC ........ *A61B 5/7475* (2013.01); *G06F 3/04817* (2013.01); *G06F 3/04842* (2013.01)

(56) References Cited

U.S. PATENT DOCUMENTS

| | | | |
|---|---|---|---|
| 7,684,872 B2 | 3/2010 | Carney et al. | |
| 8,478,406 B2 | 7/2013 | Burnes et al. | |
| 8,821,792 B2 | 9/2014 | Drucker et al. | |
| 9,143,569 B2 | 9/2015 | Mensinger et al. | |
| 9,215,980 B2 | 12/2015 | Tran et al. | |
| 9,299,238 B1* | 3/2016 | Ahmad | H04W 4/80 |
| 9,339,197 B2 | 5/2016 | Griswold et al. | |
| 9,351,684 B1* | 5/2016 | Ahmad | A61B 5/7475 |
| 9,414,775 B2 | 8/2016 | Colvin, Jr. et al. | |
| 9,446,194 B2 | 9/2016 | Kamath et al. | |
| 9,452,258 B2 | 9/2016 | Dobbles et al. | |
| 9,717,421 B2 | 8/2017 | Griswold et al. | |
| 9,814,400 B1 | 11/2017 | Cendrillon et al. | |
| 10,159,432 B1 | 12/2018 | Pathak et al. | |
| 10,209,817 B1 | 2/2019 | Cazzoli et al. | |
| 10,264,971 B1 | 4/2019 | Kennedy et al. | |
| 11,056,223 B1* | 7/2021 | Ahmad | A61B 5/6898 |
| 11,091,788 B2 | 8/2021 | Ouyang et al. | |
| 2002/0013339 A1 | 1/2002 | Martin et al. | |
| 2003/0208113 A1 | 11/2003 | Mault et al. | |
| 2004/0158294 A1 | 8/2004 | Thompson | |
| 2005/0038680 A1 | 2/2005 | McMahon | |
| 2005/0075675 A1 | 4/2005 | Mulligan et al. | |
| 2006/0016700 A1 | 1/2006 | Brister et al. | |
| 2006/0019397 A1 | 1/2006 | Soykan | |
| 2006/0270421 A1 | 11/2006 | Phillips et al. | |
| 2007/0015976 A1 | 1/2007 | Miesel et al. | |
| 2007/0255166 A1 | 11/2007 | Carney et al. | |
| 2007/0255352 A1 | 11/2007 | Roline et al. | |
| 2007/0255353 A1 | 11/2007 | Reinke et al. | |
| 2007/0265666 A1 | 11/2007 | Roberts et al. | |
| 2007/0265668 A1 | 11/2007 | Reinke et al. | |
| 2007/0265671 A1 | 11/2007 | Roberts et al. | |
| 2007/0265674 A1 | 11/2007 | Olson et al. | |
| 2008/0125701 A1 | 5/2008 | Moberg et al. | |
| 2009/0147011 A1* | 6/2009 | Buck | G06F 9/451 |
| | | | 345/501 |
| 2009/0192366 A1 | 7/2009 | Mensinger et al. | |
| 2009/0192745 A1 | 7/2009 | Kamath et al. | |
| 2009/0240120 A1 | 9/2009 | Mensinger et al. | |
| 2009/0240128 A1 | 9/2009 | Mensinger et al. | |
| 2009/0240193 A1 | 9/2009 | Mensinger et al. | |
| 2010/0023081 A1 | 1/2010 | Audet et al. | |
| 2010/0274515 A1 | 10/2010 | Hoss et al. | |
| 2011/0124996 A1 | 5/2011 | Reinke et al. | |
| 2011/0287528 A1* | 11/2011 | Fern | G16H 40/67 |
| | | | 435/287.1 |
| 2012/0172690 A1 | 7/2012 | Anderson et al. | |
| 2012/0172891 A1 | 7/2012 | Lee | |
| 2012/0172892 A1 | 7/2012 | Grubac et al. | |
| 2012/0262298 A1 | 10/2012 | Bohm et al. | |
| 2012/0323099 A1 | 12/2012 | Mothilal et al. | |
| 2013/0043974 A1 | 2/2013 | Hyde et al. | |
| 2013/0085358 A1 | 4/2013 | Crouther et al. | |
| 2013/0132330 A1 | 5/2013 | Hurwitz et al. | |
| 2013/0198685 A1 | 8/2013 | Bernini et al. | |
| 2013/0253309 A1 | 9/2013 | Allan et al. | |
| 2013/0253342 A1 | 9/2013 | Griswold et al. | |
| 2013/0253343 A1 | 9/2013 | Waldhauser et al. | |
| 2013/0253345 A1 | 9/2013 | Griswold et al. | |
| 2013/0253346 A1 | 9/2013 | Griswold et al. | |
| 2013/0253347 A1 | 9/2013 | Griswold et al. | |
| 2014/0001044 A1 | 1/2014 | Ecoff et al. | |
| 2014/0005499 A1 | 1/2014 | Catt et al. | |
| 2014/0039383 A1 | 2/2014 | Dobbles et al. | |
| 2014/0052091 A1 | 2/2014 | Dobbles et al. | |
| 2014/0052092 A1 | 2/2014 | Dobbles et al. | |
| 2014/0058240 A1 | 2/2014 | Mothilal et al. | |
| 2014/0088393 A1 | 3/2014 | Bernstein et al. | |
| 2014/0095081 A1 | 4/2014 | Doniger et al. | |
| 2014/0278189 A1 | 9/2014 | Vanslyke et al. | |
| 2014/0350105 A1 | 11/2014 | D'Agostino et al. | |
| 2014/0350359 A1 | 11/2014 | Tankiewicz et al. | |
| 2014/0350369 A1 | 11/2014 | Budiman et al. | |
| 2015/0118658 A1 | 4/2015 | Mayou et al. | |
| 2015/0119655 A1 | 4/2015 | Mayou et al. | |
| 2015/0120317 A1 | 4/2015 | Mayou et al. | |
| 2015/0126881 A1* | 5/2015 | Ogiue | G16H 20/30 |
| | | | 600/502 |
| 2015/0141770 A1 | 5/2015 | Rastogi et al. | |
| 2015/0173648 A1 | 6/2015 | Sano et al. | |
| 2015/0170504 A1 | 7/2015 | Jooste | |
| 2015/0212096 A1 | 7/2015 | Kodama et al. | |
| 2015/0289821 A1 | 10/2015 | Rack-Gomer et al. | |
| 2015/0292856 A1 | 10/2015 | Ganton et al. | |
| 2016/0077037 A1* | 3/2016 | Cha | G01N 27/3274 |
| | | | 205/777.5 |
| 2016/0100807 A1 | 4/2016 | Johnson et al. | |
| 2016/0101232 A1 | 4/2016 | Kamath et al. | |
| 2016/0103604 A1 | 4/2016 | Johnson et al. | |
| 2016/0166195 A1* | 6/2016 | Radecka | A61B 5/112 |
| | | | 600/595 |
| 2016/0232322 A1 | 8/2016 | Mensinger et al. | |
| 2016/0262670 A1 | 9/2016 | Wasson et al. | |
| 2016/0321428 A1 | 11/2016 | Rogers | |
| 2016/0324463 A1 | 11/2016 | Simpson et al. | |
| 2016/0328990 A1 | 11/2016 | Simpson et al. | |
| 2016/0328991 A1 | 11/2016 | Simpson et al. | |
| 2016/0331310 A1 | 11/2016 | Kovatchev | |
| 2016/0345830 A1 | 12/2016 | Raisoni et al. | |
| 2017/0027515 A1 | 2/2017 | Wiser | |
| 2017/0157774 A1 | 6/2017 | Pathak et al. | |
| 2017/0169358 A1 | 6/2017 | Choi et al. | |
| 2017/0172510 A1 | 6/2017 | Homyk et al. | |
| 2017/0185748 A1 | 6/2017 | Budiman et al. | |
| 2017/0213145 A1 | 7/2017 | Pathak et al. | |
| 2017/0215808 A1 | 8/2017 | Shimol et al. | |
| 2017/0311903 A1 | 11/2017 | Davis et al. | |
| 2018/0039097 A1 | 2/2018 | Gutierrez | |
| 2018/0042558 A1* | 2/2018 | Cabrera, Jr. | G06F 17/18 |
| 2018/0052976 A1 | 2/2018 | Lee et al. | |
| 2018/0103882 A1 | 4/2018 | Biederman et al. | |
| 2018/0110078 A1 | 4/2018 | Mandapaka et al. | |
| 2018/0125364 A1 | 5/2018 | DeHennis | |
| 2018/0137252 A1* | 5/2018 | Mairs | G16H 40/63 |
| 2018/0256103 A1* | 9/2018 | Cole | A61B 5/14546 |
| 2018/0279928 A1 | 10/2018 | Bohm et al. | |
| 2019/0075443 A1 | 3/2019 | Fu et al. | |
| 2019/0275234 A1 | 9/2019 | Yang | |
| 2019/0307958 A1 | 10/2019 | Yang | |
| 2019/0328340 A1 | 10/2019 | Yang | |
| 2020/0237275 A1 | 7/2020 | Feldman et al. | |
| 2020/0237276 A1 | 7/2020 | Oja et al. | |
| 2020/0275893 A1 | 9/2020 | Burnette et al. | |
| 2021/0000415 A1 | 1/2021 | Cole et al. | |
| 2021/0000416 A1 | 1/2021 | Cole et al. | |
| 2021/0007664 A1 | 1/2021 | Cole et al. | |
| 2021/0007665 A1 | 1/2021 | Cole et al. | |
| 2021/0219885 A1 | 7/2021 | Wang et al. | |
| 2021/0369155 A1 | 12/2021 | Feldman et al. | |

(56) References Cited

U.S. PATENT DOCUMENTS

2022/0084100 A1* 3/2022 Payne ................ G16H 20/60
2022/0186278 A1   6/2022 Liu et al.

OTHER PUBLICATIONS

EP, 18712038.1 Examination Report, Oct. 12, 2020.
WO, PCT/US2018/020030 Isr and Written Opinion, May 9, 2018.
Teller, A., "A platform for wearable physiological computing", Interacting with Computers, 2004, vol. 16, pp. 917-937.
Williamson, J., et al., "Data Sensing and Analysis: Challenges for Wearables", The $20^{th}$ Asia and South Pacific Design Automation Conference, IEEE, 2015, pp. 136-141.

* cited by examiner

SYSTEMS, DEVICES, AND METHODS FOR APPLICATIONS FOR COMMUNICATION WITH KETONE SENSORS

CROSS-REFERENCE TO RELATED APPLICATIONS

This application claims priority to U.S. Provisional Application No. 63/405,666, filed Sep. 12, 2022, U.S. Provisional Application No. 63/337,442, filed May 2, 2022, U.S. Provisional Application No. 63/295,275, filed Dec. 30, 2021, U.S. Provisional Application Ser. No. 63/276,396, filed Nov. 5, 2021, and U.S. Provisional Application No. 63/244,694, filed Sep. 15, 2021, all of which are herein expressly incorporated by reference in their entireties for all purposes.

FIELD

The subject matter described herein relates generally to digital interfaces and user interfaces for analyte monitoring systems, as well as systems, methods, and devices relating thereto.

BACKGROUND

The detection and/or monitoring of analyte levels, such as glucose, ketones, ketone bodies (e.g., β-hydroxybutyrate), lactate, oxygen, hemoglobin A1C, or the like, can be vitally important to the overall health of a person, particularly for an individual having diabetes. Patients suffering from diabetes mellitus can experience complications including loss of consciousness, cardiovascular disease, retinopathy, neuropathy, and nephropathy. Persons with diabetes are generally required to monitor their glucose levels to ensure that they are being maintained within a clinically safe range, and may also use this information to determine if and/or when insulin is needed to reduce glucose levels in their bodies, or when additional glucose is needed to raise the level of glucose in their bodies.

Growing clinical data demonstrates a strong correlation between the frequency of glucose monitoring and glycemic control. Despite such correlation, however, many individuals diagnosed with a diabetic condition do not monitor their glucose levels as frequently as they should due to a combination of factors including convenience, testing discretion, pain associated with glucose testing, and cost.

To increase patient adherence to a plan of frequent glucose monitoring, in vivo analyte monitoring systems can be utilized, in which a sensor control device may be worn on the body of an individual who requires analyte monitoring. To increase comfort and convenience for the individual, the sensor control device may have a small form-factor and can be applied by the individual with a sensor applicator. The application process includes inserting at least a portion of a sensor that senses a user's analyte level in a bodily fluid located in a layer of the human body, using an applicator or insertion mechanism, such that the sensor comes into contact with the bodily fluid. The analyte monitoring system may also be configured to transmit analyte data and/or alarms to another device, from which a caregiver such as, for example, a parent, a spouse, or a health care provider ("HCP"), can review the data and make therapy decisions. Furthermore, the benefits of analyte monitoring systems are not limited to persons with diabetes. For instance, analyte monitoring systems can provide useful information and insights to individuals interested in improving their health and wellness. As one example, to improve their sports performance, athletes can utilize a sensor control device worn on the body to collect data relating to one or more analytes such as, for example, glucose and/or lactate. Other non-medical applications for analyte monitoring systems are possible and described in further detail below.

Despite their advantages, however, some people are reluctant to use analyte monitoring systems for various reasons, including the complexity and volume of data presented, a learning curve associated with the software and user interfaces for analyte monitoring systems, and an overall paucity of actionable information presented.

Furthermore, as sensor control devices have become more convenient, comfortable, and affordable for users, applications outside of medicine have become feasible. For example, high-performance athletes are interested in optimizing levels of performance-affecting analytes, for example blood glucose, before or during training and competition. However, some existing user interfaces for sensor control devices are designed for medical use by patients under care of a physician, and not for non-medical applications such as, for example, athletic training and competition. As such, the data collected by the sensor control device, and methods for presenting the data to the user, may be unsuitable for non-medical applications. In addition, sensor control devices for non-medical (e.g., wellness and fitness) use may be confused with similar devices made for medical use, leading to problems in interpreting or using data.

Various applications make use of the sensor data to perform various functions, including wellness functions. However, each software that desires to use the sensor data may become subject to regulatory standards or require regulatory clearance and be viewed as software as a medical device. Any new application desiring to make a use-case for the physiological data that can be obtained from sensors may face regulatory hurdles under the Food and Drug Administration. Thus, there exists a need to provide a framework that can communicate with physiological sensors and receive analyte data for use by various applications, including third party applications, but avoids the need for regulatory approval for every use-case for the data. Moreover, a need exists for digital interfaces and graphical user interfaces for analyte monitoring systems for medical and/or non-medical use, as well as methods and devices relating thereto, that are robust, user-friendly, and provide for timely and actionable responses.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to a software library for use by applications to obtain sensor data. The software library can include a sensor control module, a remote management module, and include software logic for communication with a plurality of physiological sensors and applications. The sensor control module can authenticate the receiving device to allow the receiving device to receive sensor data, including by enabling communication with each of the plurality of physiological sensors to receive sensor data including data indicative of a different physiological signal. The sensor control module can further store the sensor data in a memory of the computing device. The sensor control module can obtain an output indicative of the different physiological signals from the sensor data of each of the plurality of physiological sensors. The sensor control module can provide the output of the different physiological signals from the physiological sensors to the authenticated third-party application running on the computing device.

In accordance with the disclosed subject matter, the physiological sensors can comprise an analyte sensor configured to detect an analyte level in a bodily fluid of a user. The output of the different physiological signals can also comprise an analyte value. The output can further comprise a notification of a physiological condition. The output can further indicate information about delivery of a medicament to a user.

In accordance with the disclosed subject matter, the communication session within the computing device and between the computing device and the physiological sensors can comprise a near-field communication (NFC), BLUETOOTH® low energy (BLE), or any suitable wireless communication protocol known in the art.

The software library can further include a remote data management module including instructions to transmit sensor data to a remote server over a network. The remote management module can be configured to communicate with the remote server to authenticate the sensor control module, third-party application, or any other application. The authentication can use a uniform user interface irrespective of the application accessing the software library.

In accordance with the disclosed subject matter, the plurality of physiological sensors and the software library are subject to regulatory approval, including as software as a medical device. The output indicative of the physiological signal from the physiological sensors is also subject to regulatory approval. However, the third-party application running on the computing device is not subject to regulatory approval.

The software library can be configured to be implemented as a component of the authenticated third-party application. Because of the modular architecture and shared functionality, sensor data can be substantially simultaneously received, interpreted, and displayed from a plurality of physiological sensors.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Figure 1:
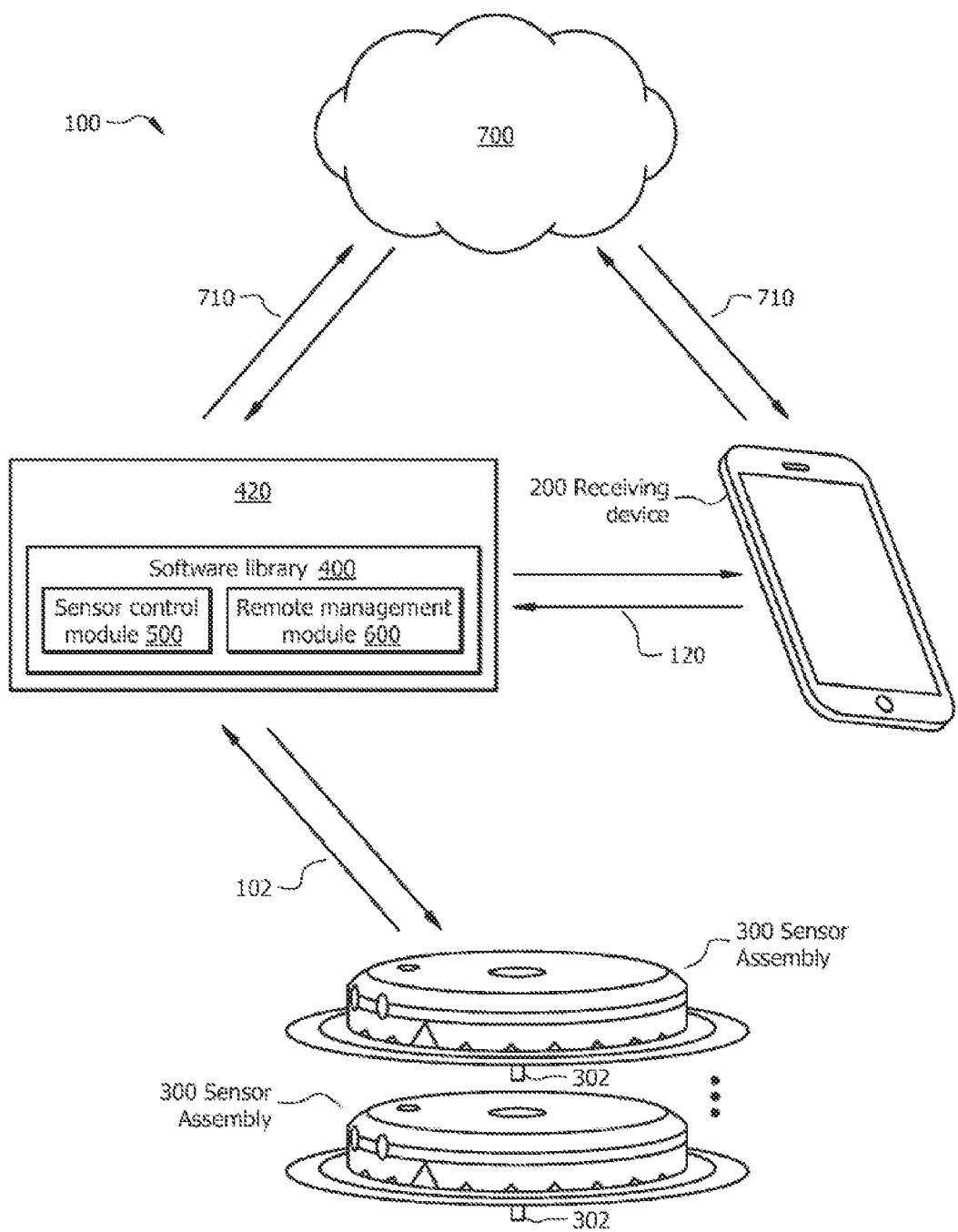
FIG. 1 is a system overview of a system that includes a software library, receiving device, and sensor assembly.

Reference will now be made in detail to the various exemplary embodiments of the disclosed subject matter, exemplary embodiments of which are illustrated in the accompanying drawings.

The system can include a device that receives analyte data measured by an analyte monitor and medication delivery data recorded by a delivery device, and processes and/or displays that data, in any number of forms, to the user. This device, and variations thereof, can be referred to as a "receiving device," "reader device" (or simply a "reader"), "handheld electronics" (or simply a "handheld"), a "portable data processing" device or unit, a "data receiver," a "receiver" device or unit (or simply a "receiver"), or a "remote" device or unit, to name a few. This device can be a smartphone, a smartwatch, or display device.

The system can also include an in vivo analyte monitor sensor assembly, which can comprise various types of monitors. For example, "Continuous Analyte Monitoring" systems (or "Continuous Glucose Monitoring" systems), can transmit data from a sensor device to a reader device continuously without prompting, e.g., automatically according to a schedule. "Flash Analyte Monitoring" systems (or "Flash Glucose Monitoring" systems or simply "Flash" systems), as another example, can transfer data from a sensor device in response to a scan or request for data by a reader device, such as with a BLUETOOTH® Low-Energy (BLE), Near Field Communication (NFC) or Radio Frequency Identification (RFID) protocol. An in vivo analyte monitoring sensor assembly can also operate without the need for finger stick calibration.

In vivo monitoring sensor assemblies can include a sensor that, while positioned in vivo, contacts the bodily fluid of the user and generates analyte data indicative of the analyte levels contained therein. The sensor assembly can reside on the body of the user and contain the electronics and power supply that enable and control the analyte sensing. The sensor assembly, and variations thereof, can also be referred to as an "on-body electronics" device or unit, an "on-body" device or unit, or a "sensor data communication" device or unit, or analyte sensor, sensor device, in vivo analyte monitor sensor assembly, sensors, to name a few.

Further, the system can include an external device for use with the analyte sensor. For example and without limitation, external devices can include delivery devices that use information from the analyte sensor to determine or deliver amounts of a medication or other beneficial agents to a user. Additionally or alternatively, external devices can include other sensors, such as other analyte sensors, accelerometers, pressures sensors, or can include external computing devices, such as a medical server or a smartphone application configured to use analyte sensor information to provide additional insights to a user, including but not limited to insights related to medical conditions, well-being, fitness, appetite, or other medical or non-medical insights or analysis.

Generally, and as set forth in greater detail below, the disclosed subject matter provided herein includes a software library within a receiving device for communicating with analyte sensors and permitting third-party applications access to the sensor data for use in medically necessary applications or applications related to the well-being of the user. The system further includes a software library that can be implemented independently of the sensors and integrated within third-party applications to allow access to the sensor data. The sensor control module can further communicate with the sensor assemblies in such a manner to receive data simultaneously or substantially simultaneously from a plurality of such sensor assemblies. The system further enables the transfer of sensor information from the sensor control module to a remote management module.

The embodiments described herein can be used to monitor and/or process information regarding any number of one or more different analytes. Analytes that may be monitored include, but are not limited to, acetyl choline, amylase, bilirubin, cholesterol, chorionic gonadotropin, glycosylated hemoglobin (HbA1c), creatine kinase (e.g., CK-MB), creatine, creatinine, DNA, fructosamine, glucose, glucose derivatives, glutamine, growth hormones, hormones, ketones, ketone bodies (e.g., β-hydroxybutyrate), lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times.

FIG. 1 is a schematic diagram depicting an example embodiment of a system 100 that includes a modular connectivity framework using a software library 400, various applications 420, a sensor assembly 300, and a receiving device 200.

In accordance with the disclosed subject matter, a non-transitory computer-readable storage medium includes a software library for use by applications 420 on a receiving device 200, or standalone devices such as a pump, insulin pen, etc., to obtain sensor data. The software library can include a sensor control module, a remote management module, and include software logic for communication with a plurality of sensors and applications. The sensor control module can authenticate the receiving device to allow the receiving device to receive sensor data, including by enabling communication with each of the plurality of sensors to receive sensor data including data indicative of a different signal. The sensor control module can further store the sensor data in a memory of the computing device. The sensor control module can obtain an output indicative of the different signals from the sensor data of each of the plurality of sensors. The sensor control module can provide the output of the different signals from the sensors to the authenticated third-party application running on the computing device.

The system 100 includes a software library 400 that functions using a modular architecture enabling a sensor control module 500 to communicate with and reside within various applications 420 on the receiving device 200. Applications 420 may further interface with sensor assembly 300 through the sensor control module 500, and in particular, by providing the request to the communication control module 540 (on FIG. 5) to interface directly with the sensor assembly 300. The sensor assembly 300 can also be one device with different sensors 302 or one sensor 302 configured to detect more than one analyte.

The receiving device 200 includes one or more applications 420, with each application instance embedding software library 400. The receiving device 200 uses a modular connectivity framework for the applications 420. In particular, the applications 420 each include a software library 400 including a remote management module 600 and sensor control module 500 for communicating with the one or more sensor assemblies 300. The software library 400 may also run as a service that executes simultaneously with the underlying application allowing the sensor control module 500 or remote management module 600 to execute as a service alongside one or more applications.

Sensor control module 500 may further interface with the sensor data. The various modules within the software library 400 implemented within the application 420 can send and receive communication with the sensor assembly 300 via communication link 102.

While the sensor control module 500 is within the application 420 in a receiving device 200, the sensor control module 500 could have base components in a second receiving device, such as a smartwatch, mobile device, or other wearable device. While such a device may not allow for a user interface experience that would be provided by a smartphone or tablet or computer, the smartwatch or wearable device can incorporate the sensor control module 500 to permit direct communication through the sensor control module 500 on the smartwatch or mobile wearable device with the sensor assembly 300. This would allow for applications specific to wearable devices to use sensor data. The wearable devices can synch separately with the receiving device 200, which can be used to perform the majority of the user login, initialization, authentication, and consent features to implement and initiate the receipt of sensor data.

Communication link 102 can be a wireless protocol including BLUETOOTH®, BLUETOOTH® Low Energy (BLE, BTLE, BLUETOOTH® SMART, etc.), Near-Field Communication (NFC) and others. The communication links 102 can each use the same or different wireless protocols. The system 100 may be configured to communicate over other wireless data communication links such as, but not limited to, RF communication link, infrared communication link, or any other type of suitable wireless communication connection between two or more electronic devices, which may further be uni-directional or bi-directional communication. Alternatively, the data communication link may include wired cable connection such as, for example, but not limited to, RS232 connection, USB connection, FireWire, Lightning, or serial cable connection.

For example, and as embodied herein, communication link 102 can be configured to use a BLUETOOTH® protocol, such as BLE, or communication link 102 can be configured to use an NFC protocol. Additionally or alternatively, another communication link not shown may exist between a second sensor assembly and it can be configured to use BLE or both NFC and BLE. The communication links can be configured to perform different operations. For example, communication link 102 can be configured to perform only activation of the sensor assembly. Furthermore, communication links can have different configurations depending on the overall system architecture or the components that are activated or being used in the system at a given time. For example, and as embodied herein, communication link 102 can have a first communication configuration when the receiving device 200 is active in the system and a second communication configuration when the receiving device is not active or not included in the system.

In the first communication configuration, the communication link 102 can be configured only to perform activation of the sensor using an NFC wireless protocol. In another configuration, BLE capability (if provided) can remain inactive between the sensor assembly 300 and the applications 420. The application 420 can activate the sensor assembly 300 using NFC wireless protocol and obtain sensor context information. Sensor context information can include authentication information for authenticating a communication session with the sensor assembly 300, encryption information to enable encrypted data communication over the communication links, and a BLE communication address to initiate a BLE connection with the sensor assembly 300. The software library 400 may also obtain the sensor context information from the sensor assembly 300 over BLE. Using the sensor context information, the software library 400 includes capabilities to allow a session to switch from an application 420 on the receiving device 200 such as a smartphone to another application 420 on another receiving device 200 such as a smartwatch. The sensor context information can be transmitted within the applications 420.

In accordance with the disclosed subject matter, the sensor assembly 300 as shown may include sensing elements for detecting different analytes within the same sensor assembly. The system 100 may also include multiple sensor assemblies 300, as shown, connected via a communication link having similar capabilities of communication to the communication link 102 described herein. Two or more sensor assemblies 300 can also be used in conjunction by having multiple sensing elements that together produce the reading for an analyte, or separately produce readings for different analytes. Any number of sensor assemblies could be used together to measure any number of different analyte values, and two sensor assemblies are shown for illustration, not limitation, in this disclosure.

In some embodiments, the application 420 can be configured to access the software library 400 through a remote cloud 700 infrastructure via wireless communication links 710. In certain embodiments, the communication link 710 includes a wireless communication section configured for bi-directional radio frequency (RF) communication with other devices to transmit and/or receive data to and from the system 100. In addition, the communication link 710 may also be configured to include physical ports or interfaces such as one or more of a USB port, an RS-232 port, a serial port, a IEEE 1394 (Firewire) port, an Ethernet port or any other suitable electrical connection port to allow data communication between the system 100 and receiving device 200, such as a personal computer, a laptop computer, a notebook computer, an iPad, a tablet computing device, a cellular telephone, a smart phone, a personal data assistant, a workstation, a server, a mainframe computer, a cloud computing system, an external medical device, such as an infusion device, an analyte monitoring device, or including an insulin delivery device, or other devices that are configured for similar complementary data communication. In certain embodiments, communication link 710 may include a cellular communication protocol, a Wi-Fi (IEEE 802.1x) communication protocol, or an equivalent wireless communication protocol which would allow secure, wireless communication of several units (for example, per HIPPA requirements) while avoiding potential data collision and interference.

In other embodiments, the wireless communication section 710 may be configured for infrared communication, BLUETOOTH® communication, wireless USB communication, ZigBee communication, cellular communication, Wi-Fi (IEEE 802.1 lx) communication, RFID (passive or active) communication, or any other suitable wireless communication mechanism to enable the receiving device 200 to communicate with other devices such as infusion devices, analyte monitoring devices, computer terminals, servers, personal computers, laptop computers, notebook computers, iPads, tablet computers, cell phones, smart phones, workstations, mainframe computers, cloud computing systems, communication enabled mobile telephones, personal digital assistants, or any other communication devices with which the patient or user of the device may use in conjunction therewith, in managing the treatment of a health condition, such as diabetes.

The system 100 may be configured to operate as an open loop system, a closed-loop system, and a hybrid closed-loop system. An open loop system requires manual user input to control certain functionalities related to the sensor assembly 300. A closed-loop system uses data from the sensor assembly 300 and algorithms to control the software library 400 without user input. In a hybrid system, input may be required from a user to control the application 420 and initiate the software library 400. A hybrid closed-loop system can be used in conjunction with, or in place of, a closed-loop system. As disclosed herein, regulatory clearance can be limited to software library 400 irrespective of the type of system configuration used in the system 100.

Receiving Device

Figure 2:
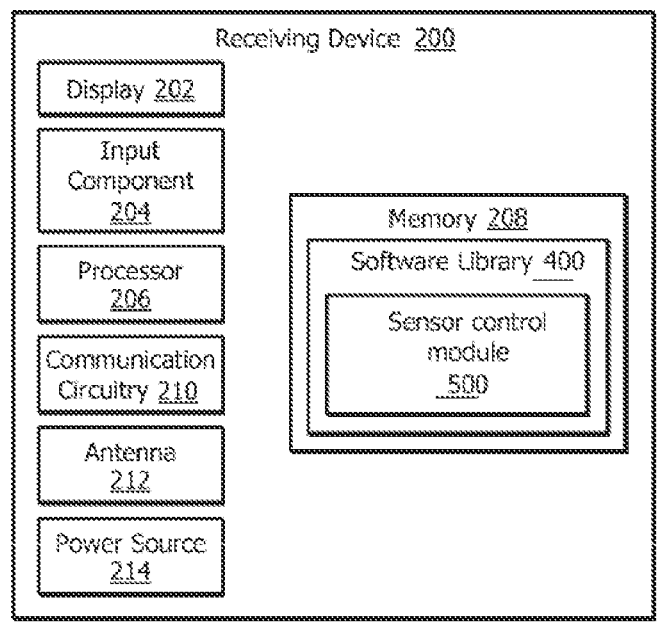
FIG. 2 is a block diagram depicting an example embodiment of a receiving device.

FIG. 2 is a block diagram depicting an example embodiment of a receiving device 200. A software library 400 can be provided to a third-party and incorporated within an application 420 for a multi-purpose receiving device 200, such as a mobile phone, tablet, personal receiving device, or other similar receiving device. Receiving device 200 embodying and executing device application software can also be referred to as a computing device or a multi-purpose device. Receiving device 200 refers to a suitably configured hardware device which is executing an application 420 that incorporates a software library 400 having a sensor control module 500 configured for communication with the sensor assembly 300. Here, receiving device 200 can include a display 202, input component 204, and a processor 206 coupled with memory 208. Also included can be communication circuitry 210 coupled with an antenna 212, and power source 214. As understood by one of skill in the art, these components are electrically and communicatively coupled in a manner to make a functional device. As embodied herein, the memory 208 can include an application and a sensor control module 500 for the sensor assembly 300. The application 420 can also import a software library 400 including the sensor control module 500. The software library 400 and the sensor control module 500 can be developed by the provider of the sensor assembly 300.

The receiving device can have the majority of the processing capability of the system 100 for rendering end-result data suitable for display to a user. The receiving device 200 can be a smartphone or a smartwatch.

The receiving device 200 can receive analyte data, such as glucose data and calculate low and high analyte level and generate corresponding alarms and messages. The receiving device 200 can also mirror an alert generated by another device, such as the sensor assembly 300. The receiving device 200 can process analyte data with the processor 206 and render on the display 202 analyte-related information as value, trend, and graph, and provide additional messaging and notification based on the received analyte level.

Sensor Assembly

Figure 3:
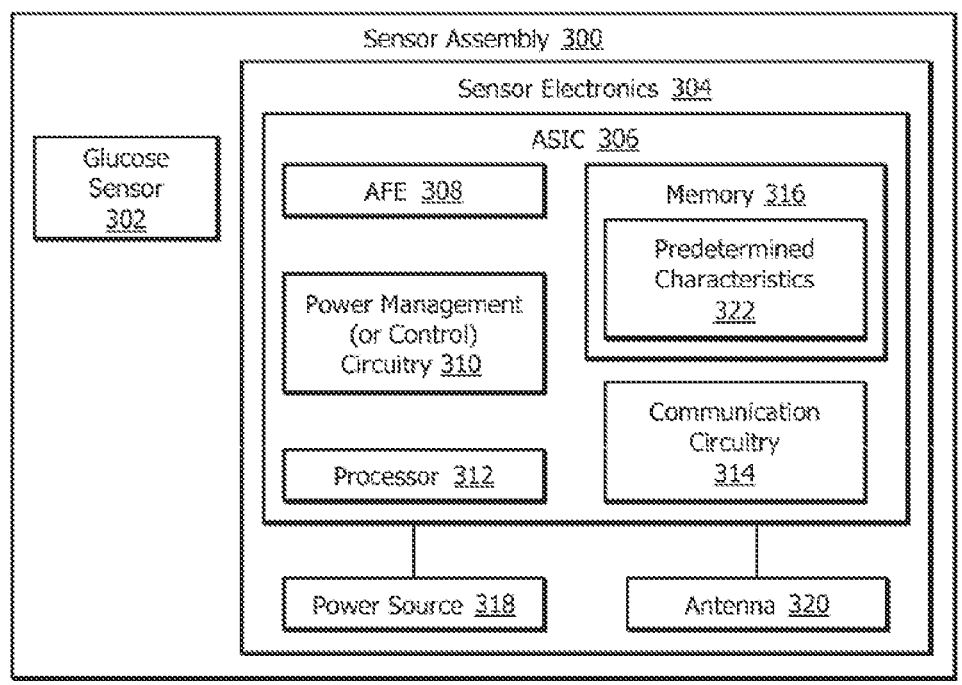
FIG. 3 is a block diagram depicting an example embodiment of a sensor assembly.

FIG. 3 is a block diagrams depicting an example embodiment of a sensor assembly 300 comprising a glucose sensor 302 and sensor electronics 304 (including analyte monitoring circuitry). Glucose sensor 302 can be an in vivo analyte sensor and have a use period of about 13-30 days. Sensor assembly 300 can be without wide-area network communication capability.

The glucose sensor 302 generates raw data signals for measurements of the patient's glucose level. Sensor electronics 304 are operatively coupled to the glucose sensor 302, the sensor electronics 304 comprising a memory 316 storing one or more predetermined characteristics 322 associated with the sensor electronics 304. The memory 316 can be a so-called "one-time programmable" (OTP) memory, which can include supporting architectures or otherwise be configured to define the number times to which a particular address or region of the memory can be written, which can be one time or more than one time up to the defined number of times after which the memory can be marked as unusable or otherwise made unavailable for programming. Subject matter disclosed herein relate to systems and method for updating said OTP memories with new information.

The sensor electronics 304 can include a single semiconductor chip, as depicted, that can be a custom application specific integrated circuit (ASIC 306). Shown within ASIC 306 are certain high-level functional units, including an analog front end (AFE 308), power management (or control) circuitry 310, processor 312, and communication circuitry 314 (which can be implemented as a transmitter, receiver, transceiver, passive circuit, or otherwise according to the communication protocol). As an example only and not by way of limitation, example communication circuitry 314 can include a BLUETOOTH® Low-Energy ("BLE") chipset, Near-Field Communication ("NFC") chipset, or other chipsets for use with similar short-range communication schemes, such as a personal area network according to IEEE 802.15 protocols, IEEE 802.11 protocols, infrared communications according to the Infrared Data Association standards (IrDA), etc. The communication circuitry 314 can transmit and receive data and commands via interaction with similarly-capable communication modules. Certain communication chipsets can be embedded in ASIC 306 (e.g., an NFC antennae).

The sensor assembly 300 can use application layer encryption using one or more block ciphers to establish mutual authentication and encryption of other devices in the system 100. The use of a non-standard encryption design implemented in the application layer has several benefits. One benefit of this approach is that in certain embodiments the user can complete the pairing of the sensor assembly 300 and another device with minimal interaction, e.g., using only an NFC scan and without requiring additional input, such as entering a security pin or confirming pairing. Sensor assembly 300 can be configured to dynamically generate authentication and encryption keys. Sensor assembly 300 can also be pre-programmed with a set of valid authentication and encryption keys to use with particular classes of devices. The ASIC 306 can be further configured to perform authentication procedures with other devices (e.g., handshake, mutual authentication, etc.) using received data and apply the generated key to sensitive data prior to transmitting the sensitive data.

In this embodiment, both AFE 308 and processor 312 are used as analyte monitoring circuitry, but in other embodiments either circuit can perform the analyte monitoring function. Processor 312 can include one or more processors, microprocessors, controllers, and/or microcontrollers, each of which can be a discrete chip or distributed amongst (and a portion of) a number of different chips.

Memory 316 included within ASIC 306 and can be shared by the various functional units present within ASIC 306, or can be distributed amongst two or more of them. Memory 316 can also be a separate chip. Memory 316 can be volatile and/or non-volatile memory. In this embodiment, ASIC 306 is coupled with a power source 318, which can be a coin cell battery, or the like. AFE 308 interfaces with glucose sensor 302 and receives measurement data therefrom and outputs the data to processor 312 in digital form. This data can then be provided to communication circuitry 314 for sending, by way of antenna 320, to software library 400.

The sensor 302 can alternatively monitor other analytes, for example, acetyl choline, amylase, bilirubin, cholesterol, chorionic gonadotropin, creatine kinase (e.g., CK-MB), creatine, DNA, fructosamine, glutamine, growth hormones, hormones, ketones, ketone bodies (e.g., β-hydroxybutyrate), lactate, peroxide, prostate-specific antigen, prothrombin, RNA, thyroid stimulating hormone, and troponin. For example, ketone sensors and dual glucose and ketone sensors are described in U.S. Publication No. 2022/0186278, U.S. Publication No. 2020/0237276, U.S. Publication No. 2020/0237275, U.S. Publication No. 20210219885, U.S. Publication No. 2020/0237276, U.S. Publication No. 20210369155, U.S. Publication No. 2022/0186278, and U.S. Pat. No. 11,091,788, all of which are herein expressly incorporated by reference in their entireties for all purposes.

The sensor assembly 300 includes a sensor assembly embedded library (not pictured) configured for providing sensor assembly data to the software library 400 based on information received from the sensor assembly 300. Sensor assembly data can include glucose readings, data types, range, real time and historical glucose and trends, sensor operating information, and sensor system information.

Software Library

Figure 4:
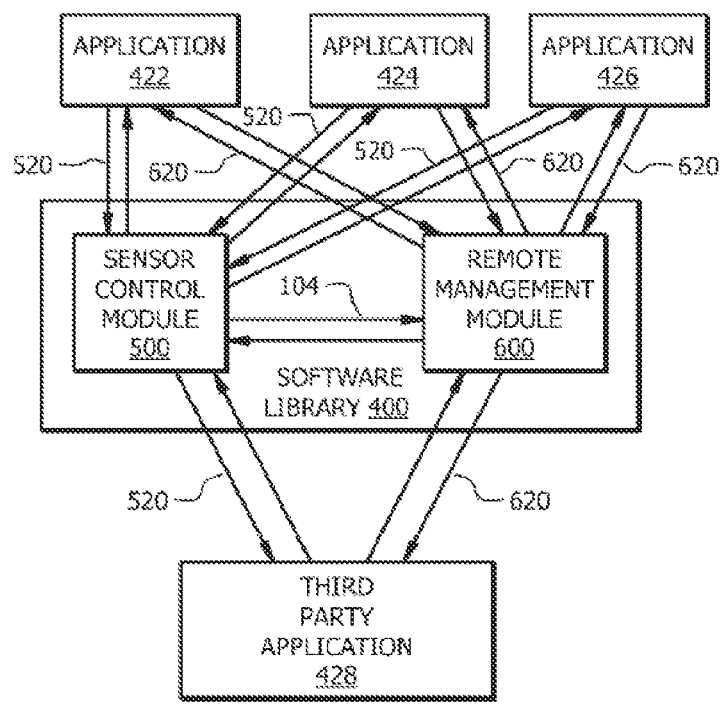
FIG. 4 is a block diagram depicting an example software library, including a sensor control module and a remote management module, for communication with applications.

FIG. 4 is a block diagram depicting an example of a software library 400 for communication with applications 420, shown as applications 422, 424, 426, and third-party application 428. References to application 420 refers to one or more of the applications 422, 424, 426 or third-party application 428. Software library 400 includes a sensor control module 500 and a remote management module 600, each of which is capable of independently communicating with applications 422, 424, 426 or third-party application 428. In accordance with the disclosed subject matter, sensor control module 500 and a remote management module 600 may each provide a single uniform interface to communicate with the applications 422, 424, 426 or third-party application 428.

Software library 400 may use a modular architecture and may be made available via a software development kit that can be made for common use by applications 420. The software library 400 may include two modules, each of which could be independently provided for use by other applications 420. The first such module may be a sensor control module 500. The sensor control module may communicate with the sensor assembly 300 and receive a particular result of the value from the sensor assembly 300. The sensor control module 500 may further communicate with applications 422, 424, 426, or third-party application 428 using a sensor control module interface 520.

The software library 400 may further include a remote management module 600 that will be further described below. The remote management module 600 communicates with applications 422, 424, 426, or third-party application 428 using a remote management module interface 620.

The remote management module 600 may further receive the sensor data from the sensor control module 500 via the inter-module interface 450 and can further be used to store that data in a remote server 640 (shown on FIG. 6) for remote storage, such as in the cloud. Biosensor data may be collected and stored in an anonymous account in the cloud with a unique user ID. The unique user ID may allow for the tracking and analyzing of users in connected third-party applications. By using a remote management module 600, an application developer can also take advantage of a consistent user interface for account management for a user across different third-party applications such as third-party application 428. Data privacy can further be integrated into the remote management module 600 for account management purposes.

The sensor control module 500 may receive a request to initiate the sensor assembly 300. The sensor control module 500 may include logic to identify the particular type of receiving device 200 making the request, and can perform an authentication function for the receiving device 200. Authentication may use a three-pass design with different keys. Keys can be aligned with differential roles (manufacturer, application developer, etc.). Sensitive commands that could leak security information can trigger authenticated encryption using an authenticated additional keyset. The sensor data provided to the sensor control module 500 and sent to the application 422, 424, 426 or third-party application is highly sensitive and can be beneficial to be protected. Medical data associated with a patient is sensitive data at least in part because this information can be used for a variety of purposes, including for health monitoring and medication dosing decisions. As embodied herein, the various modules and applications 422, 424, 426, and third-party application 430 can be configured compliant with a security interface designed to protect the Confidentiality, Integrity and Availability ("CIA") of this communication and associated data. To address these CIA concerns, to facilitate the confidentiality of data, communication connections between the sensor assembly 300 and the sensor control module 500 can be mutually authenticated prior to transmitting sensitive data. The same would be done for communication between the sensor control module 500 and application 422, 424, 426, and third-party application 428. Communication connections can be encrypted using a device-unique or session-unique encryption key. As embodied herein, the encryption parameters can be configured to change with every data block of the communication.

As embodied herein, to guarantee the integrity of data, encrypted communications between any two components (e.g., a sensor control module 500 and sensor assembly 300) can be verified with transmission integrity checks built into the communications. As embodied herein, session key information, which can be used to encrypt the communication, can be exchanged between two devices after the devices have each been authenticated. Encrypted communications between a sensor assembly 300 and a dedicated sensor control module 500 can be validated with an error detection code or error correction code, including as an example and not by way of limitation, non-secure error-detecting codes, minimum distance coding, repetition codes, parity bits, checksums, cyclic redundancy checks, cryptographic hash functions, error correction codes, and other suitable methods for detecting the presence of an error in a digital message.

The sensor control module 500 may further generate state information to maintain the active status for the receiving device 200 while it remains desirous of the sensor data.

The sensor control module 500 may include a user interface 510 that can enable data sharing for the applications, including necessary permissions to enable data sharing. The user interface 510 at the sensor control module 500 may also display the sensor data received from the sensor assembly 300.

The user interface 510 of the software library is disclosed herein as a modular user interface 510 that allows for sharing and display of the multiple different analytes that can be measured from the different sensor assemblies 300. In particular, as disclosed herein, by using a software library 400 and sensor control module 500, a shared user interface can be developed for display of sensor data from multiple sensor assemblies 300. The user interface 510, when shared, could toggle between sensor data related to the various sensor assemblies 300, display sensor data on one screen, or use multiple different combinations to display the sensor data.

Communication between the sensor control module 500 and applications 422, 424, 426, or third-party application 428 occurs over a sensor control module interface 520. Communication between the remote management module 600 and applications 422, 424, 426, or third-party application 428 occurs over a remote management module 620. The communication is further driven using an event notification or callback process. For example, when the sensor control module 500 receives a request from a third-party application 428 for sensor data, the request may be communicated through the sensor control module interface 520 and an event may be generated at the user interface 510 of the sensor control module 500 to initiate authentication.

As another example, when sensor data is received over communication link 102 by the sensor control module 500, an event can be generated to notify other modules or components within the software architecture that data can be displayed on a user interface 510 of the sensor control module 500.

By having a modular architecture using a software library 400 and sensor control module 500 to interface with the applications 422, 424, 426 and third-party application 428, the system enables communication with different types of sensor assemblies 300, including multiple sensor assemblies 300. In particular, the communication control module 540 may include functionality specific to each of the sensor assemblies 300 within the system, and may simultaneously access and communicate with the various sensor assemblies 300 to receive sensor data.

As another example, a developer of a third-party application 428 may elect to use certain modules of the software library 400 to support the functionalities within the third-party application 428. For example, certain third-party applications 428 may use the sensor data as wellness data. Wellness data can generally include any type of data associated with a person's health, such as their weight, heart rate, blood pressure, blood glucose level, or the like. Sensor assemblies may provide resulting sensor data that may include such wellness data. To the extent a third-party application desires to make use of the sensor data, the third-party application may access the respective module from the software library 400 for the desired sensor data. With the software library 400, the third-party application 428 does not need to directly interface with the sensor assembly 300 to receive sensor data. The software library 400 includes a sensor control module 500 that can receive the sensor data and provide that to the respective third-party application 428. It should be understood that "third party" can correspond to an entity different than the manufacturer of the sensor assembly 300 or software library 400. The third-party application 428 may have access to certain permitted data on database 530 accessible through sensor control module interface 520. Separately, the third-party application 428 may include its own database (not pictured) for storing the sensor data received through the sensor control module 500.

In certain applications, software that operates in conjunction with a medical device such as a sensor assembly sensing data from a user interaction or user health information may be regulated as medical device software. Certain standards pertain to regulation of medical device software, including with reference to ISO 13485:2016 "Medical devices—Quality Management Systems—Requirements for regulatory purposes," ISO14971:2012 "Medical devices—Application of Risk Management to Medical Devices," and IEC 62304, Ed 1.1:2015 Medical Device Software—Software Lifecycle Processes." In particular, regulation requires that software that functions as a medical device (commonly referred to as Software as a Medical Device) is to be regulated by a regulatory agency, such as the Food and Drug Administration in the United States. This regulation at least requires submitting the application for regulatory clearance.

As described by the disclosed subject matter, the regulated portion of software as a medical device can be contained within the software library 400 and the sensor assembly 300. This can allow applications 422, 424, 426, or third-party application 428 not to have to undergo regulatory approval and clearance when making use of the sensor data. In particular, third-party applications may be developed by third-party developers for one or more wellness purposes that will not require the third-party developer to submit the application for approval based on definitions of software as a medical device as the regulated functionalities would all be contained within the software library 400. This will benefit users by allowing the creation of different wellness tracking applications or other uses of the sensor data that may not have originally been considered by the original manufacturer of the sensor assembly 300.

For applications 422, 424, 426, or third-party application 428, a sensor control module interface 520 is used to communicate with the sensor control module 500. By using the sensor control module interface 520, the applications 422, 424, 426 or third-party application 428 can receive data through the sensor control module 500.

The sensor control module 500 may optionally include an alarm module (not pictured) to manage alarms and notifications triggered by the sensor data. In accordance with the disclosed subject matter, the alarm module may include logic to generate alarms for each type of sensor measured by the sensor assembly 300. In particular, the alarms may be triggered if an issue arises with the device hardware of the sensor assembly 300. Additionally, the alarms may be triggered indicating a particular condition with the user being monitored by the sensor assembly 300. In accordance with the modular framework, the alarm logic for the alarm module may be separately maintained within the sensor control module 500.

As described herein, for illustration purposes, the alarm module works with the application 422, 424, 426 or third-party application 428 and the sensor control module 500. The sensor control module 500 receives sensor data from the sensor assembly 300 representing an analyte value. One such value could be a glucose reading. The sensor control module 500 and the alarm module may have threshold detection logic to identify the triggering conditions for an alarm based on a particular analyte value, such as a glucose reading.

During initialization, the third-party application 428 or application 422, 424, 426 can also provide conditions that would require the triggering of an alarm as a callback function. The triggering may involve logic that factors in the value of the sensor data and a temporal relationship. For example, if the sensor assembly provides glucose data, a triggering value may be set to trigger the alarm along with a temporal relationship such as if the value increases by a certain number over a period of time, or remains above a certain value for a period of time. These triggering conditions may also include rate of change as a mechanism to trigger an alarm. By incorporating the alarm module within the sensor control module 500, alarm conditions that require regulatory review and approval can be incorporated within the sensor control module 500, further reducing the need to submit application 422, 424, 426, or third-party application 428 for regulatory approval.

Sensor Control Module

Figure 5:
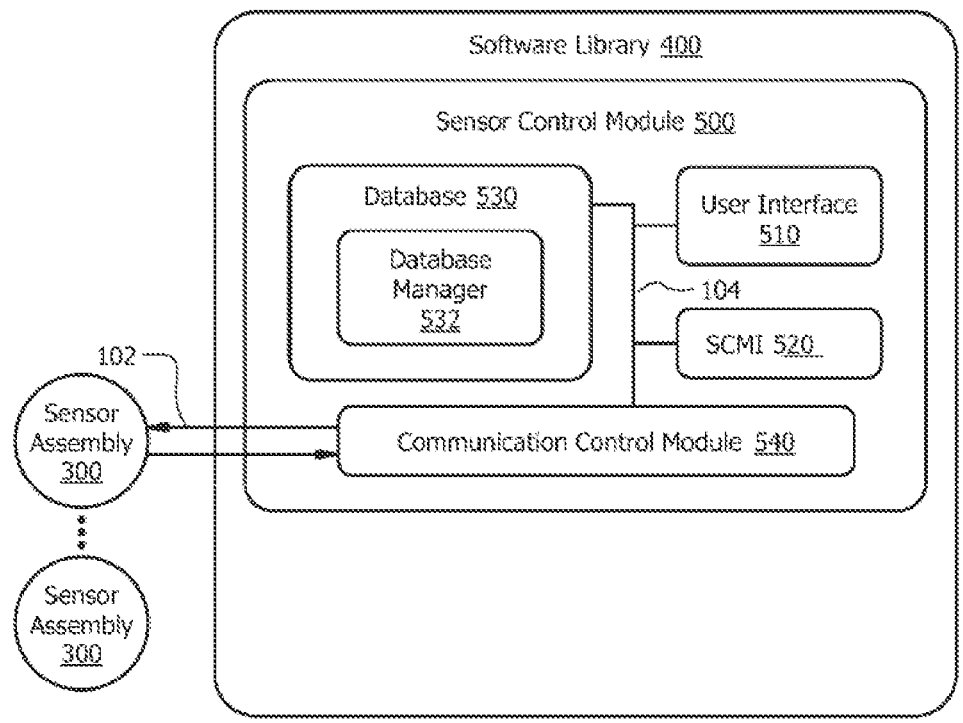
FIG. 5 is a block diagram depicting an example embodiment of the sensor control module.

FIG. 5 is a block diagram depicting an example embodiment of the sensor control module 500 within a software library 400.

In certain embodiments, the sensor control module 500 includes a communication control module 540. The communication control module 540 includes logic to communicate over a communication link 102 to the sensor assembly 300. The communication control module 540 includes further logic for receiving sensor data and displaying the sensor data at a user interface 510. In particular, each sensor assembly 300 includes control logic to perform operations related to sensor communications, especially those that are proprietary. For example, the sensor assembly 300 includes logic provided by the sensor control device's manufacturer to receive sensor measurements and perform complex algorithms on the measurements including data decryption and glucose calculations. In this regard, the communication control module 540 may only need to receive the result of the processing and calculation, with data accuracy and integrity for protection of complex proprietary algorithms occurring at the closed sensor assembly 300. The sensor assembly 300 further includes logic provided by the sensor control device's manufacturer to perform authentication. This allows the sensor assembly 300 to include functionality to provide sensor data that is the resulting data from the sensor measurements for a variety of sensors to the communication control module 540. By using a modular framework, the communication control module 540 includes logic to receive data from a plurality of sensor assemblies 300, enabling substantially simultaneous communication from multiple sensor assemblies 300. This allows authorized third parties to develop mobile apps without requiring that those third parties take on the significant responsibility of independently providing the same level of performance and results accuracy.

This further enables various third-party companies to develop their own mobile applications that work with the manufacturer's sensor assemblies 300 through the software library 400 and the sensor control module 500, with those third-party companies having a variety of use cases that are different from those currently supported by the manufacturer. The utilization of a modular architecture enables third parties to only need to implement a smaller number of interface calls and reference the respective modular components of the software library 400 for implementation.

Communication within the sensor control module 500 to various components occurs over a sensor control module messaging channel 104. The user interface 510 can be used to display the sensor data once received over the sensor control module messaging channel 104.

Applications 422, 424, 426, or third-party application 428 include logic to communicate with the communication control module 540 over a sensor control module interface 520 and operate within the framework to enable receipt of sensor data. The application 420, 424, 426, or third-party application 428 requests sensor control module 500 to perform activation functions by first initiating the sensor control module 500 followed by sending a request to obtain sensor data. The sensor control module 500 includes a sensor control module interface 520 to ensure consistency for overlapping functions required of various applications 422, 424, 426 or third-party application 428. The sensor control module interface 520 is implemented as an application program interface (API) in the underlying application 422, 424, 426, or third-party application 428. A standard interface for shared functions also allows the sensor control module 500 to be used for receipt of sensor data from multiple sensors substantially simultaneously. Logic is contained within the software library for managing the activation of various applications 422, 424, 426 or third-party application 428 that have been authorized to receive sensor data. The sensor control module 500 may further include logic to control and manage the states of the various applications 422, 424, 426 or third-party application 428 via the sensor control module interface 520.

The sensor control module 500 within the software library 400 is positioned as a software as a medical device for regulatory clearance in conjunction with the sensor assembly 300. By housing the components that trigger software as a medical device regulatory issues within the software library communicating with the sensor assembly, additional third-party application 428 avoids the need to be submitted for regulatory approval. This further allows other application developers to build other use cases without having to submit the use-case for the application for regulatory review, and allows unregulated applications to take advantage of the sensor data. This advantage occurs by using the modular logic as described for the software library 400.

The user interface 510 provides a uniform interface for the applications 422, 424, 426 or third-party application 428 to display received sensor data. The user interface 510 may perform a user consent and onboarding function for the applications 422, 424, 426 or third-party application 428. Onboarding includes having a new user of the applications 422, 424, 426 or third-party application 428 completing the necessary consents to have access to the sensor data. The user interface 510 may further include a ready check to determine through the communication control module 540 that the various sensor assemblies 300 are functioning properly. The user interface 510 may include a display functionality to display the sensor data. The user interface 510 can be used in common form for the applications 422, 424, 426 or third-party application 428 for any number of shared functions, such as for account creation of a user, consents for data privacy and sharing, and other similar functions. In accordance with the disclosed embodiments, the sensor control module 500 may present a particular customized user interface 510 when application 422, 424, 426 developed by the manufacturer of the sensor assembly 300 is in operation, but a wholly different user interface 510 for a third-party application 428 that is not developed by the manufacturer of the sensor assembly 300. The look and feel of the user interface 510 thus automatically adjust depending on whether the applications 422, 424, 426 or third-party application 428 has requested the sensor data. As disclosed herein, the sensor control module 500 may be implemented without a user interface 510 component. In this configuration, the sensor control module interface 520 functions to provide information directly to the display of the underlying applications 422, 424, 426 or third-party application 428.

The sensor control module 500 may optionally include integrity and initialization check of accounts to allow connectivity with the sensor and access to the sensor data. Applications 422, 424, 426 or third-party application 428 requests initialization of the sensor control module 500 on start-up of the applications 422, 424, 426 or third-party application 428 by supplying identifying information to the sensor control module 500 and credentials that the sensor control module 500 can use for authentication. If the integrity check fails, the sensor control module 500 will not allow for operation of that application 422, 424, 426 or third-party application 428. For third-party application 428, a remote management module 600 can be used to revoke access to the sensor control module 500 or remove authorization based on the manufacturer's current permissions and goals as determined by the connectivity between the remote management module 600 and the remote server 640. The remote management module 600 can also initiate a process to revoke the authentication of the third-party application 428 from the sensor control module 500 to prevent it from further operation. After successful initialization, the sensor control module 500 initializes the remote management module 600 by providing identifying information and credentials for authentication.

The sensor control module 500 may include protections to ensure that a proper authenticated application 422, 424, 426 or third-party application 428 had made requests for sensor data.

The communication control module 540 may communicate through the communication link 102 to the sensor assembly 300. Using a sensor control module messaging channel 104, the sensor data received from sensor assembly 300 is provided to other components of the sensor control module 500. The sensor data may also communicate to the remote management module 600 via another inter-module interface 450 between the sensor control assembly 500 and the remote management module 600. The sensor data may be further stored in database 530 managed by a database manager 532.

Because of the modular architecture of the software library 400, the communication control module 540 can receive data from any of the various types of sensors represented by sensor assembly 300. This allows for substantially simultaneous receipt of sensor data for the system. Support for multiple different types of sensors occurs at the system level in modular form allowing for future expansion as new sensors are built for tracking additional data by incorporating the necessary modules within the software library 400 and sensor control module 500.

The user interface 510 includes limited functionality to display the sensor data, such as glucose value, and is maintained in this form to allow for uniform use across multiple sensor readings for display of the sensor data. Processing and calculations occur at the sensor assembly 300, and the communication control module 540 receives that sensor data result as a value.

Once the communication control module 540 receives the sensor data, it may post an event by generating an event notification that will inform the respective application 422, 424, 426 that sensor data may be available and accessed through the sensor control module interface 520. The data may be stored in database 530 and accessed directly through the sensor control module interface 520. By using the sensor control module interface 520 and user interface 510, the sensor control module 500 presents a uniform interface for the various applications 422, 424, 426 or a third-party application 428 to activate and receive results of the sensor data. Additionally, the uniform interface 510 includes software logic to identify and register various applications 422, 424, 426 or third-party application 428 to receive certain types of sensor data via callbacks. As an example, if glucose sensor data is available, the uniform interface software logic through sensor control module interface 520 will invoke a callback within the applications 422, 424, 426, or third-party applications 428 authorized to receive glucose sensor data.

The uniform interface logic can use the unique identifier to identify the sensor assembly 300 for which the sensor data request is being made. Although not depicted, according to one aspect of the embodiments, a unique identifier object can be created as an initial step, if one does not already exist. In some embodiments, for example, the unique identifier object can be a user-specific identifier object (e.g., a username, a user profile, or a user account ID) that is inputted, generated, or facilitated by a software application, module, or routine within the software library 400 that is running on the application 420. In other embodiments, the unique identifier object can be associated with a physical device, e.g., a particular sensor assembly 300, and can comprise, for example, a serial number, a media access control (MAC) address, a public key, a private key, or a similar string of characters.

According to another aspect of the embodiments, each of the applications 422, 424, 426, or third-party application 428 includes parameters that can be passed to the sensor control module 500 when a respective call is made by an application 422, 424, 426, or third-party application 42. These various structures and data types can be made available to the sensor control module 500 to assist the sensor control module 500 in accessing the sensor assembly 300 to receive sensor data.

According to another aspect of the embodiments, the sensor control module 500 may store the meta data and state information associated with the sensor assembly 300 or application 422, 424, 426 or a third-party application 428. The sensor control module 500 may further store this data in encrypted form, such as by using the identifier related to the receiving device 200 or sensor assembly 300, state information, and any other information that is useful for establishing and maintaining a connection with the sensor assembly 300, application 422, 424, 426 or a third-party application 428. This database may be separate from the database accessible by the application 422, 424, 426 or a third-party application 428, despite being an active component (though generally inaccessible) component within the application 422, 424, 426 or a third-party application 428. An application 422, 424, 426 or third-party application 428 can also be deactivated or have its access removed from the sensor data.

The sensor control module 500 as embodied herein can identify the application 422, 424, 426 or third-party application 428 based on tag information. When a particular application 422, 424, 426 or third-party application 428 requests access to the sensor data, the sensor control module 500 may identify the application because the sensor control module 500 may be pre-loaded with tagging information corresponding to the application 422, 424, 426 or third-party application 428.

The current framework and system may be compatible with prior applications developed by the manufacturer of the sensor assembly 300. In particular, logic for converting sensor readings into usable data may be included within the sensor assembly 300 or within the respective application 422, 424, 426. In this manner, the system may take advantage of the framework to integrate prior developed applications into the framework of the system.

The sensor control module 500 also has logic to identify whether the request for sensor data comes from an application 422, 424, 426 or a third-party application 428. The sensor control module may further communicate information regarding a sensor data request to a remote management module 600.

The sensor control module 500 may also have logic to receive information regarding hardware issues with the sensor components of the sensor assembly 300. The sensor control module 500 may send a communication to the application 422, 424, 426 or a third-party application 428 to display a status message about an issue with the sensor assembly 300, such as by alerting the user through the application 422, 424, 426 or a third-party application 428 that a sensor is expiring, has a hardware malfunction, or some other problem that would interfere with providing sensor data related to the analyte being monitored by the sensor assembly 300. The sensor control module 500 may send a communication to the receiving device 200 operating system when the application 422, 424, 426 or third-party application 428 is in the background to display a notification identifying an issue with the sensor assembly 300. These issues may include that a sensor is expiring, has a hardware malfunction, or some other issue that would interfere with providing sensor data relating to the analyte being monitored by the respective sensor assembly 300.

The application 422, 424, 426 or a third-party application 428 may include a user interface (shown further at FIGS. 7A-7C below), including a touch or voice command input, that acts as an interface to receive commands from a user. These commands or input may include a user requesting a sensor reading, visually tapping a display to get sensor data, acknowledging an alarm, or any number of different operations that could be conducted on the display of sensor data.

The sensor control module 500 may be coded in a modular fashion that allows for upgrading the software library 400 to add functionality to communicate with newly developed sensor assemblies. Variables are used in place of hard coded values to enable for modification of the sensor control module 500 to enable communication with newly developed sensor assemblies and to allow applications 422, 424, 426 or a third-party application 428 to get sensor data from those newly developed sensor assemblies without having to submit the underlying application in a new submission or an amended filing for regulatory review and clearance.

Remote Management Module

Figure 6:
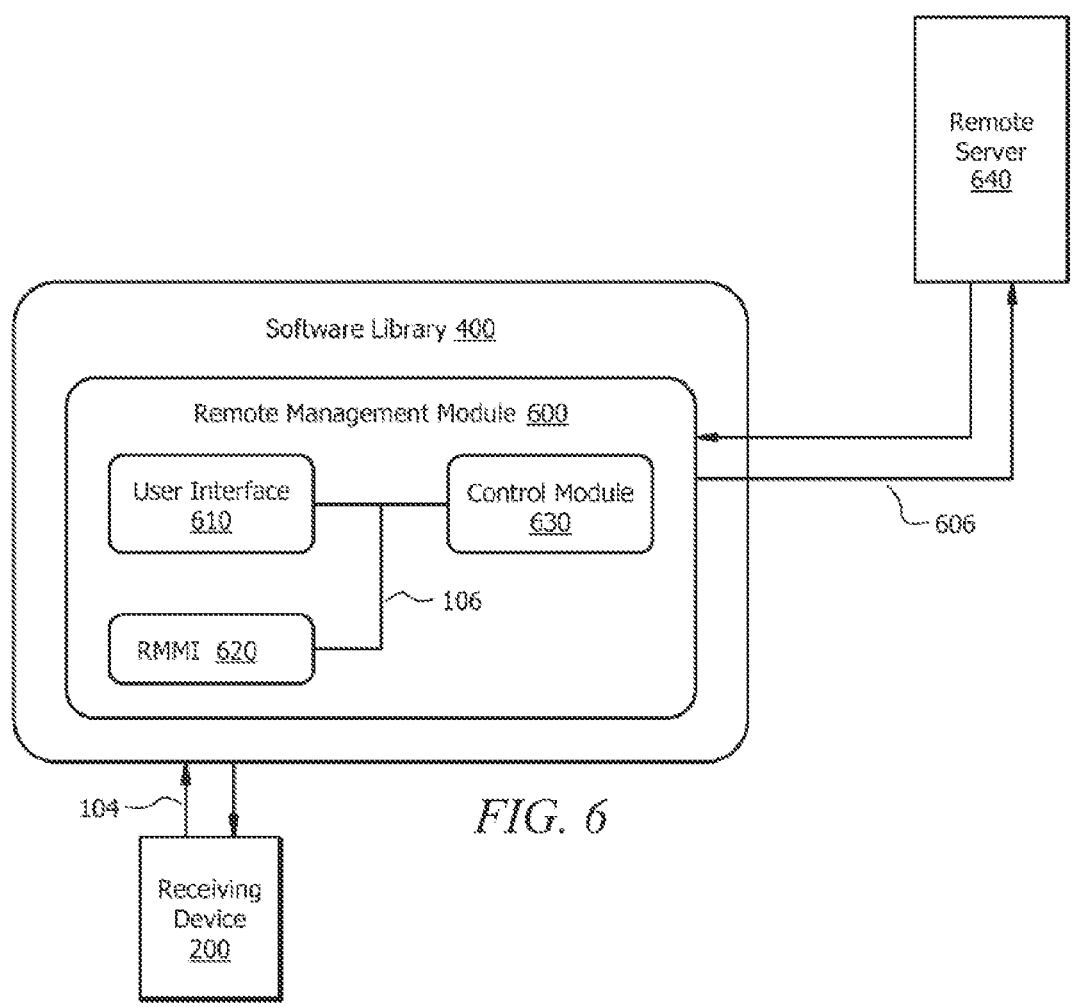
FIG. 6 is a block diagram depicting an example embodiment of the remote management module.

FIG. 6 is a block diagram depicting an example embodiment of the remote management module 600.

The user interface 610 of the remote management module 600 provides functionality for applications 422, 424, 426 or a third-party application 428 to have a consistent interface for certain shared functions. As embodied herein, these features and functions can include activities such as data privacy, user consent, third-party consent, application authorization, and more. The user interface 610 of the remote management module 600 provides a consistent interface to allow various applications 422, 424, 426 or a third-party application 428 access to these functions.

Communication within the remote management module 600 to various software logic can occur using the remote management module messaging channel 106. The user interface 610 also allows for consistent account management capabilities, allowing a user to create an account, set a password, or set profile related information.

The remote management module 600 further includes a remote control module 630 that enables communication to a remote server 640. The communication with the remote server 640 may occur wirelessly using any available communication means, including BLE and NFC communication.

In an embodiment of the system, the remote management module 600 may further provide transport capabilities for enabling a backup of data stored in the various applications 422, 424, 426 or a third-party application 428 in the event a user upgrades the smartphone or receiving device 200. The remote management module 600 may also communicate with the applications 422, 424, 426, or third-party application 428 over a remote management module interface 620.

The software library 400 including the sensor control module 500 and remote management module 600 may include secure coding layers to assist in the prevention of cyber threats, such hacking and remote access. In one example, protection against such threats may include the use of digital certificates or profile provisioning.

A sensor control module 500 can further identify whether the request for sensor data is generated by an application 422, 424, 426 or a third-party application 428. The sensor control module as embodied herein may pass that information to a remote management module 600 through inter-module interface 450, and the remote management module 600 can further customize the user interface 610 for that application 422, 424, 426 or a third-party application 428 using the remote infrastructure. As part of the customized user interface, a custom user authentication interface may be presented to a user of the application 422, 424, 426 or a third-party application 428. The remote management module 600 further includes logic to disable authentication for application 422, 424, 426 or a third-party application 428. In particular, allowing the remote management module 600 to disable access by a third-party application 428 by removing authorization for the third-party application 428 improves monitoring and control over the applications 422, 424, 426 or third-party application 428 that access sensor data.

Applications

Figure 7C:
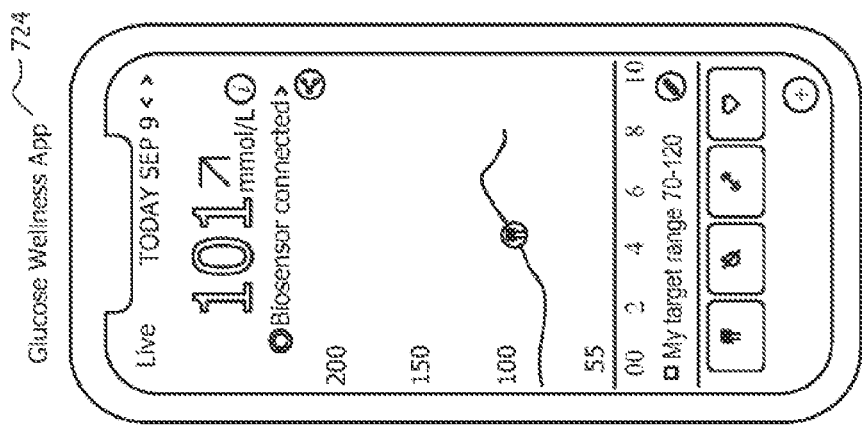
FIG. 7A-7C are exemplary embodiments of user interfaces of applications using the inventive architecture.
Figure 7B:
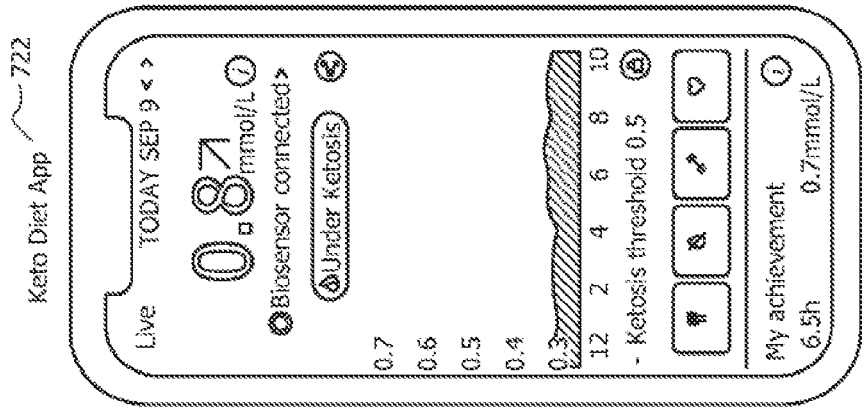
Figure 7A:
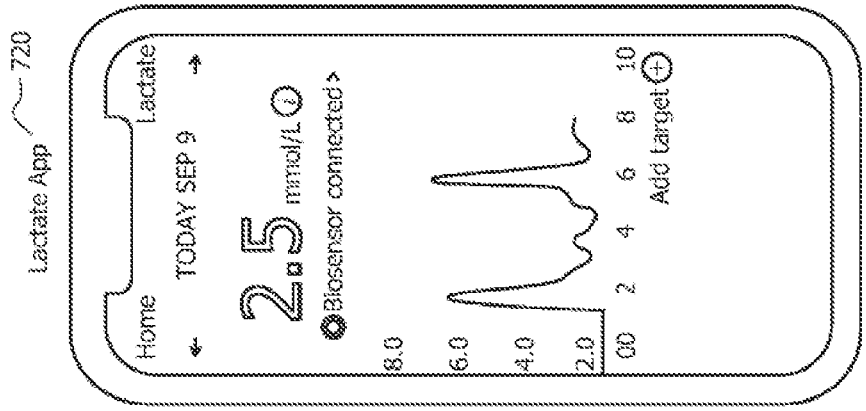

FIG. 7A-7C are exemplary embodiments of applications using the software library 400 and sensor control module 500.

In one example, application 420 may be an application to track analyte values such as lactate as shown in FIG. 7A, ketones or ketone bodies (e.g., β-hydroxybutyrate), such as shown in FIG. 7B, or glucose, as shown in FIG. 7C. Part of the display may come from the sensor control module interface 520 and part may be displayed based on processing within the underlying application 420.

Furthermore, according to some embodiments, applications 720, 722, 724 represent applications 422, 424, 426 to communicate with the sensor control module 500 to enable receipt of sensor data. By using the sensor control module 500 and remote management module 600, a consistent user experience can be provided for the different applications. Moreover, if an additional analyte value needs to be detected and sensed, that application can further integrate the updated software library 400 without having to develop the full architecture for communication, account management, user privacy, and consents.

The improvements to the GUI in the various aspects described and claimed herein produce a technical effect at least in that they assist the user of the device to operate the device more accurately, more efficiently and more safely. It will be appreciated that the information that is provided to the user on the GUI, the order in which that information is provided and the clarity with which that information is structured can have a significant effect on the way the user interacts with the system and the way the system operates. The GUI therefore guides the user in the technical task of operating the system to take the necessary readings and/or obtain information accurately and efficiently.

Biosensor Module Banner

Figure 10A:
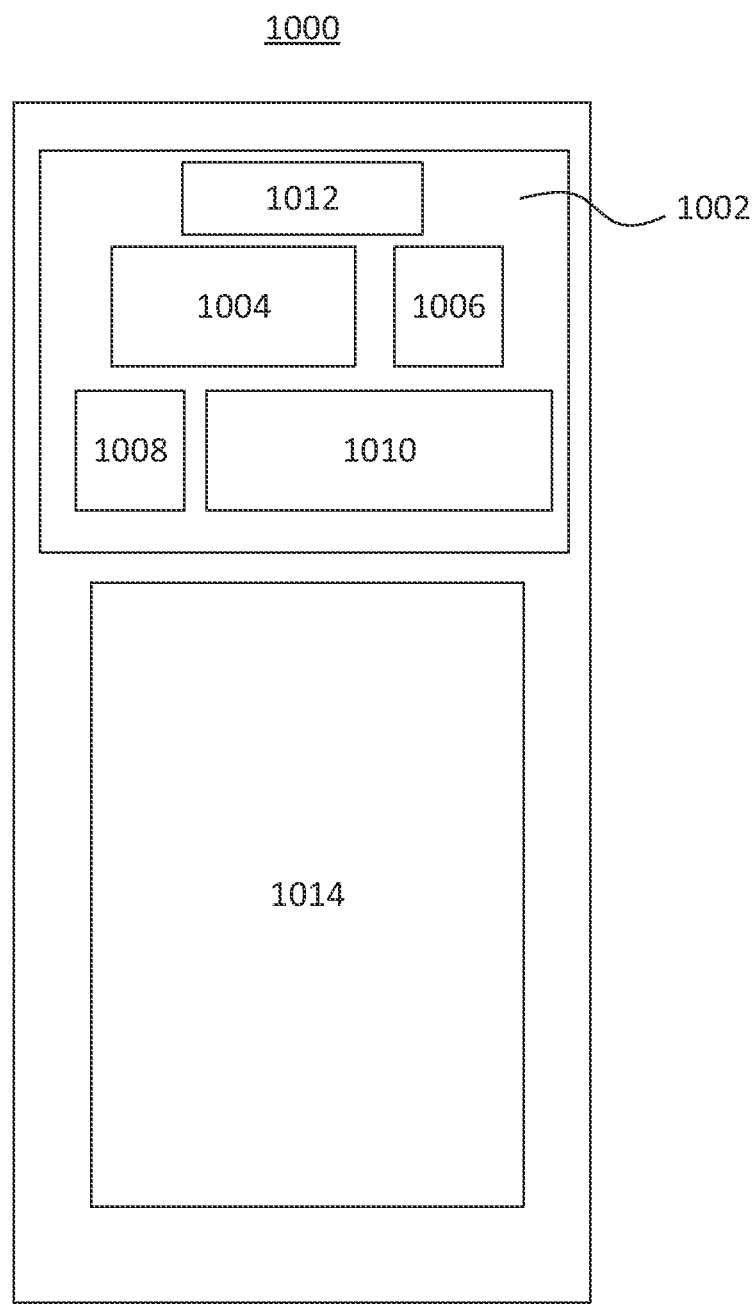
FIGS. 10A-10B are example embodiments of GUIs related to a biosensor banner.

As referenced above, user interface 510 of the sensor control module 500 may include various components. As seen in FIG. 10A, GUI 1000 may include a banner 1002, which is created by the user interface 510, that may be incorporated into GUIs generated by the host application, e.g., applications 422, 424, 426 or third-party application 428. The banner 1002 generated by the user interface 510 may show a different interface depending on the host application into which it is integrated. The banner 1002 may include a real time concentration value 1004, trend information 1006, the status of the biosensor 1008, information 1010 regarding the status of the biosensor, and an additional indication of the biosensor status 1012. In some embodiments, the real-time concentration value 1004 may be updated and/or displayed in 1 minute, or alternatively 5 minute increments. In some embodiments, the trend information 1006 may be a trend arrow. In some embodiments, the status of the biosensor 1008 may be an icon or a text description. The location of the banner 1002 may appear in different parts of the GUI depending on the host application 422, 424, 426 or third-party application 428.

The banner 1002 may be a selectable button. In some embodiments, the banner 1002 may be the only way to initiate biosensor set-up within the host application. Moreover, in some embodiments, the GUIs related to the set-up of the biosensor may only be provided by the biosensor module or approved by the owner of the biosensor module software. In some embodiments, the banner 1002 may be the only way to access GUIs related to the biosensor, including but not limited to biosensor status, errors related to the biosensor, messages concerning the biosensor, and lifetime of the biosensor.

The banner 1002, or elements within the banner 1002, may be selectable, or the whole banner may be a selectable button, to link to other GUIs with additional information about the biosensor. For example, where the host application is a glucose wellness application, the banner 1002 may include a real time concentration value 1004, a status icon 1008, and information status 1010 about the biosensor. Moreover, the real time concentration value 1004 may be located in a different part of the GUI (e.g., as part of an analyte graph) than the rest of the banner. As another example, where the host application is an application that monitors ketone levels in association with, e.g., a ketogenesis diet, the banner may include a real time concentration value 1004 of ketones reported in mmol/L, a trend arrow 1006, a status icon 1008, information status 1010 about the biosensor, and the additional indication of the biosensor status 1012 (e.g., "Biosensor ready").

Various different status icons 1008 and information regarding the status of the biosensor 1010 may be displayed. In some embodiments, a status icon 1008 including a circle of dots, which may or may not be animated, may appear next to status information 1010 indicating that the biosensor is not connected or ready. In some embodiments, the status icon 1008 may include a triangle with an explanation point or a question mark to indicate that there is a sensor error or that the sensor is searching for signal. For example, the status information 1010 may state that the biosensor will be ready in a certain amount of time, e.g., "Ready in 30 mins" or "Getting Ready." In some embodiments, the status information 1010 may state "Searching," which may indicate that the application is trying to connect to the biosensor. The status information may also state whether or not the sensor is connected, whether the sensor wear period has expired, whether the sensor is too hot, or whether the sensor is too cold. The status icon may also be a circle, which may be animated, and may appear next to status information 1010 indicating that the biosensor is "Live." The circle may be animated such that for a biosensor with a total life of X days, where the biosensor has Y days of life remaining, then the color indicator around the circumference will be a different color, e.g., blue, for Y/X*100 of the circumference of the circular graphic. For example, for a biosensor with a total life of 14 days, where the biosensor has 12 days of life remaining, then the color indicator around the circumference will be blue for approx. 85.7% of the circumference of the circle. The color of the status icon may be different depending on the amount of time left in the biosensor life. The color of the status icon may be a first color, e.g., blue, when at least 50%, alternatively at least 40%, alternatively at least 30%, alternatively at least 25%, alternatively at least 20% of the biosensor life remains. The color of the status icon may change to a second color, e.g., orange, when less than 50%, alternatively less than 40%, alternatively less than 30%, alternatively less than 25%, alternatively less than 20% of the biosensor life remains. In some embodiments, the color of the status icon may change to a third color, e.g., red, when less than 25%, alternatively less than 20%, alternatively less than 10%, alternatively less than 5% of the biosensor life remains.

In some embodiments, the biosensor status may also state "SEE DETAILS," which may indicate an issue with the biosensor. In some embodiments, the biosensor status may also state "START NEW SESSION," which may indicate an issue with the biosensor or that the previous biosensor has ended. After tapping or selecting "PAIR," a pop-up window may appear that instructs the user to hold the reader device (e.g., mobile phone) very close to the biosensor. The phone may vibrate after successfully scanning the biosensor.

Figure 10B:
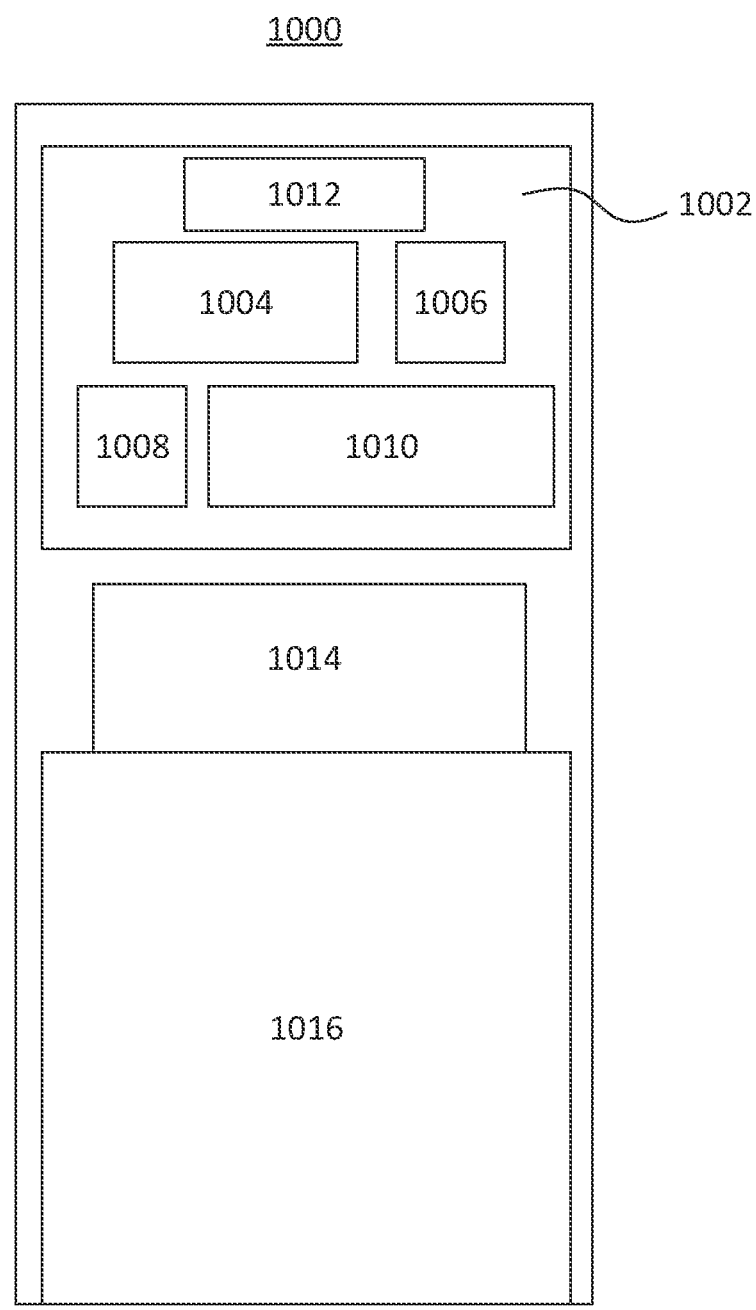

In some embodiments, as seen in FIG. 10B, a pop-up screen 1016 may also appear over GUI 1000. The pop-up screen 1016 may convey a message regarding the biosensor starting up. The pop-up screen 1016 may indicate the amount of time in, e.g., hours and/or minutes, remaining until the biosensor is ready. For example, the pop-up screen may indicate that the "Biosensor is ready in 55 minutes." In other embodiments, if the reader device, such as a smart phone, is locked, a notification may appear on the lockscreen indicating that the biosensor is ready.

In some embodiments, the banner 1002 is the primary display of the status of the biosensor. In some embodiments, the banner 1002 is the only display of the status of the biosensor in the host application. The banner may display errors and the life count of the biosensor. As seen in FIG. 10A, in some embodiments, a status icon 1008 including a circle with a color progress indicator may appear next to status information 1010 stating that the biosensor is connected and working properly. For example, the status information 1010 may say "LIVE." In some embodiments, for the status icon 1008 of the circle with the progress indicator, the progress indicator may be colored, and the color may be proportional to the amount of sensor life remaining for the current biosensor. In some embodiments, the color of the progress indicator may be different colors depending on how much sensor life is remaining. For example, the color indicator may be a blue color if at least about 50%, alternatively at least about 40%, alternatively at least about 30%, alternatively at least about 25%, alternatively at least about 20%, alternatively at least about 10% of the sensor life remains. In some embodiments, the colored progress indicator may be a different color, e.g., orange or red, if the sensor life remaining is less than a certain amount. For example, the color indicator may be an orange color if less than about 50%, alternatively less than about 40%, alternatively less than about 30%, alternatively less than about 20%, alternatively less than about 10%, alternatively less than about 5% of the sensor life remaining.

In some embodiments, the status information 1010 may state "SEE DETAILS" or similar language to indicate that the user should learn more about the status of the biosensor. By selecting on the "SEE DETAILS" or other parts of the banner, one of many explanations, may be displayed to indicate a possible error or issue with the biosensor. In some embodiments, where there is an issue with the biosensor and the status information 1010 states "SEE DETAILS," a real time concentration value 1004 may not be displayed. In lieu of the real time concentration value 1004, in some embodiments, a plurality of dashes or dots (e.g., two dashes) may appear instead of the concentration value 1004 of the analyte measured by the biosensor.

In some embodiments, the banner 1002 may include a real time concentration value 1004, an icon 1008 indicating the status of the biosensor, and information 1010 regarding the status of the biosensor. A GUI may have the real time analyte concentration value 1004 located in a different part of the GUI than the other components of the banner 1002. For example, the real time analyte concentration value 1004 may be located in a graph that is part of the GUI generated by the host application. The graph may include an analyte curve and a marker for the current analyte concentration, and the real time analyte concentration value may be located above the marker. In other embodiments, the real time analyte concentration value may be located in a sentence or statement about the user's analyte concentration. For instance, the sentence or statement may be located above the graph.

In some embodiments, the banner 1002 may include a real time concentration value 1004, an icon 1008 indicating the status of the biosensor, and information 1010 regarding the status of the biosensor. The real time analyte concentration value may be located in a graphic element provided by the host application. The graphic element may be a colored circle or other shape. If the analyte level is within a target range, as explained elsewhere in this application, the graphic element may be colored a first color (e.g., green). If the analyte level is outside of a target range, the graphic element may be colored a second color (e.g., orange). The color of the graphic element may be the same color as the analyte curve in the analyte graph.

In some embodiments, the banner 1002 may be the only visual display of real-time biosensor values, i.e., real-time analyte levels, in the host application. The real-time analyte levels may be displayed or updated every minute, alternatively every 2 minutes, alternatively every 5 minutes, alternatively every 30 seconds. In some embodiments, the banner 1002 may only be or must be located in the host application GUI where real-time analyte values are shown. In some embodiments, the banner 1002 may only be or must be located where values or calculations are displayed and updated in real time.

Set-Up

After initiation of the set-up, a series of GUIs may be presented to assist the user in applying the biosensor to their skin surface and to pair the biosensor with the application. In some embodiments, the set-up GUIs may only be initiated by selecting the banner. In other embodiments, the set-up GUIs may be opened thorough a set-up button or settings link or button.

The application may present numerous GUIs that describe how to apply the biosensor. A GUI may be presented that shows what is included in the box. In addition to a picture, it may also explain that the user may find a biosensor pack and a biosensor applicator in the box. Another GUI may appear that instructs the user to choose a site on the back of their upper arm away from scars, moles, stretch marks, or lumps, and may be accompanied by a picture highlighting a section of a person's upper arm where it would be appropriate to apply the biosensor. An additional GUI may be provided that instructs the user to clean the selected site by washing the site using plain soap, cleaning the site with an alcohol wipe, and then allowing the site to dry.

The application may provide a GUI that explains how to prepare the biosensor pack and applicator. In addition to a picture showing how to open the pack, the GUI may contain written instructions to peel the lid completely off of the biosensor pack and to unscrew the cap from the biosensor applicator. The application may then provide a GUI that includes a picture of a person loading the biosensor in the applicator along with instructions that state to line up the dark marks on the biosensor applicator and the biosensor pack. On a flat, hard surface, press down firmly on the biosensor applicator until it comes to a stop. The application may then provide another GUI that instructs the user to lift the biosensor applicator out of the biosensor pack and informs the user that the biosensor applicator is ready to apply the biosensor. The GUI may include a warning that the biosensor applicator now contains a needle and that the user should not touch inside the biosensor applicator or put it back into the biosensor pack.

Figure 23A:
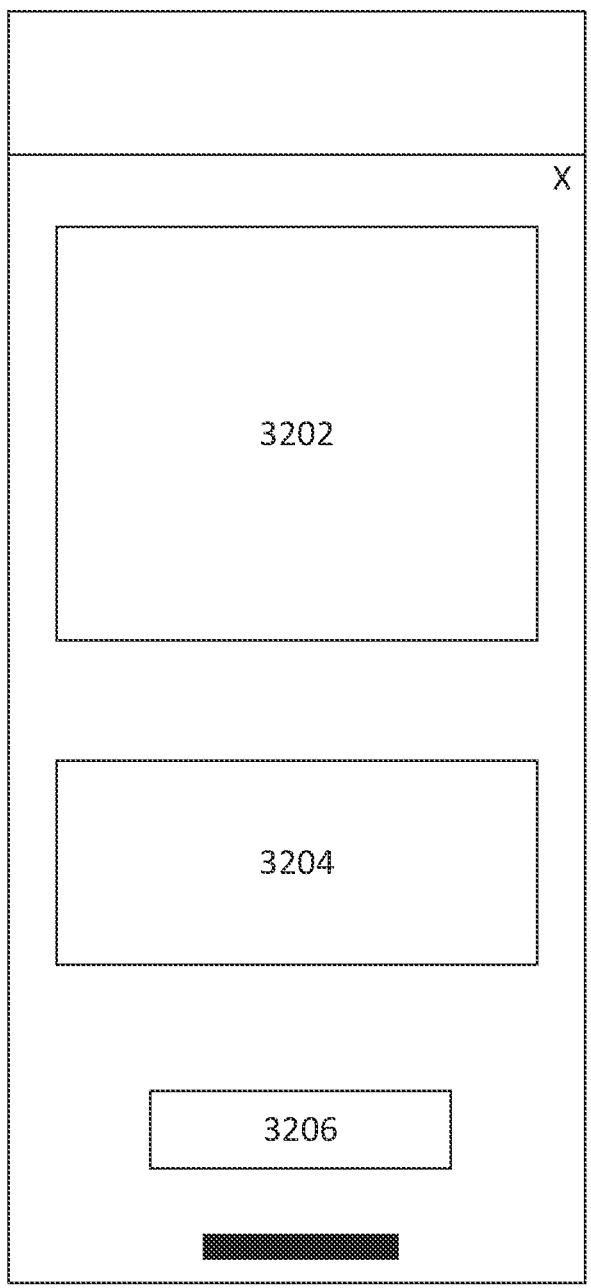
FIGS. 23A-23D are block diagrams depicting example embodiments of GUIs related to pairing a biosensor with a reader device.

The application may then provide GUIs describing how to apply the biosensor to the user's body. As seen in GUI 3200 in FIG. 23A, an introductory GUI 3200 may include a graphic 3202 of a biosensor, along with introductory text 3204 inviting the user to begin the setup to pair their biosensor. The user may then tap or select a start setup button 3206 to begin the setup process.

Figure 23B:
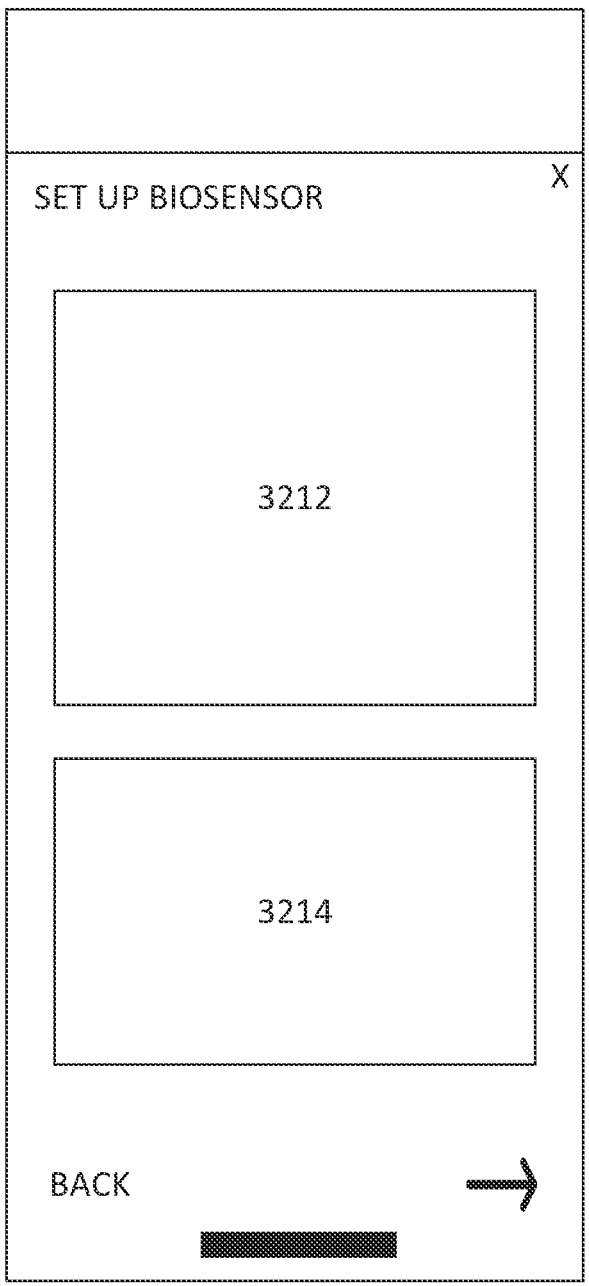

As seen in GUI 3210 of FIG. 23B, a Set Up Biosensor GUI 3210 may include a graphic or picture 3212 showing a person applying an applicator to their body at, e.g., the back of their upper arm. The GUI 3210 may also include text 3214 explaining how to apply the biosensor. The text 3214 may instruct the user to place the biosensor applicator over a site and push down firmly to apply the biosensor. The text 3214 may then instruct the user to gently pull the biosensor applicator away from their body. The text 324 may also caution the user not to push down on the biosensor applicator until it is placed over the prepared site to prevent unintended results or injury. The user may then tap the arrow button to proceed to GUI 3220 after the biosensor has been applied.

The application may also present a GUI instructing the user to check the biosensor to make sure that the biosensor is secure by pressing down on the adhesive.

Figure 23C:
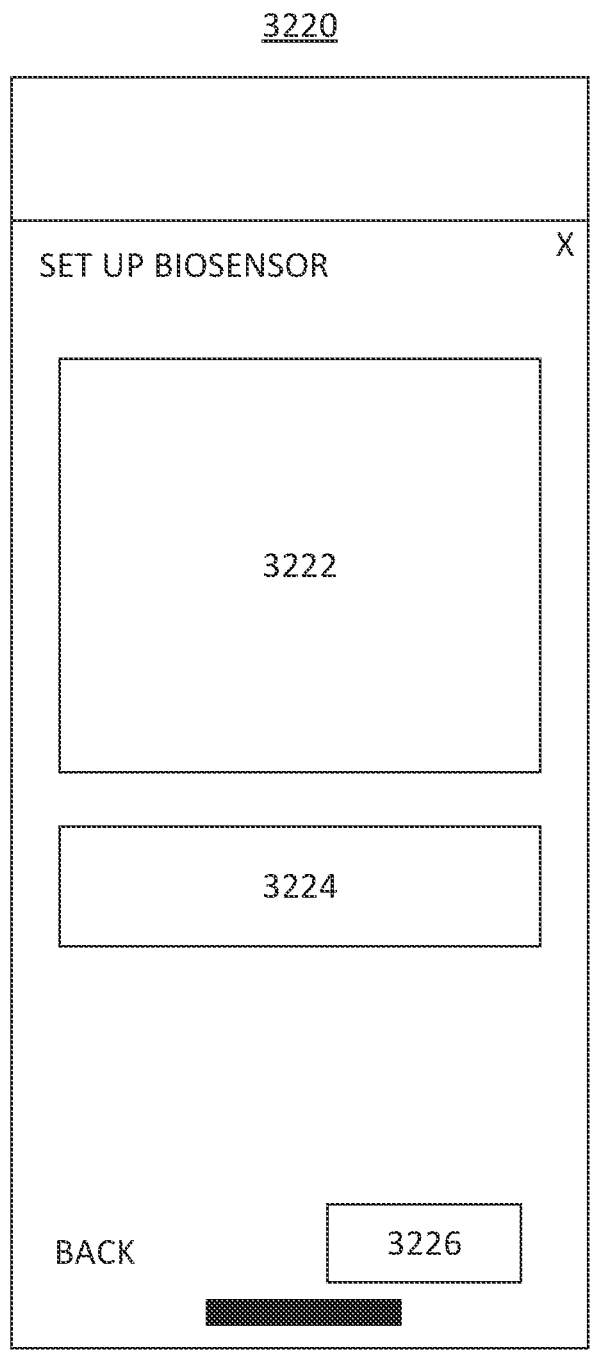

As seen in GUI 3220 of FIG. 23C, in another Set Up Biosensor GUI 3220, a graphic or picture 3222 may show a person pairing the biosensor to the reader device, such as a smart phone, by holding the reader device in close proximity to the applied biosensor. The text 3224 may instruct the user to pair their biosensor by tapping the start pairing button 3226. A pop-up window may appear that instructs the user to hold the reader device (e.g., mobile phone) very close to the biosensor. The phone may vibrate after successfully scanning the biosensor.

Figure 13A:
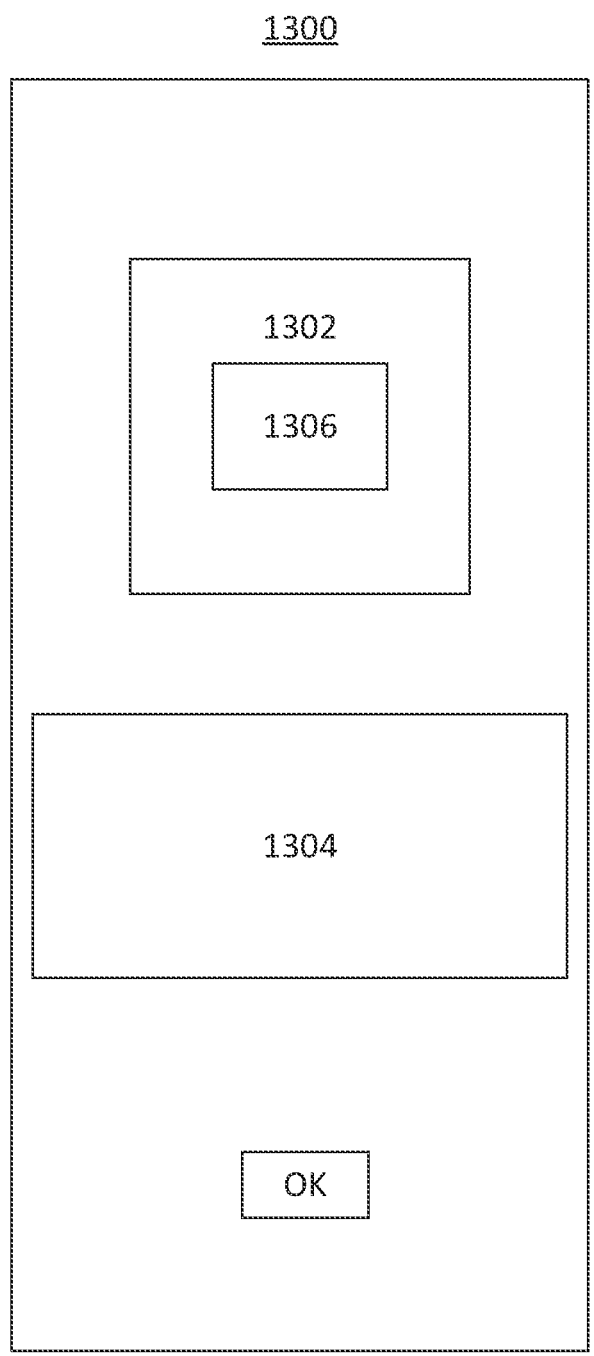
FIG. 13A is a block diagram depicting an example embodiment of a GUI related to setup of the biosensor.
Figure 13B:
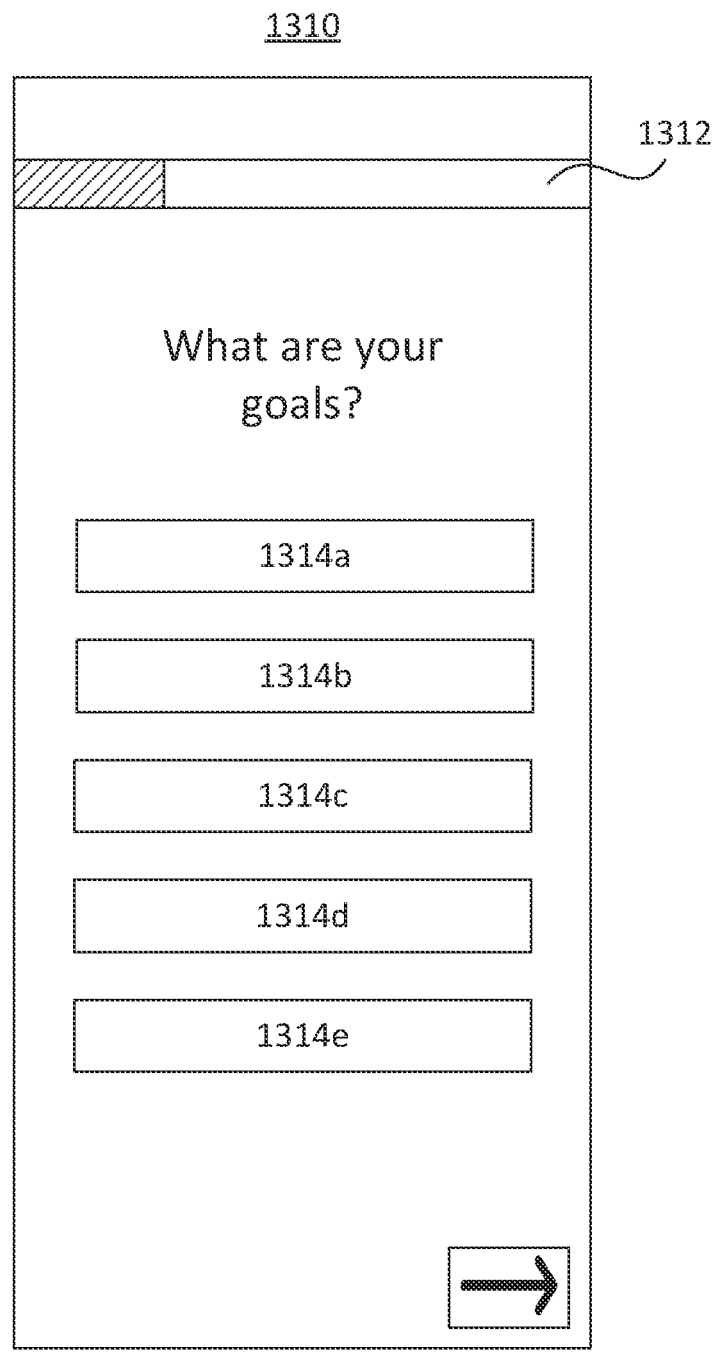
FIG. 13B is a block diagram depicting an example embodiment of a GUI related to receiving the goals that the user wishes to achieve.
Figure 13C:
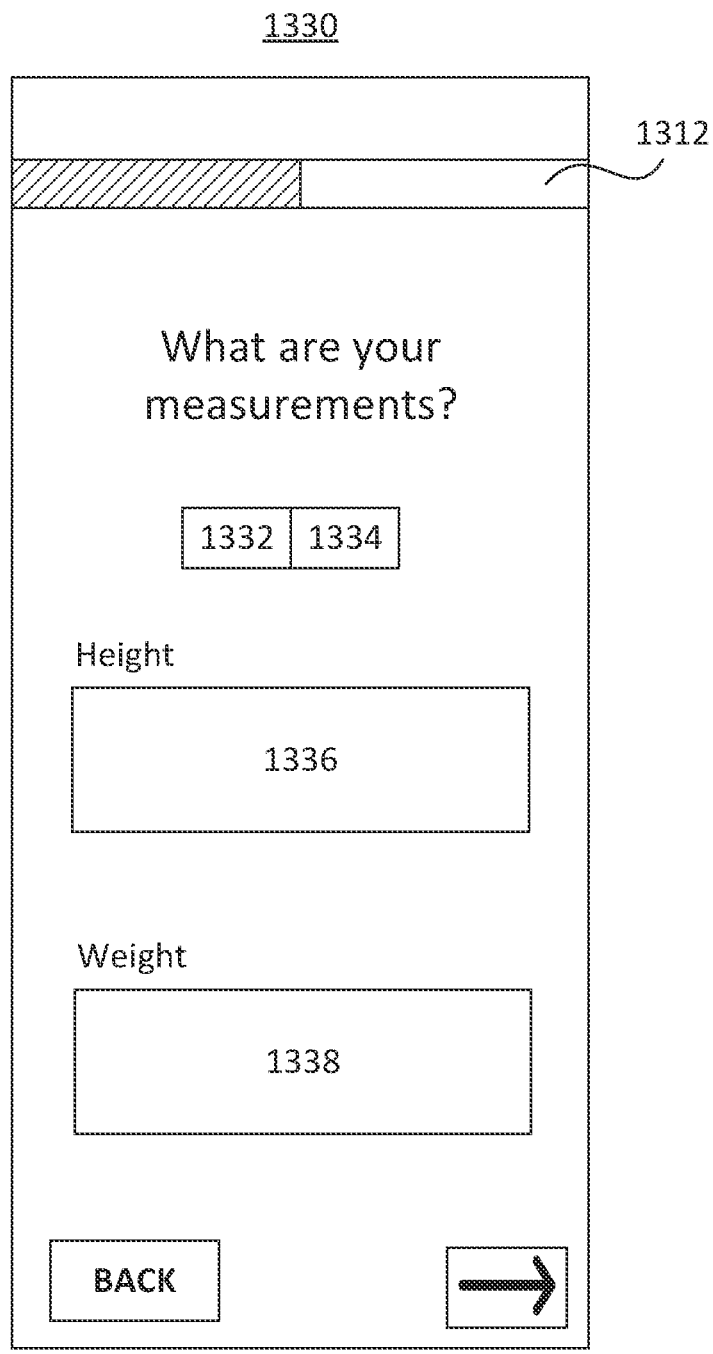
FIG. 13C is a block diagram depicting an example embodiment of a GUI related to receiving the user's measurements.
Figure 13D:
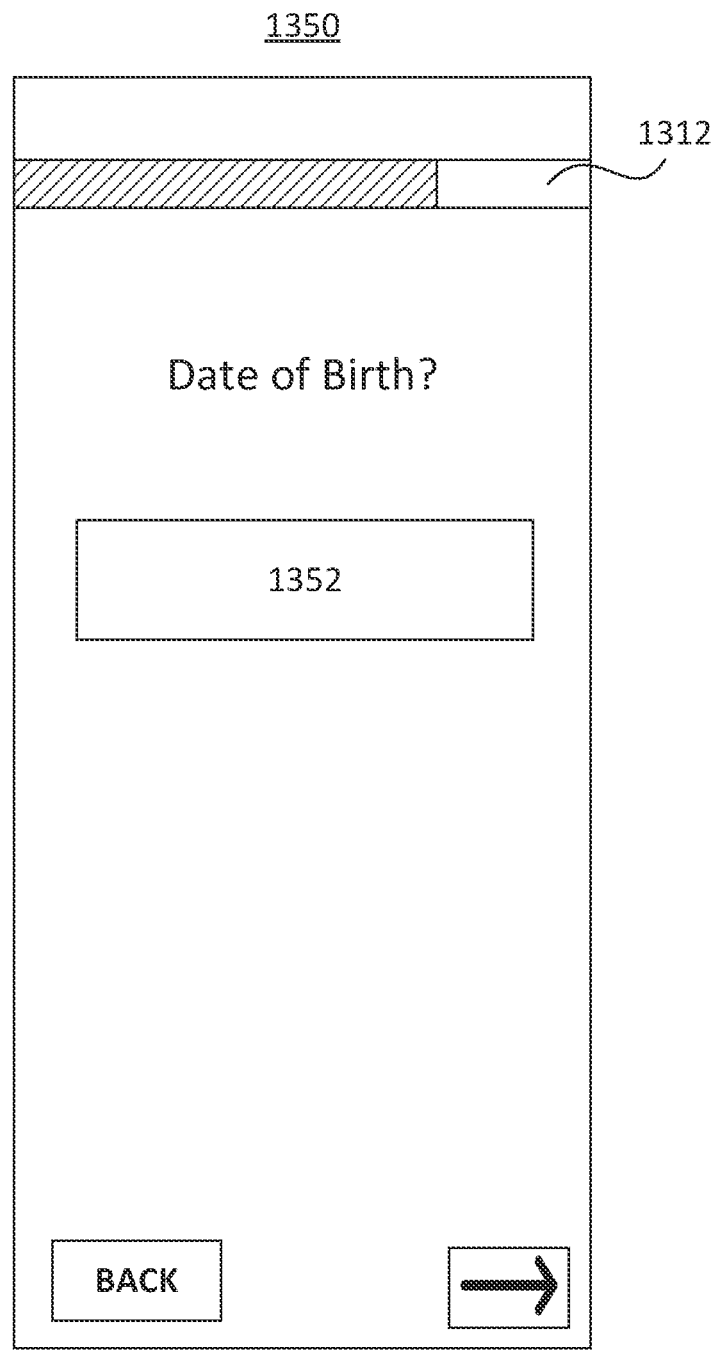
FIG. 13D is a block diagram depicting an example embodiment of a GUI related to receiving the user's birth date.
Figure 23D:
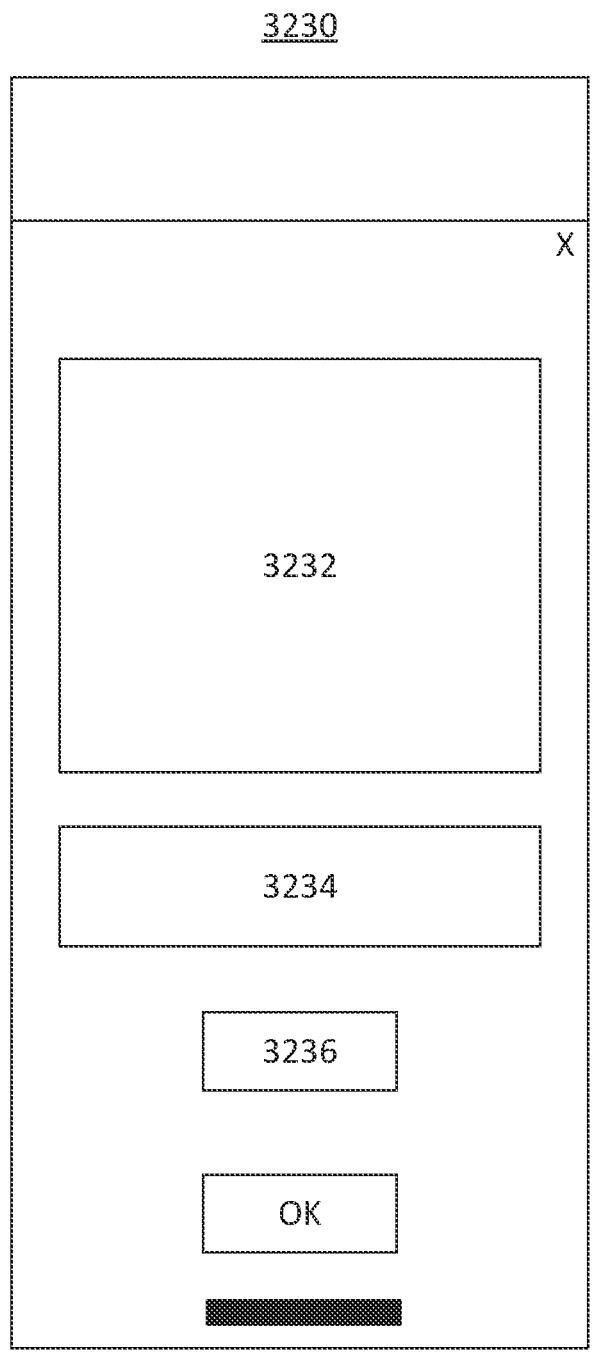

After the biosensor has been paired, as seen in FIG. 23D, as also described with respect to FIG. 13D, GUI 3230 may be displayed, which indicates the time remaining for the biosensor to be ready. The GUI 3230 may include a graphic 3232 highlighting the time remaining until the biosensor is active. The graphic 3232 may include a radiating circle of dots, which may be animated. Alternatively, the graphic 3232 may include a progress indicator that may be a bar having a colored portion or may be a colored portion along the perimeter of a circle, where the colored portion is proportional to the amount of time remaining before the sensor is active, e.g., a total perimeter of a circle may be equivalent to 60 minutes and a colored portion of the perimeter may be proportional to the amount of time remaining under an hour for the biosensor to be active. Alternatively, the graphic 3232 may be animated and the color of the perimeter of the circle may change as the time remaining is counting down. The GUI 3230 may also include a display 3236 of the number of minutes until the biosensor is active (e.g., "55:10" where 55 minutes and 10 seconds remain until the sensor is ready or active). Alternatively, in some embodiments, a message of "Ready in 55 mins" may be displayed on the inside of a circle or below the graphic 3236, where a colored portion of the perimeter of the circle is animated and cyclically changes color as the time remaining until the biosensor is active counts down. The GUI may also include a plurality of selectable links that, when selected by the user, can display additional information to the user as explained elsewhere, including how to replace a biosensor, support, learning more about the application, and ordering a biosensor.

The GUI 3230 may also include a description or message 3234 that informs the user that their biosensor is now getting to know them, and real-time analyte levels will be available in the amount of time displayed in 3236. In some embodiments, elements of GUI 3230 may be provided by the biosensor module. For example, the graphic having a progress indicator 3232 and the display 3236 of the amount of time until the biosensor is active may be provided by the biosensor module. After the user clicks OK, the GUI 3230 may collapse and the home screen with the banner may then be visible to the user. As seen in FIG. 10A, the banner 1002 may display an icon 1008 indicating the status of the biosensor along with information 1010 regarding the status of the biosensor. In some embodiments, similar to the progress indicator described with respect to graphic 3232, the icon 1008 may also include a progress indicator that indicates the time remaining for the biosensor to be ready. The icon 1008 may include a graphic highlighting the time remaining until the biosensor is active. The graphic may include a radiating circle of dots, which may be animated. The icon 1008 may include a progress indicator that may be a bar having a colored portion or may be a colored portion along the perimeter of a circle, where the colored portion is proportional to the amount of time remaining before the sensor is active, e.g., a total perimeter of a circle may be equivalent to 60 minutes and a colored portion of the perimeter may be proportional to the amount of time remaining under an hour for the biosensor to be active. The information 1010 may include text indicating that the biosensor is "READY IN XX," wherein XX may be displayed in minutes and seconds. For example, the banner 1002 may display "READY IN 55:10" where the biosensor will be active in 55 minutes and 10 seconds.

System Messages

If there is an issue with the biosensor, a system message may appear regarding the status of the biosensor. The system message may appear in a pop-up window or alert. Alternatively, in some embodiments, the system message may appear after the user selects "SEE DETAILS."

In some embodiments, the details message 1210 may include a "Pairing Error" message that may state that the pairing was unsuccessful. Moreover, the ketone application may suggest trying to pair the biosensor again.

Figure 12A:
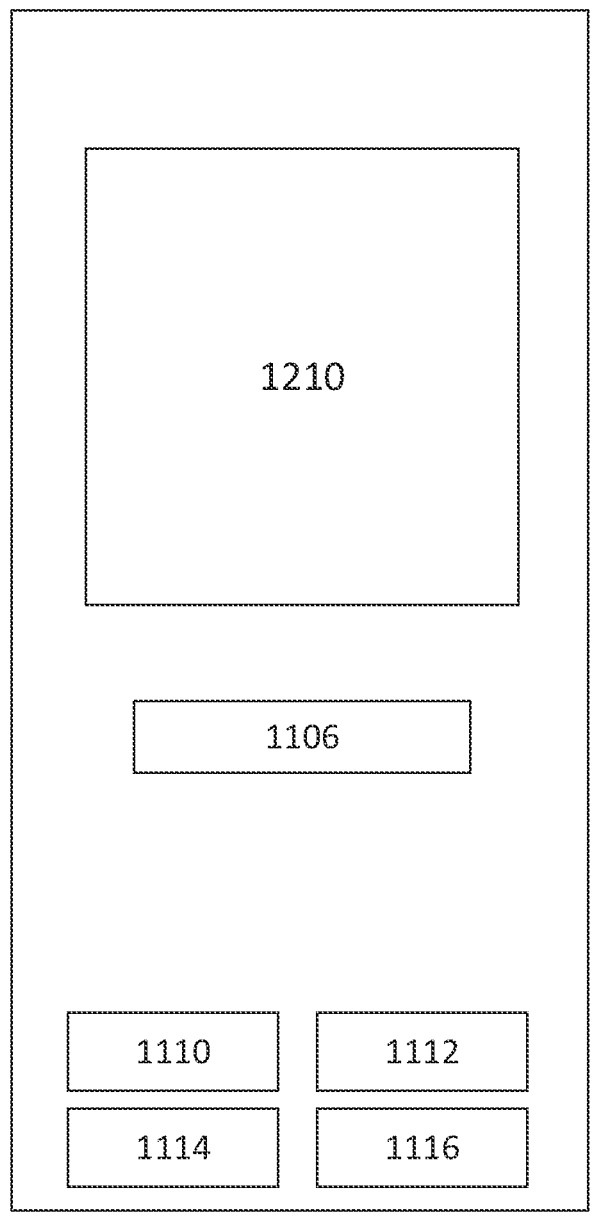
FIGS. 12A-12B are example embodiments of GUIs related to system messages associated with a biosensor.

After a user selects "SEE DETAILS," as seen in FIG. 12A, user interface 510 of the sensor control module 500 can be configured to display one of a plurality of messages in a GUI 1200 that may include a details message 1210, the serial number of the current biosensor 1106, and a plurality of selectable links 1110, 1112, 1114, 1116 that, when selected by the user, can display additional information to the user as explained elsewhere, including how to replace a biosensor, support, learning more about the application, learning more about the sensor, etc. In some embodiments, the details message 1210 may be presented in a circular graphic that includes a progress indicator to visually illustrate the remaining life of the current biosensor. As explained with respect to other embodiments, the graphic may be a circle and the progress indicator may be a different color perimeter of the circle, where the progress indicator may be proportional to the amount of sensor life remaining for the current biosensor. And as explained with respect to other embodiments, the color of the progress indicator may be different colors depending on how much sensor life is remaining.

In some embodiments, the banner 1002 may display a plurality of dashes or dots (e.g., two dashes) instead of the concentration value or level 1004 of the analyte measured by the biosensor when there is an issue with the biosensor. If the user taps on the banner 1002 when the banner is not displaying a real-time analyte concentration or level, e.g., displaying plurality of dashes or dots, then one of a plurality of system messages regarding problems with the biosensor may be displayed. When the user taps or selects the banner, a details message GUI may appear that gives additional details about the biosensor status.

In some embodiments, the details message 1210 may include a "Check Biosensor" message that may state that it looks like the user's biosensor is not applied correctly. The details message 1210 may also include further instructions indicating if the biosensor is not attached firmly to the user's skin, then the user should apply a new biosensor and pair it. The details message 1210 may also include further instructions indicating if the biosensor is applied properly, then the user should try pairing the biosensor again. The details message 1210 may optionally also include a selectable "Pair" or "Pair Biosensor" button that, when selected, would display a GUI that assists the user to begin the pairing process.

In some embodiments, the details message 1210 may include a "Signal Loss" message that may caution the user to keep their phone in range of the biosensor at all times. The details message 1210 may further instruct that if the user continues having issues, then they should turn their phone's BLUETOOTH® off and on, or restart their phone.

In some embodiments, the details message 1210 may relate to the temperature of the biosensor. In some embodiments, the details message 1210 may include a "Biosensor Too Hot" message that may inform the user that the biosensor is too hot to give readings. The details message 1210 may further request that the user check again in a few minutes. In some embodiments, the details message 1210 may include a "Biosensor Too Cold" message that may inform the user that the biosensor is too cold to give readings. The details message 1210 may further request that the user check again in a few minutes.

In some embodiments, the details message 1210 may include a "Biosensor Error" message that may inform the user that a biosensor reading is unavailable. The details message 1210 may further request that the user check again in a certain time period, e.g., 5 minutes, alternatively 10 minutes, alternatively 30 minutes.

In some embodiments, when the signal from the biosensor is suddenly lost, the biosensor status may change immediately to "SEARCHING". When the "searching" description is selected or tapped, a details message 1210 may appear that suggests that the user keep their phone in range of the biosensor at all times. If the user continues having issues, the application suggests that the user turn the phone's BLU-ETOOTH® off and on, or restart the phone.

In some embodiments, the details message 1210 may include a "Biosensor Incompatible" message that may inform the user that the biosensor cannot be used with this version of the application. The message may suggest removing the biosensor and pairing a new one.

In some embodiments, the details message 1210 may include a "Biosensor Ended" message that may inform the user that the biosensor has ended and instruct the user to pair a new biosensor.

In some embodiments, the details message 1210 may include a "Biosensor already in use" message that may inform the user that a biosensor has already been paired and cannot be used. The message may also instruct the user to remove the biosensor and pair a new one.

In some embodiments, the details message 1210 may include a "Current Biosensor" message, which may be in a different color than messages indicating problems or errors. The message may indicate that the biosensor that the user tried to pair is in use and that the user will automatically receive real-time ketone readings directly to their device. The message may also include a different icon, such as a check mark.

In some embodiments, the details message 1210 may include an "ENABLE BLUETOOTH®" message that requests the user to please turn on BLUETOOTH®. The details message 1210 may further explain that BLU-ETOOTH® is required to receive biosensor readings.

In some embodiments, the details message 1210 may include a "Replace Biosensor" or "Start a New Biosensor" message that may inform the user that the biosensor is not working. The details message 1210 may further request that the user please remove or replace the biosensor and pair a new one.

Figure 12B:
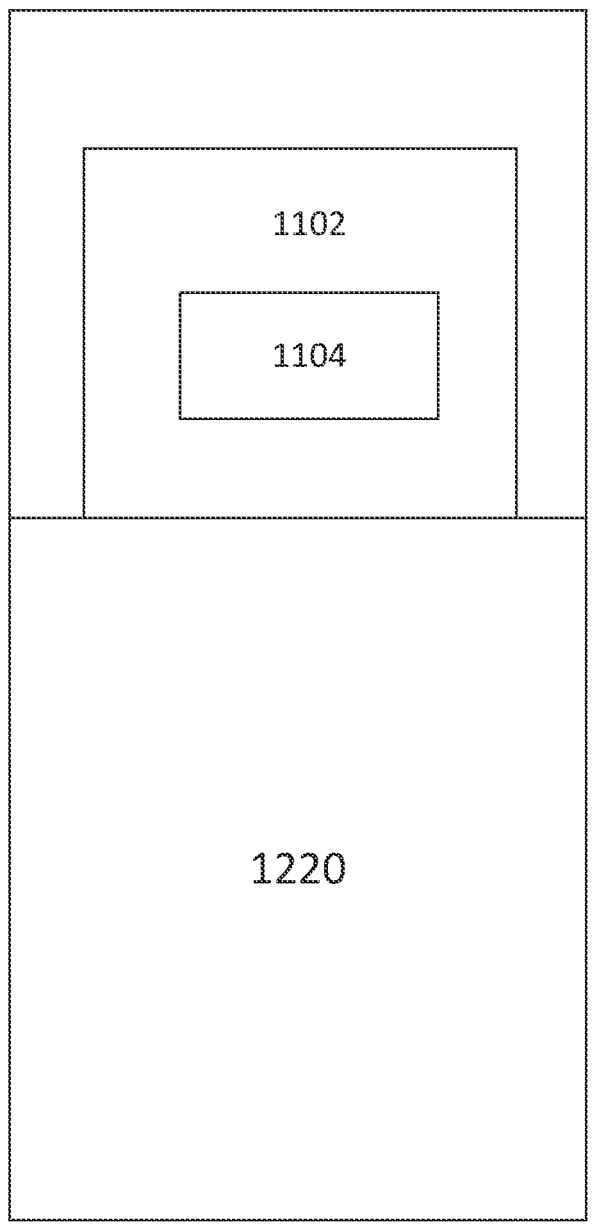

As seen in FIG. 12B, a pop-up window 1220 may also appear, which may include a details message. The contents of the details message in pop-up window 1220 may be the same or substantially the same as described with respect to the plurality of details message 1210 described above that my appear in GUI 1200.

The biosensor module may also create and store an error log.

Biosensor Module Details GUI

Figure 11A:
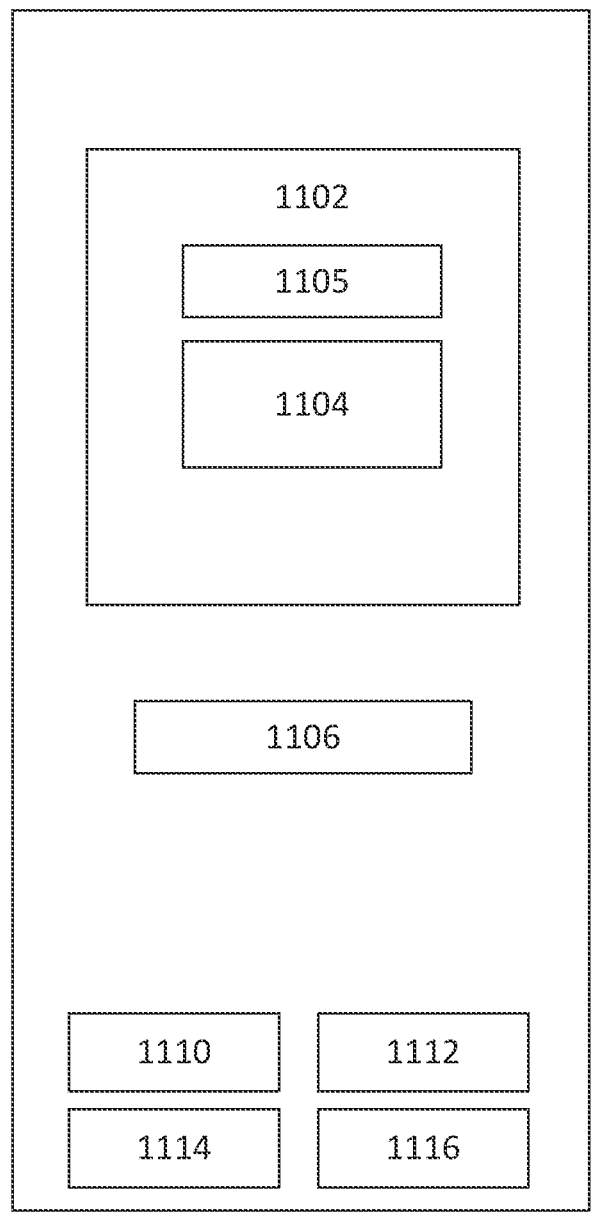
FIGS. 11A-11B are example embodiments of GUIs related to a biosensor module details.

If the user selects or clicks the banner 1002, or selects or clicks any of the elements of the banner 1002, user interface 510 of sensor control module 500 can be configured to output a biosensor module details GUI 1100, as seen in FIG. 11A. The biosensor module details GUI 1100 may include a biosensor status details explanation, an indication of the biosensor life (e.g., remaining life of the biosensor), a biosensor identification, a link to settings, and a link to biosensor labeling and support information. The biosensor module details GUI 1100 may include a graphic 1102 that includes a progress indicator to visually illustrate the remaining life of the current biosensor. In some embodiments, the graphic 1102 may be a circle and the progress indicator may be a different color perimeter of the circle, where the progress indicator may be proportional to the amount of sensor life remaining for the current biosensor. For example, for a biosensor with a total life of X days, where the biosensor has Y days of life remaining, then the color indicator around the circumference will be a different color, e.g., blue, for Y/X*100 of the circumference of the circular graphic 1102. For example, for a biosensor with a total life of 14 days, where the biosensor has 12 days of life remaining, then the color indicator around the circumference will be blue for approx. 85.7% of the circumference of the circle 1102.

In some embodiments, the color of the progress indicator may be different colors depending on how much sensor life is remaining. For example, the color indicator may be a blue color if at least about 50%, alternatively at least about 40%, alternatively at least about 30%, alternatively at least about 25%, alternatively at least about 20%, alternatively at least about 10% of the sensor life remains. In some embodiments, the colored progress indicator may be a different color, e.g., orange or red, if the sensor life remaining is less than a certain amount. For example, the color indicator may be an orange color if less than about 50%, alternatively less than about 40%, alternatively less than about 30%, alternatively less than about 20%, alternatively less than about 10%, alternatively less than about 5% of the sensor life remaining.

The GUI 1100 may also include a real time indicator of amount of time remaining of the biosensor life 1104. For instance, the real time indicator may state "12 days" in the middle of the circular graphic 1102, in the example above. The real time indicator 1104 may be proportional to the progress indicator of the graphic 1102. The real time indicator 1104 may indicate the amount of time remaining of the biosensor life as a number of days when the amount of time remaining is greater than about 1 day, alternatively greater than about 23 hours and 59 minutes. The real time indicator 1104 may indicate the amount of time remaining as a number of hours when the amount of time remaining of the biosensor life is less than about 24 hours. In some embodiments, when the amount of time remaining of the biosensor life is less than about 24 hours, then the progress indicator may switch to a different color, e.g., the color may change from blue or green or orange or red. The real time indicator 1104 may indicate the amount of time remaining as a number of minutes when the amount of time remaining of the biosensor life is less than about 1 hour or less than about 61 minutes. The GUI may also include an additional message 1105 stating that the Biosensor Life is "Ending Soon."

Figure 11B:
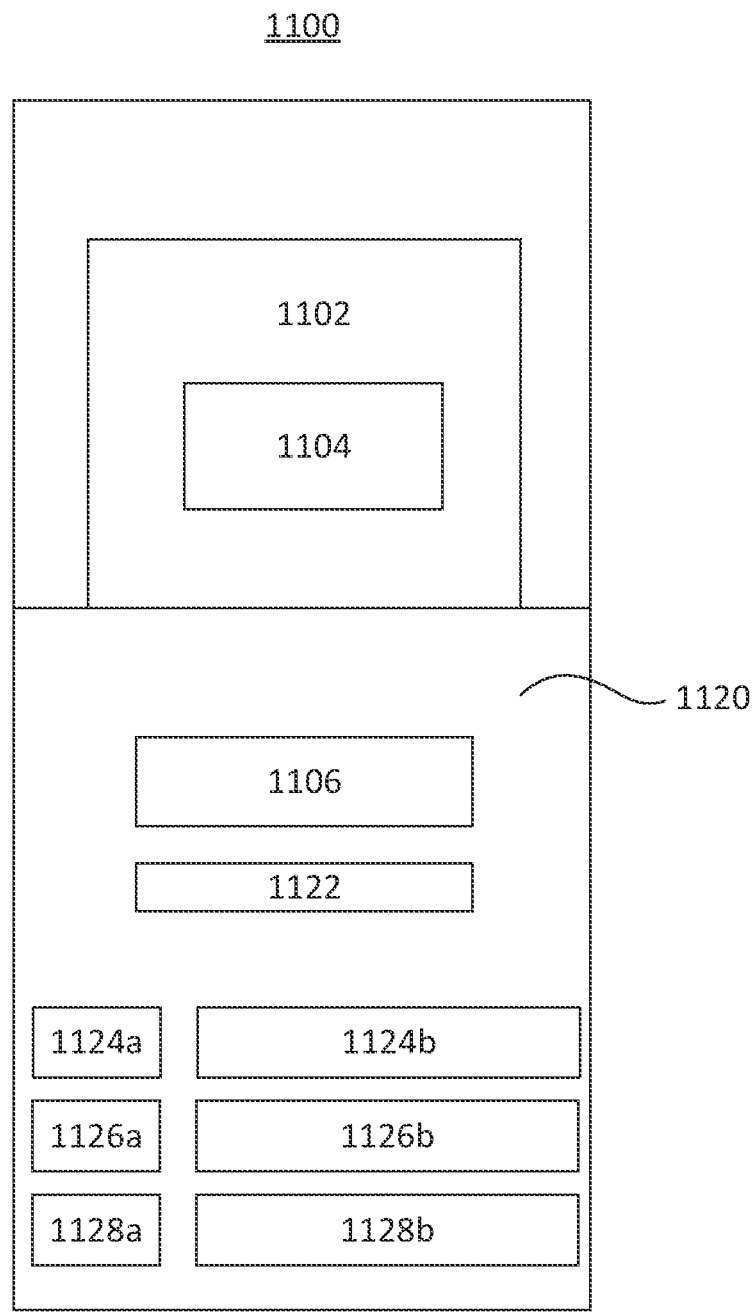

The GUI 1100 may also list the serial number of the current biosensor 1106, which may assist the user if seeking assistance with customer service. If the user selects the serial number 1106, as seen in FIG. 11B, a pop-up screen 1120 or a new full screen GUI with additional details about the biosensor may appear. The pop-up screen 1120 may include the serial number of the current biosensor 1106 and the status of the current biosensor 1122. The pop-up screen 1120 may also include a list of past biosensors 1124, 1126, 1128. The list of past biosensors may include a date 1124a, 1126a, 1128a associated with each biosensor (e.g., the date of activation, or the date that the biosensor was disconnected), along with the serial number and status of the past biosensor 1124b, 1126b, 1128b. In some embodiments, the serial numbers of the current and past biosensors and other information may be copied to assist the user in conveying this information if needed to, e.g., their HCP or customer support. If the current biosensor session has ended, then the GUI 1120 may only include a list of past biosensors.

The GUI 1100 may also include a plurality of selectable links 1110, 1112, 1114, 1116 that, when selected by the user, can display additional information about how to apply the biosensor, options to buy additional biosensors, instructions for use, how to replace a biosensor, support, learning more about the application, learning more about the biosensor, etc.
Support If the user taps or selects the link to "Support," a GUI may include a Help and Learning section, an ABOUT section, and a Customer Care section, which includes details about how to contact a help line. The Help and Learning section may include links to FAQs, Understanding Ketone Readings, and App Tutorial. The ABOUT section may include links to Biosensor IDs, Error History, and App and Biosensor information. As explained elsewhere, the Biosensor IDs link may display a GUI that includes the serial number of the current biosensor, along with a list of past biosensors. The list of past biosensors may include a date associated with each biosensor (e.g., the date of activation, or the date that the biosensor was disconnected), along with the serial number and status of the past biosensor. The Error History link may display a GUI listing each error code, a brief description, and a time and date that the error occurred. The App and Biosensor information link may display a GUI listing the name of the application, the software full version, the SDK version, the OS version, the smartphone model, the country, and a reference number.
Notifications In some embodiments, the biosensor module may provide in-app notifications to alert the user of the status of the biosensor. The in-app notifications may also alert the user as to possible actions to take related to the biosensor. The biosensor module may function to facilitate the host application to display operating system-based notifications related to the status of the biosensor (e.g., informing the user that the biosensor has ended). The in-app notifications may appear in a pop-up notification with the host application in the foreground. In some embodiments, the in-app notifications provided by the third-party application related to the status of the biosensor may only be provided by the biosensor module.

The notifications may relate to the status of the biosensor, as described elsewhere herein. The notifications may relate to enabling BLUETOOTH® and alert the user that Bluetooth is required to receive Biosensor readings, and the notification may request that the user turn Bluetooth on now. The notifications may relate to checking their biosensor and alert the user that it looks like their Biosensor is not applied properly. The notifications may relate to replacing the Biosensor, and alert the user that their Biosensor is not working, instructing the user to remove the Biosensor and pair a new one. The notifications may relate to the end of a Biosensor session, alerting the user that their Biosensor session is completed and that it is time to pair a new Biosensor and continue to learn about their ketone levels. The notifications may relate to the Biosensor being ready, and state that Biosensor data is being received and will be displayed automatically. The notification may also invite the user to explore the ketone diet application. The notifications may relate to the Biosensor ending in a certain number of hours, and request that the user buy a new Biosensor and replace the current Biosensor soon. The number of hours remaining may be 24 hours, 12 hours, 6 hours, 1 hour, or 30 minutes. The notifications may relate to signal from the Biosensor being lost and indicate that the user's phone is out of range of the Biosensor. The notifications may relate to the Biosensor being too hot to give readings, and request that the user check again in a few minutes. The notifications may relate to the Biosensor being too cold to give readings, and request that the user check again in a few minutes. The notifications may relate to a Biosensor error and inform the user that Biosensor reading is unavailable, and request that the user check again in 10 minutes.
Biosensor Ended/Session Completed When a biosensor session has ended and it is time to replace the biosensor, the sensor control module 500 may cause a reminder to pair a new biosensor in numerous ways. In some embodiments, as seen in FIGS. 10A-10B, an icon 1008 and a status information message 1010 may appear that reminds the user to start a new biosensor. The icon 1008 for starting a new biosensor may be a different icon than others used regarding the status of the biosensor and may resemble a full moon, a light bulb, etc. The information message may instruct the user to "start new session."

In some embodiments, a pop-up window 1016 may appear, either in addition to the status information message 1010 or in the alternative or in response to the banner 1002 being selected, and remind the user that the biosensor session has ended and a new biosensor must be paired. In some embodiments, if the life of the biosensor is 14 days, a pop-up window 1016 may appear when the user has just finished a 14-day session and may say that the biosensor session is completed. The pop-up window 1016 may also remind the user that it is time to replace the biosensor by pairing a new biosensor. The pop-up window 1016 may include also include a selectable "Pair" or "Pair Biosensor" button that, when selected, would display a GUI that assists the user to begin the pairing process, as described elsewhere in the application. In some embodiments, the pop-up window 1016 may include a message indicating that "Wear session completed" and instruct the user to continue to learn about their ketone levels by pairing a new biosensor, and include a link to begin pairing a biosensor. The pop-up window 1016 may also include a link to instructions regarding how to apply the biosensor and/or a link to a website where the user may purchase another biosensor.

In some embodiments, as seen in FIG. 10B, the pop-up window 1016 may appear when the user comes back to the host application but has not set up a new sensor. In some embodiments, the pop-up window 1016 may welcome the user back to the application. The pop-up window 1016 may also remind the user to pair a new biosensor. The pop-up window 1016 may include a selectable "Pair" or "Pair Biosensor" button that, when selected, would display a GUI that assists the user to begin the pairing process. The pop-up window 1016 may also include a link to instructions regarding how to apply the biosensor and/or a link to a website where the user may purchase another biosensor. When the user is not browsing the ketone application or when the ketone application is in the background or closed, notifications may appear on the device, e.g., on the lock screen. In some embodiments, the notification may indicate that "Your session is completed!" and suggest that the user pair a new biosensor to keep learning about their body.

The biosensor module details GUI 1100 may also display a reminder to start a new biosensor in as a message associated with graphic 1102, as seen in FIGS. 11A-11B. The message may remind the user to start a new biosensor. The message may also advise the user to please remove the biosensor and pair a new biosensor. GUI 1100 may also include a selectable "Pair" or "Pair Biosensor" button that, when selected, would display a GUI that assists the user to begin the pairing process. In some embodiments, the pop-up window 1120 may appear with a reminder that the new biosensor is ready to scan after the user selects the "Pair" or "Pair Biosensor" button. The pop-up window 1120 may include a graphic of a phone or reader device and may also include instructions reminding the user to hold the top of the phone very close to the biosensor. The pop-up window 1120 may also remind the user that the phone will vibrate or otherwise notify the user (e.g., a sound) after successfully scanning the biosensor.

As mentioned with respect to different GUIs, e.g., the Details GUI, the application may provide a link to "how to replace your biosensor," which may be helpful to new users. If the user selects the link to "how to replace your biosensor," a GUI may be presented with selectable options, (1) removing the biosensor, and (2) applying a new biosensor. The GUI may also include an option for replacing the current biosensor before it ends.

If the user wants to remove the biosensor, a GUI may be displayed that includes a warning that the action of removing the biosensor is not reversible. Once the user removes their biosensor, they will need to start a new one. The GUI may also contain instructions to pull up the edge of the adhesive that keeps the biosensor attached to the user's skin and slowly peel away the adhesive from their skin in one motion. If any remaining residue remains on the skin, it can be removed with warm soapy water or isopropyl alcohol. The GUI may also contain instructions for the user to discard the used biosensor according to their local regulations. Furthermore, it may instruct the user that when they are ready to apply a new biosensor, follow the instructions in a provided link to "Apply New Biosensor." By selecting or tapping the link to "Apply New Biosensor," the GUIs described in the set-up section may appear.

If the user opts to replace the biosensor before it ends, a pop up window may appear asking if the user wants to end the biosensor early. If the user taps "END BIOSENSOR," this will force-end the current biosensor and the user will need to remove it and apply a new biosensor. The pop-up may also contain a warning that this action is not reversible. If the user selects the link to end the biosensor, then the application may display the GUIs associated with replacing the biosensor discussed elsewhere.

After the first biosensor has ended, a pop up may appear that prompts the user to rate the ketone application.

Replace Biosensor Due to Sensor Errors

The application may display a pop-up or alert if the biosensor needs to be replaced. The pop-up or alert may include a warning icon (e.g., an orange triangle with an exclamation point) that warns the user that their biosensor is not working and instructs the user to please replace their biosensor and pair the new biosensor. The pop-up may also include selectable links to "pair" or "pair biosensor" or instructions on how to replace their biosensor. The live screen may also include indications that the biosensor is not working properly. Instead of displaying a current ketone level, the banner may display dash marks (e.g., "- -") instead of a numerical value, and the informational text may state "SEE DETAILS." If the user taps on any part of the banner, the Details GUI, described elsewhere, may appear with the message to replace their biosensor. As described elsewhere, the Details GUI may include links to additional information. For example, the Details GUI may include a link to how to replace the biosensor, order a biosensor, support, and information about the ketone application.

Communication Between Sensor and Applications

Figure 8:
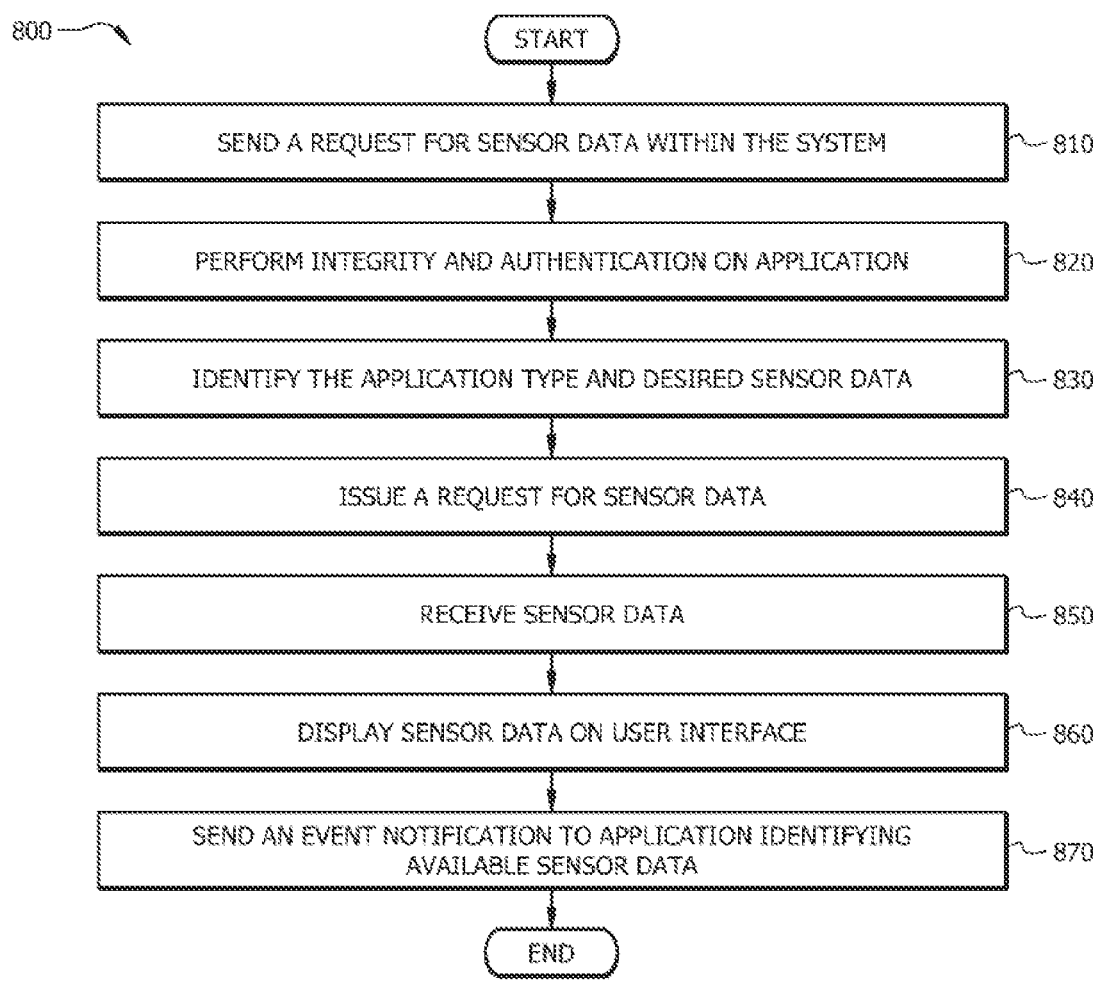
FIGS. 8-9 are example methods for communicating sensor data from a sensor to an application or a third-party application using the disclosed subject matter.

FIG. 8 depicts an example method for communicating sensor data from a sensor to a third-party application 428. As an initial matter, it will be understood by those in the art that any or all of the method steps and/or routines described herein may comprise instructions (e.g., software, firmware, etc.) stored in non-volatile memory of a sensor control device, a remote device (e.g., smartphone, reader), and/or any other computing device that is part of, or in communication with, an analyte monitoring system. Furthermore, the instructions, when executed by the one or more processors of their respective computing device, can cause the one or more processors to perform any one or more of the method steps described herein. Computing device may be the receiving device 200. In addition, although one or more of the method steps and/or routines described herein may comprise software and/or firmware stored on a single computing device, those of skill in the art will recognize that, in certain embodiments, the software and/or firmware may be distributed across multiple similar or disparate computing devices or software modules.

According to one aspect of the embodiments, method 800 can support an application 422, 424, 426 or a third-party application 428 from receiving sensor data for use within the application. At step 810, a third-party application 428 sends a request for sensor data within the system. The request routes to sensor control module 500 through the sensor control module interface 520; the second control module 500 communicates to the sensor assembly 300 using communication control module 540. At step 820, the sensor control module 500 verifies the authenticity of the third-party application 428 and integrity of the session. The sensor control module 500 may further communicate with the remote management module 600 to support user authentication and obtain content specific information for the third-party application 428. These modules may be available within a software library 400 so that a third-party application 428 developer can integrate as a framework within the system of the third-party application 428. At step 830, the sensor control module 500 using logic can identify the third-party application type and desired sensor data.

At step 840, the sensor control module 500 can issue a request for sensor data to the sensor assembly. Alternatively, the sensor control module 500 can be in receipt of sensor data based on a predetermined transmission rate (e.g., every 30 seconds, every minute, every 5 minutes, etc.). According to some embodiments, the sensor data can comprise data indicative of an analyte level, such as, for example, a glucose level, a glucose rate-of-change, a glucose trend, or a glucose alarm condition, among others. At step 850, the sensor data is delivered through a communications link 102 and stored within the database 530 of the sensor control module 500, and displayed at the user interface 510 as shown at step 860.

The sensor control module 500 database 530 includes and can store sensor data separately for each value generated by the various sensor assemblies 300. Database manager 532 may control one or more databases 530 with each separately storing the different types of sensors comprising the sensor assemblies 300. The data may also be stored together within a single database 530. The pictured database 530 is for illustration purposes, not limitation. Separate databases may also be dedicated to storing alarm conditions and triggered alarm results or notifications for each alarm at the sensor control module 500 database 530.

The user interface 510 may also be used to generate alarm notifications to users for alarms that have been triggered based on the sensor data or based on the condition of the sensor assembly 300. The sensor control module 500 may need to alert a user concerning the presence of an alarm. That communication would occur through the sensor control module interface 520 and driven by the user interface 510.

The disclosed subject matter further includes that the remote management module 600 may store alarm notifications and events for the application 422, 424, 426, or third-party application 428 as a backup at the remote server 640. This would allow alarm events to be generated for application 422, 424, 426 or a third-party application 428 that can be stored outside of a module that requires regulatory review and approval. In this manner, different applications developed to monitor a user's health and wellness can use the alarm events for wellness purposes that do not require regulatory clearance. The application 422, 424, 426 or a third-party application 428 may also store sensor data, alarm conditions, or notifications within its own database or shared database separate from database 530 within the sensor control module 500.

As disclosed herein, one such benefit of the software library 400 and modular approach of using the sensor control module 500 is that it would allow users and application developers to identify and develop different wellness related applications for the sensor data. This would enable users that do not traditionally use tracking of analytes, such as glucose monitoring, to consider adding it for purposes of health and wellness such as food tracking, customizable diabetes management, and other unregulated uses. By having the modular sensor control module 500, third-party applications 428 could use the sensor data in any unregulated manner without having to perform the regulatory clearance process. This in turn would expand the user-base for a manufacturer's sensor assemblies 300 by virtue of having more functions available for a user considering using the manufacturer's sensors. Those features can be implemented and improved on these third-party applications 428 without having to submit the revised improvements for regulatory review and clearance, further demonstrating how this disclosure improves initiatives to target wellness for users.

This allows the software library to be expandable to use the sensor control module 500 to collect and provide sensor data for yet to be developed sensors. The modular approach disclosed herein would reduce the need to rewrite code for shared functions and approaches to reading data from the various existing sensors and newly developed sensors, minimizes costs for introducing new sensors, and increases the functions and options for use of that sensor data in a wellness application. The expandable configuration allows the overall system to be extendable to future generations of sensor assemblies 300 and applications of the sensor data to additionally promote wellness use cases. The modular configuration allows third-party application 428 to use a mix and match approach to building and scaling the underlying third-party application 428 and expanding the capabilities offered by third-party application 428. The third-party application 428 can choose which analytes to monitor and incorporate into a wellness program based on the sensor data.

The sensor control module may further, at step 870, issue an event notification to the third-party application 428 identifying that the sensor data is available. The sensor data can be further transmitted using the sensor control module interface 520.

Figure 9:
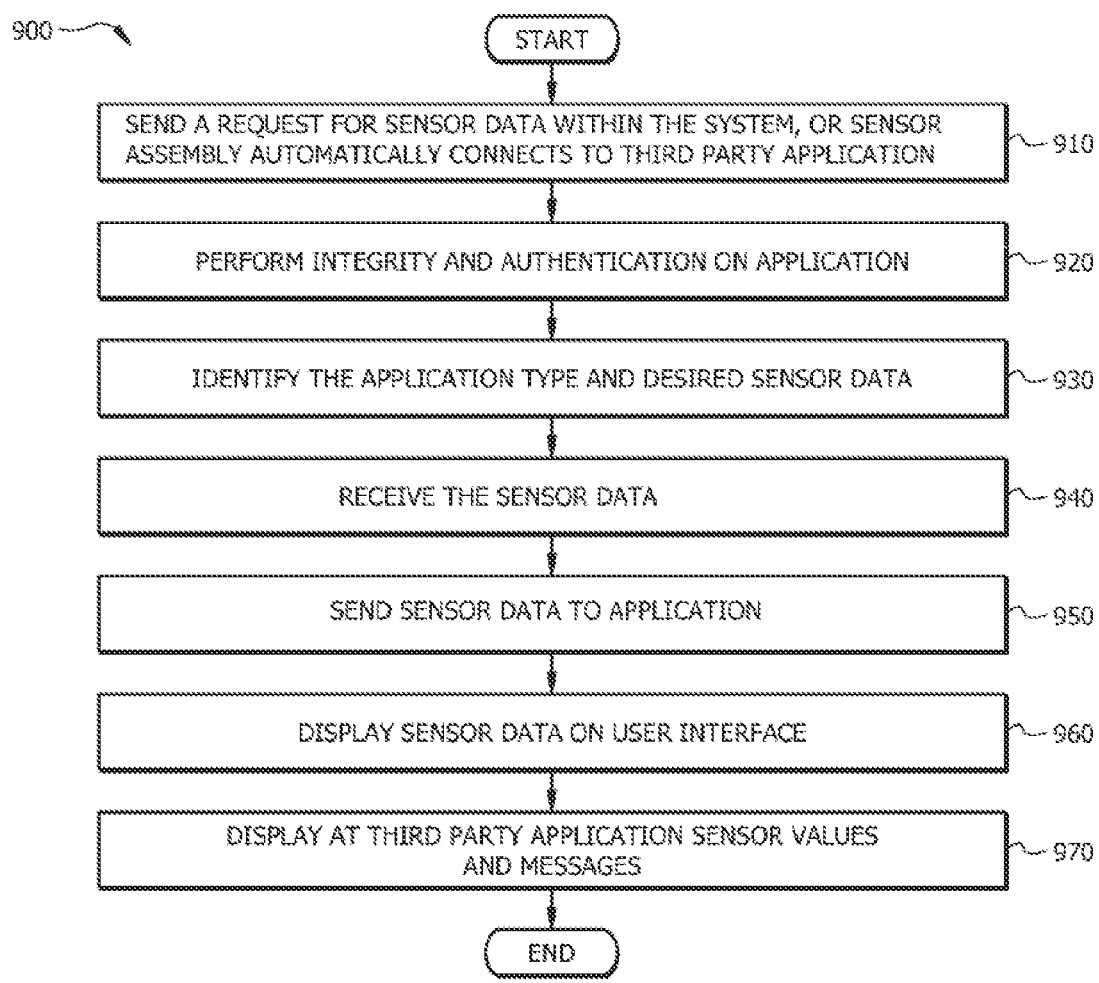

FIG. 9 depicts an example method for communicating sensor data from a sensor to a third-party application 428. As an initial matter, it will be understood by those in the art that any or all of the method steps and/or routines described herein may comprise instructions (e.g., software, firmware, etc.) stored in non-volatile memory of a sensor control device, a remote device (e.g., smartphone, reader), and/or any other computing device that is part of, or in communication with, an analyte monitoring system. Furthermore, the instructions, when executed by the one or more processors of their respective computing device, can cause the one or more processors to perform any one or more of the method steps described herein. Computing device may be the receiving device 200. In addition, although one or more of the method steps and/or routines described herein may comprise software and/or firmware stored on a single computing device, those of skill in the art will recognize that, in certain embodiments, the software and/or firmware may be distributed across multiple similar or disparate computing devices or software modules.

According to one aspect of the embodiments, method 900 can support an application 422, 424, 426 or a third-party application 428 from receiving sensor data for use within the application. At step 910, a third-party application 428 sends a request for sensor data within the system, or the sensor assembly 300 automatically connects to the third-party application 428 using, for example, a BLE connection by issuing a discovery request for BLE capable receiving devices 200 having the third-party application 428. At step 920, the sensor control module 500 verifies the integrity and performs authentication of the third-party application 428. The sensor control module 500 may further communicate with the remote management module 600 to support integrity and obtain content specific information for the third-party application 428. These modules may be available within a software library 400 that a third-party application 428 developer can integrate as a framework within the system of the third-party application 428. At step 930, the sensor control module 500 using logic can identify the third-party application 428 type and desired sensor data to issue requests for the desired data. Optionally, because the session has been authenticated, the sensor assembly 300 may send sensor data through the communication control module 540 and sensor control module interface 520 without a request.

At step 940, the sensor control module 500 receives the sensor data. As stated above, the sensor data can comprise data indicative of an analyte level, such as, for example, a glucose level, a glucose rate-of-change, a glucose trend, or a glucose alarm condition, among others.

At step 950, the sensor data at the sensor control module 500 is sent to the third-party application through the sensor control module interface 520. At step 960, the sensor data is displayed on the user interface 510 of the sensor control module.

At step 970, the third-party application 428 displays any additional messaging related to the sensor assembly 300, including the sensor data relating to analyte levels, notifications, alarms, a message, or other issue regarding the sensors or meal and exercise recommendations based on received sensor data from step 950. Thus, part of the display is via sensor control module 500 regarding analyte levels, whereas another portion of the display on the third-party application 428 is done specifically by the third-party application 428 outside of the control of the sensor control module 500.

The software library 400 and sensor control module 500 as disclosed herein can be used with applications 422, 424, 426. Applications 422, 424, 426 may include various current applications, such as glucose sensor for diabetic monitoring, glucose and ketone sensor for diabetic monitoring, glucose sensor and an insulin delivery device for diabetic monitoring and closed-loop insulin delivery system. As disclosed herein, these applications may require various regulated functions and thus need to be submitted in full for regulatory clearance. As disclosed herein, various modifications and functionalities can be added to these applications that do not fall within the core functions for diabetic monitoring and insulin delivery, allowing for unregulated expansion of functions provided by applications based on the sensor data. As further disclosed herein, additional functions can be implemented by applications 422, 424, 426 or third-party applications 428 for wellness, such as glucose sensor for sports or fitness monitoring or for wellness and diet, ketone sensor for wellness or diet plan, such as a keto diet plan, lactate sensor for sports and fitness monitoring, or any number of other applications including alcohol monitoring for treatment and compliance, sST2, Calprotectin, HNL, NT-pro-BNP. Such functionalities can be performed by applications 422, 424, 426 or by third-party applications 428 and reside outside of the core functionality necessary for regulatory review. Thus, enhancements to these functionalities would not need to be submitted for regulatory clearance before introducing the functionalities to the consumer market by use of the modular framework as disclosed herein.

The biosensor banner and GUIs described herein may be provided in different color scheme options, e.g., with dark and light backgrounds, to provide the host or third-party application developer a plurality of options from which to choose to include in their application.

Ketone Diet Application

Onboarding

In some embodiments, an application that communicates with the sensor control module 500 may be a wellness application that monitors ketone levels in a subject or user. The ketone wellness or diet application may include a GUI that assists the user in setting up their biosensor. The GUI may have a selectable button allowing them to start setup, and may also include a graphic of a biosensor and a text description regarding the setup. The text description may include a message saying "Hello" and prompt the user to begin by setting up their biosensor so that they can start getting a read on their body's own unique language.

As seen in FIG. 13A, when a user first applies the sensor to their body and opens the ketone diet application, GUI 1300 may be displayed, which indicates the time remaining for the biosensor to be ready. The GUI 1300 may include a graphic 1302 highlighting the time remaining until the biosensor is active. The graphic 1302 may include a radiating circle of dots, which may be animated. Alternatively, the graphic 1302 may include a progress indicator that may be a bar having a colored portion or may be a colored portion along the perimeter of a circle, where the colored portion is proportional to the amount of time remaining before the sensor is active, e.g., a total perimeter of a circle may be equivalent to 60 minutes and a colored portion of the perimeter may be proportional to the amount of time remaining under an hour for the biosensor to be active. Alternatively, the graphic 1302 may be animated and the color of the perimeter of the circle may change as the time remaining is counting down. The GUI 1300 may also include a display 1306 of the number of minutes until the biosensor is active (e.g., "Ready in 55 mins"). For example, in some embodiments, a message of "Ready in 55 mins" may be displayed on the inside of a circle, where a colored portion of the perimeter of the circle is animated and cyclically changes color as the time remaining until the biosensor is active counts down. The GUI 1300 may include links to additional information. For example, GUI 1300 may include a link to how to replace the biosensor, order a biosensor, support, and information about the ketone application. The GUI 1300 may also include a description or message 1304 that informs the user that they can soon start monitoring their ketosis in real time. Moreover, it may indicate that the user can learn how their diet, exercise, and everyday habits can impact their ketone levels. In some embodiments, elements of GUI 1300 may be provided by the biosensor module. For example, the graphic having a progress indicator 1302 and the display 1306 of the number of minutes until the biosensor is active may be provided by the biosensor module.

When a user first opens or logs into the ketone diet application, a series of GUIs may appear to customize the user's experience and assist the user in making goals for the ketone diet application to monitor.

The ketone diet application may ask the user about their experience with keto. The ketone diet application may present a GUI displaying a plurality of selectable answers, including but not limited to, (i) I'm a newcomer, (ii) I've tried it before, and (iii) I'm a keto master.

The ketone diet application may ask the user what they want to achieve by using the application. As seen in FIG. 13B, the ketone diet application may present a GUI 1310 displaying a plurality of selectable answers 1314*a-e*, including but not limited to, (i) manage weight, (ii) try something new, (iii) improve mental clarity, (iv) manage appetite, (v) improve energy levels, (vi) control hunger, and (vii) other. The user may select one or more goals to achieve. The GUI 1310 may also include a progress bar 1312 that indicates how far the user is in the setup process. For instance, where there are four GUIs related to the setup and GUI 1310 is the first in the series of GUIs, then ¼ of the progress bar 1312 may be shaded a different color to indicate that the user is ¼ of the way through the setup process.

Once the user indicates or selects their main goals for using the application, the ketone diet application may present additional questions to further identify and clarify the user's goal in order to optimize their user experience and present personalized goals and recommendations. For example, if the user selects the option to manage weight, the ketone diet application may ask the user why they want to manage their weight. The ketone diet application may present a plurality of selectable answers, including but not limited to, (i) to lose weight, (ii) to maintain weight, and (iii) to gain weight.

The ketone diet application may ask the user to enter their measurements and other personal information. For example, as seen in FIG. 13C, the ketone diet application may include GUI 1330 that prompts the user to enter their measurements, such as, height, weight, and other information necessary to calculate a macronutrient recommendation. The GUI 1330 may include options to select either Imperial 1332 or Metric 1334 units to enter the measurements. The GUI 1330 may include a height section 1336 in which the user may select the appropriate height in a rotating wheel, the user may enter in their height in a text entry field, or by other means known in the art. Similarly, the GUI 1330 may include a weight section 1338 in which the user may select the appropriate weight in a rotating wheel, the user may enter in their weight in a text entry field, or by other means known in the art. The GUI 1330 may also include the progress bar 1312 that indicates how far the user is in the setup process. For instance, where there are four GUIs related to the setup and GUI 1330 is the second in the series of GUIs, then ½ of the progress bar 1312 may be shaded a different color to indicate that the user is ½ of the way through the setup process.

The ketone diet application may ask the user to enter their birth date or select their birth date. For example, as seen in FIG. 13D, the ketone diet application may include GUI 1350 that prompts the user to enter their birth date 1352. The GUI 1350 may include a birthdate section 1352 in which the user may select the appropriate month, day, and year in rotating wheels, the user may enter in their height in a text entry field, or by other means known in the art. The GUI 1350 may also include the progress bar 1312 that indicates how far the user is in the setup process. For instance, where there are four GUIs related to the setup and GUI 1350 is the third in the series of GUIs, then ¾ of the progress bar 1312 may be shaded a different color to indicate that the user is ¾ of the way through the setup process.

Figure 13E:
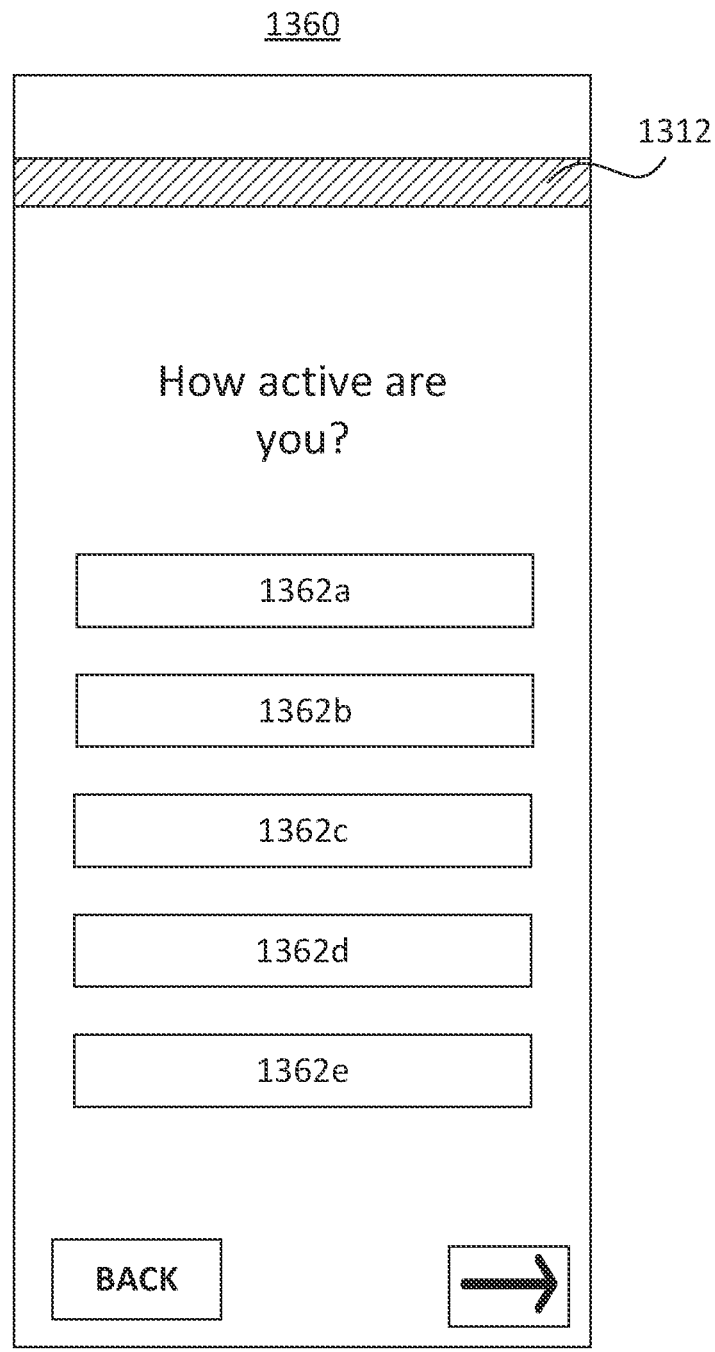
FIG. 13E is a block diagram depicting an example embodiment of a GUI related to receiving the user's activity level.

The ketone diet application may also ask the user how active they typically are or to identify their activity level. For example, as seen in FIG. 13E, the ketone diet application may include GUI 1360 that prompts the user to enter a level or a description of their typical activity level. The ketone diet application may present a plurality of selectable answers 1362a-1362e, including but not limited to, (i) somewhat sedentary—e.g., the user takes it easy all day long, (ii) lightly active—e.g., active throughout the day but rarely breaks a sweat, (iii) moderately active—e.g., breaks a sweat 30 minutes a day, a few days a week, (iv) very active—e.g., does 60 minutes of exercise, almost daily, and (v) super active—e.g., exercises daily for over 60 minutes. The GUI 1360 may also optionally include the progress bar 1312 that indicates how far the user is in the setup process. For instance, where there are four GUIs related to the setup and GUI 1360 is the fourth in the series of GUIs, then 100% of the progress bar 1312 may be shaded a different color to indicate that the user is 100% of the way through the setup process.

Figure 13F:
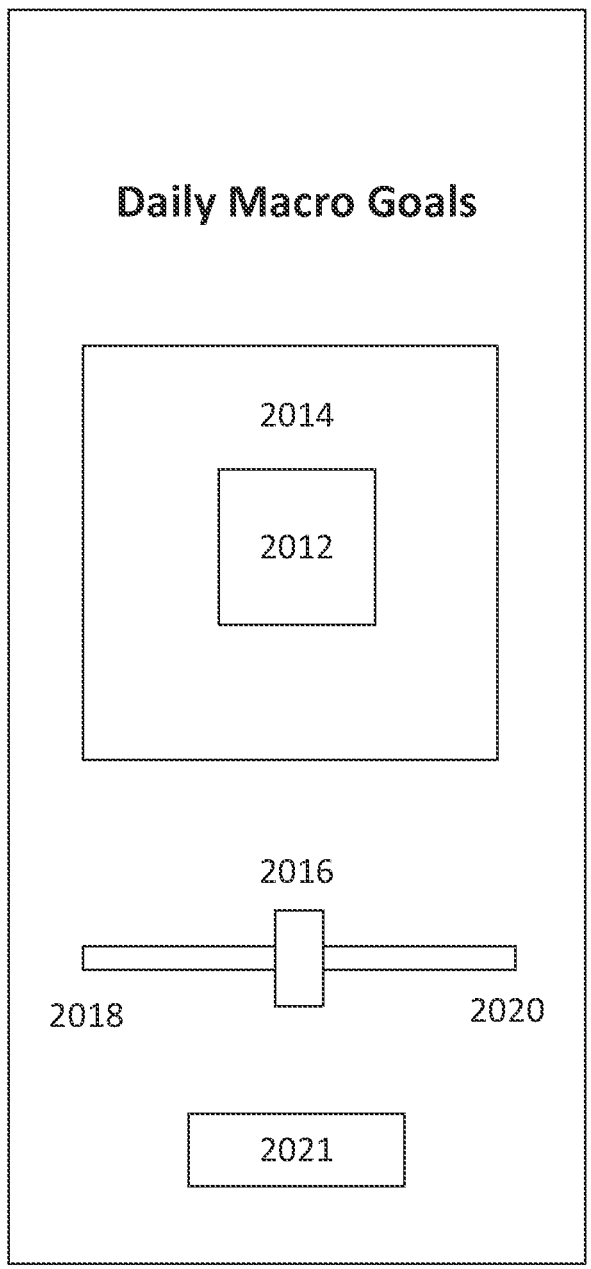
FIG. 13F is a block diagram depicting an example embodiment of a GUI related to daily macro goals.

The ketone diet application may determine recommended daily macro goals for the user based on at least some of the information gathered. The daily recommended macro goals may be displayed as seen in GUI 2010 of FIG. 13F. The daily recommended macro goals may include a recommended total number of calories 2012, along with a recommended relative daily amount of carbohydrates, protein, and fat. The recommended daily amount of carbohydrates, protein, and fat may be presented as percentages or as a weight amount (e.g., in grams) in a graphical display 2014 that illustrates the relative recommended amounts of each of the carbohydrates, protein, and fat. The use may toggle between displaying the goals in percentages or weight (e.g., grams) by tapping on the graphic to change the units. For example, graphical display 2014 may be a circular graph or a pie chart, in which the circle or pie chart is divided up into three sections, a section each for carbohydrates, protein, and fat, with the size of each of the sections being proportional to the recommended amount of that type of nutrient. For example, if a daily macro nutrient recommendation was for 60% fat, 30% protein, and <10% carbs, then 60% of the area or circumference of the circle or pie chart would be colored a first color and labeled as 60% fat (or the corresponding amount of grams of fat), 30% of the area or circumference of the circle or pie chart would be colored a second color and labeled as 30% protein (or the corresponding amount of grams of protein), and <10% of the area or circumference of the circle or pie chart would be colored a third color and labeled as <10% carbs (or the corresponding amount of grams of carbs). The recommended total calories 2012 may be displayed in the center of the graphical display 2014. A user may tap the graphical display 2014 to toggle between the goals displayed in percentages or in grams. The GUI 2010 may also contain a link for more information as to why the daily macro goals are important. By tapping the link, a GUI may appear that explains that the daily recommendation is to help get the user into ketosis quickly and efficiently. It may also recommend that the user check with a registered dietitian or health care professional before putting the daily macro goals to work. The GUI may also warn that it may take 3-7 days for the user to start producing ketones.

Females and males typically burn on average a different number of calories per day per day than males. The ketone diet application may also include an option to view the estimates for a female or a male. GUI 2010 may include a switch (not shown) or a slide toggle 2016, which may be slid to one side 2018 to view a female estimate and the other side 2020 to view the male estimate. When the user slides toggle 2016 to the female side 2018, the GUI 2010 may inform the user that females burn on average 12% fewer calories per day than males, and may also display an adjusted lower recommended total calories.

The ketone diet application may also explain that the daily recommended macro goals are intended to get the user into ketosis quickly and efficiently. The ketone diet application may also explain that it is important to stick with the recommendation as it typically takes 3-4, alternatively 3-7 days for a person to start producing ketones.

The ketone diet application may also include the option to skip the macro customization, and allow the user to start setting up the biosensor without calculating the daily macro goals or postponing the calculation of the daily macro goals.

GUI 2010 may also contain a button 2021 that when selected, opens additional GUIs relating to the setup of the biosensor and other aspects of the application.

Setup Biosensor

Figure 13G:
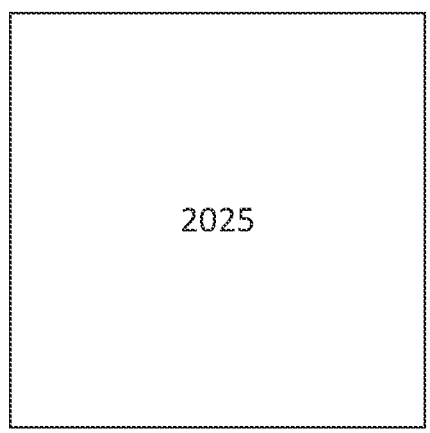
FIG. 13G is a block diagram depicting an example embodiment of a GUI related to setting up the biosensor.
Figure 13G:
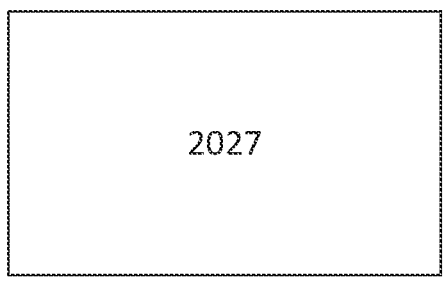
Figure 13G:
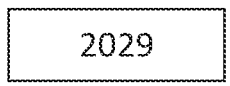

As seen in FIG. 13G, GUI 2023 may include a graphic 2025 of a biosensor along with text 2027 relating to setting up the biosensor. The text 2027 may ask the user if they are ready to listen to their body. The text 2027 may further state that it is time to set up their biosensor and learn their body's unique language. The GUI 2023 may include a button 2029 that opens a GUI to start the setup of the biosensor, as described elsewhere in this application.

The ketone application may ask the user to enable BLUETOOTH® to allow the application to find and connect with the biosensor. This will enable the ketone application to see real-time ketone levels and also receive data relating to the biosensor status.

The ketone application may also ask the user to enable push notifications on the mobile device. The notifications may include alerts, sounds, and icon badges. The notifications may allow the ketone application to inform the user when they have reached ketosis or dropped out of ketosis.

Setting a Target

Figure 14A:
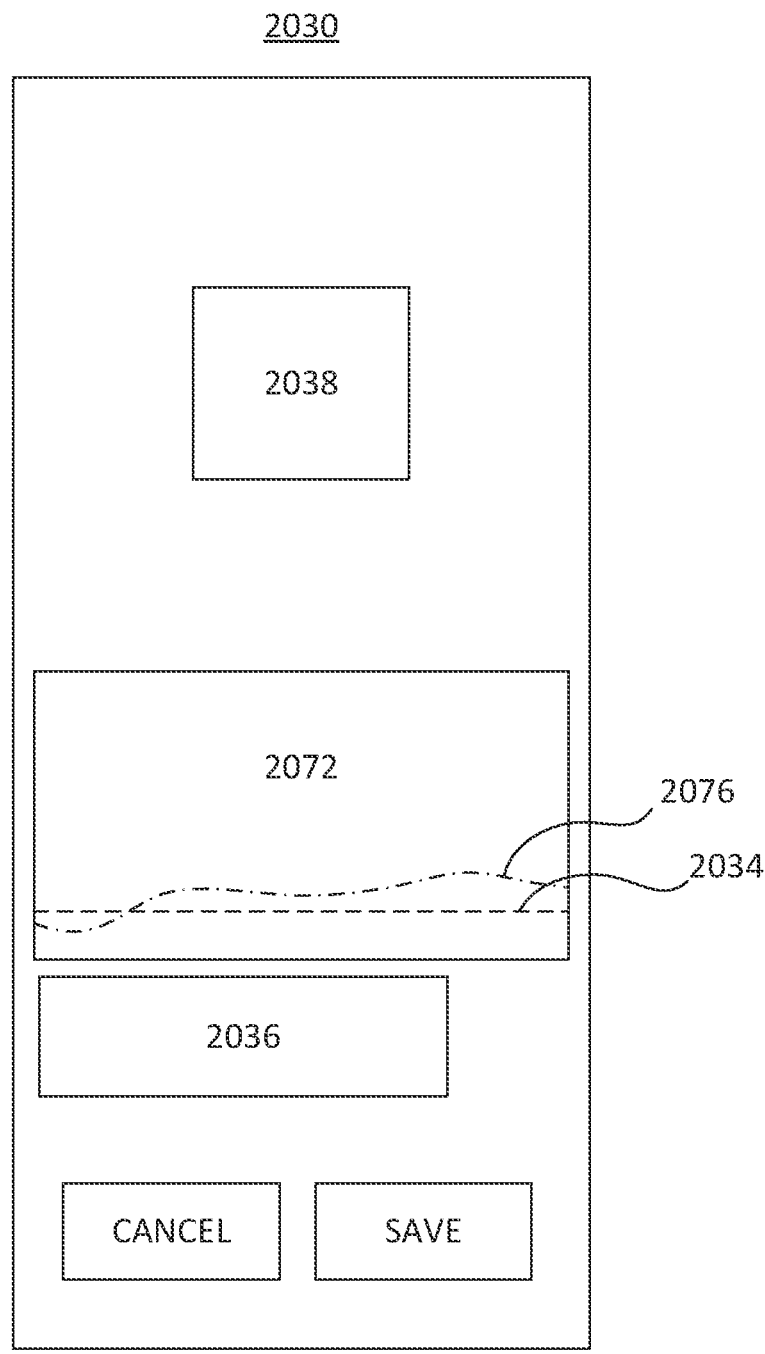
FIGS. 14A-14B are block diagrams depicting example embodiments of GUIs related to setting a target ketone threshold.
Figure 15A:
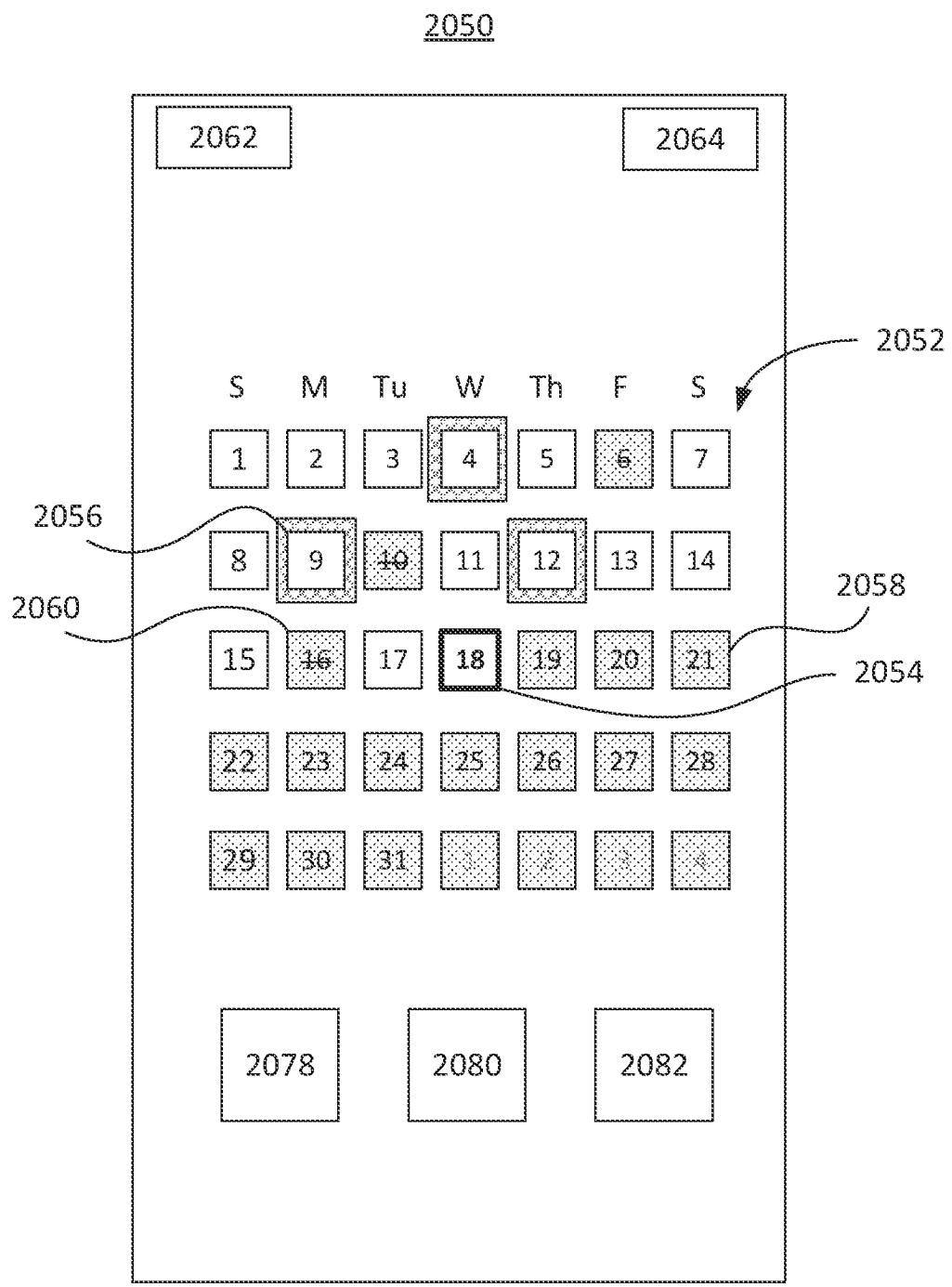
FIG. 15A is a block diagram depicting an example embodiment of a GUI related to a calendar view.
Figure 15B:
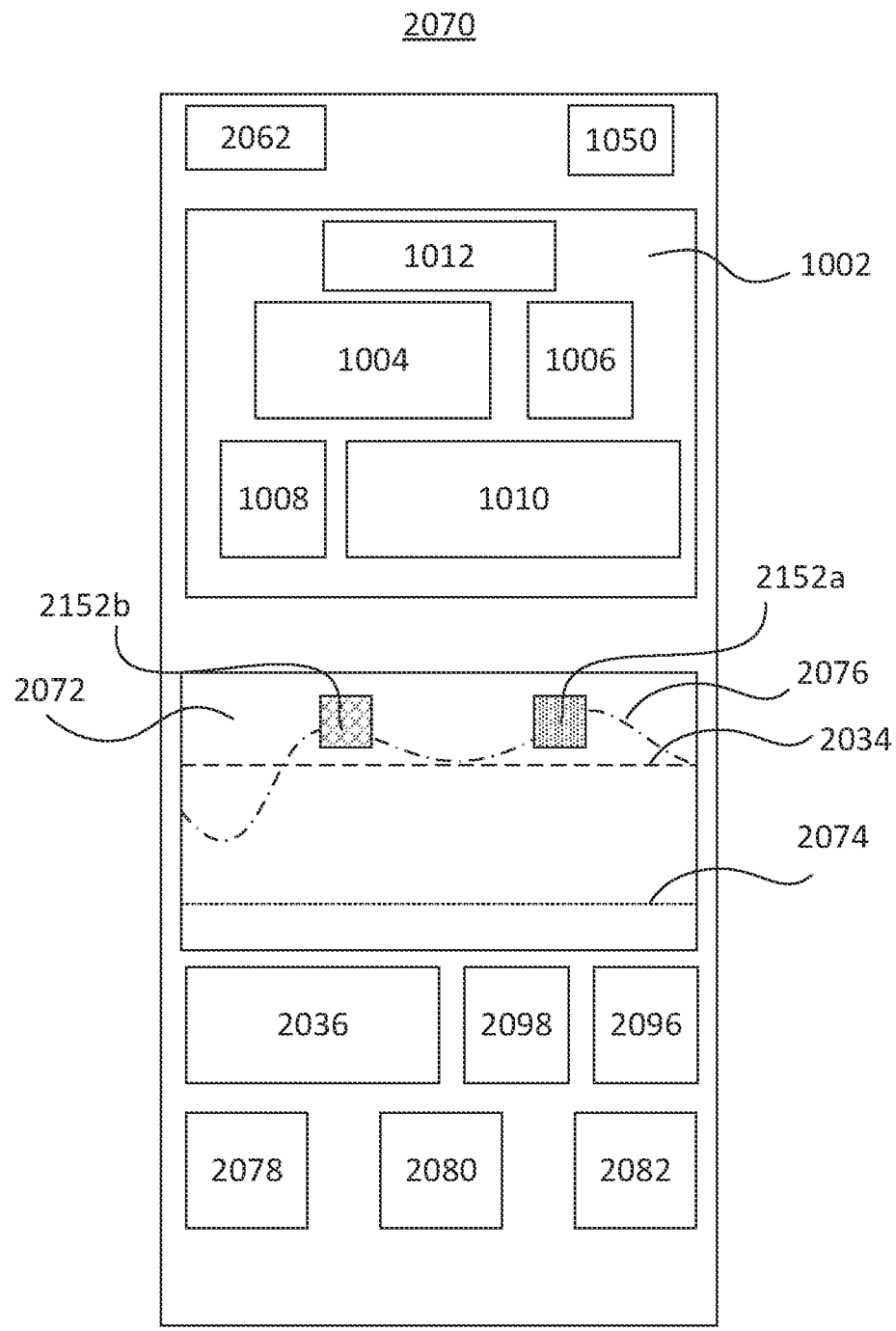
FIG. 15B is a block diagram depicting an example embodiment of a GUI related to a live home screen for a current day.

In some embodiments, the user may set a target ketosis concentration by tapping on a set target button 2096, as seen in FIG. 15B. With reference to FIG. 14A, the user may set a target by dragging a line 2034 on a graph 2072 of the ketone levels to a desired ketone concentration. Alternatively, the user may set the target by entering a concentration at a prompt.

Figure 14B:
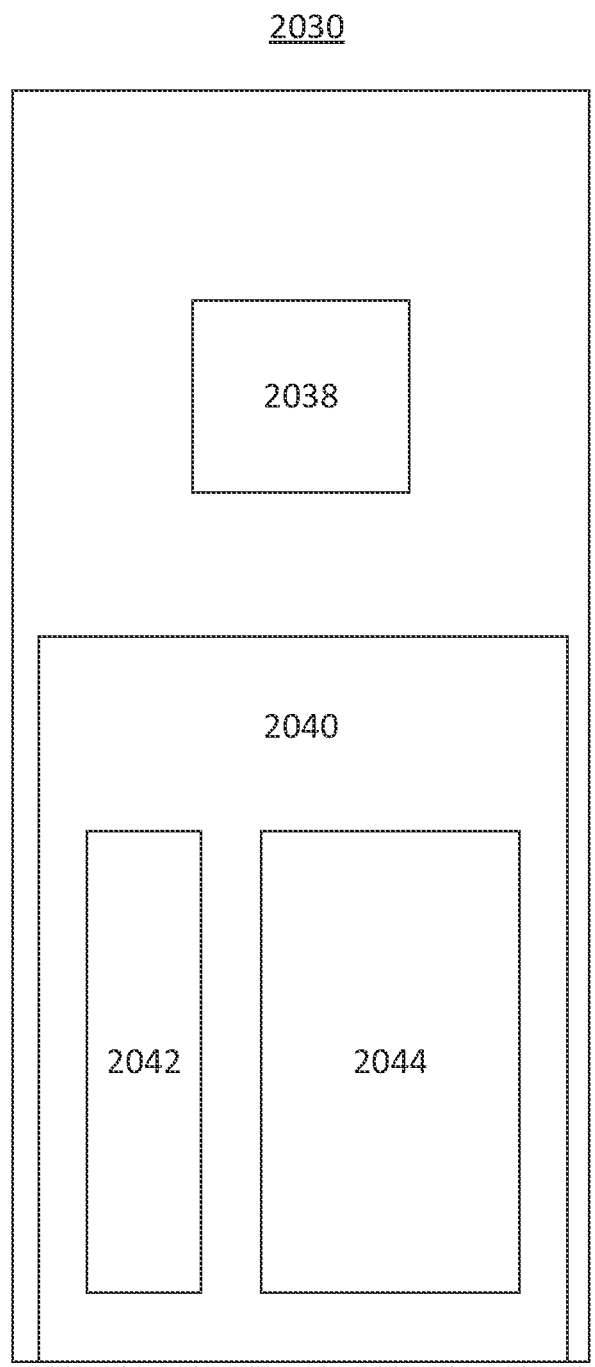

As seen in FIG. 14B, a pop-up window 2040 may appear that gives more information about where the user should set the target. The pop-up window 2040 may suggest setting the target between 0.5 and 8.0 mmol/L. The pop-up window 2040 may also suggest that the user adjust the target regularly until the user knows which level fits them best. The pop-up window 2040 may also present a graph 2042 or information that shows a plurality of ranges, along with a description 2044 of the various concentrations listed in the graph 2042. For example, the pop-up may indicate that 8.0 mmol/L is a deep ketosis limit and that 0.5 mmol/L is a ketosis threshold. It may also indicate that above 8.0 mmol/L the user is above the range, between 4.0 mmol/L and 8.0 mmol/L the user is in deep ketosis, between 0.5 mmol/L and 4.0 mmol/L the user is in ketosis, and that below 0.5 mmol/L the user is under ketosis.

Once the user has set the target threshold, the target concentration may appear in the graph as a line 2034, which may also appear in the legend 2036 as e.g., "My target", and the numerical value of the target threshold 2038 may appear on the GUI 2030. The user may then select "save" to save the target threshold.

After the target is set, in addition to displaying the daily average ketone concentration and the hours total in ketosis, the home and/or live screen may also display the total hours above the target (see, e.g., 2082 of FIG. 15B).

In some embodiments, where no target is set by a user, the graph 2072 may contain only a line depicting the ketosis threshold 2074 or the level above which nutritional ketosis is reached.

Calendar and Past Days

In the ketone diet application, the user may click on the timeline or otherwise access a calendar view. For example, if the user selects the date 2062, a calendar GUI 2050 may appear in a drop-down window or in a separate window. With reference to FIG. 15A, GUI 2050 may include a view of the dates of the current month 2052 and optionally the ending of the previous month and/or the beginning of the next month. In the calendar, the current day 2054 may be highlighted, e.g., outlined in a different color or otherwise distinguishable. The days on which ketosis has been met 2056 may also be highlighted with a different color or outline. The days in the future 2058 may be grayed out and the user may not be able to select these days in the future. The days in the past that lack data 2060 may be grayed out and additionally the date may be crossed out. The user may also not select these past dates that lack data 2060. If the user taps or selects any date other than the current day or a grayed out date, then the calendar view may close and a Live screen for the selected date may be displayed. The ketone diet application may also be configured such that the user may swipe the calendar screen to go to previous months. GUI 2050 may display the date that the user selects 2062 and also may include a link 2064 e.g., named "TODAY" that, when selected, may cause a live home screen 2070 to appear. If the user taps on or selects any day that is not grayed out or grayed out/crossed out, then the calendar view 2050 may close and the live home screen 2070 may show the selected date's data. If the user scrolls on the live home screen 2070, the ketone diet application may show previous dates when the sensor was active. Days when the sensor was inactive or days in which lack data may be skipped. Once a sensor has ended, the live home screen may show a "start a new biosensor" message rather than a current ketone level.

As seen in FIG. 15B, the live home screen 2070 may include the banner 1002 described elsewhere in this application. As described elsewhere, the banner 1002 may include any of a real time concentration value 1004, a trend arrow 1006, an icon 1008 indicating the status of the biosensor, information 1010 regarding the status of the biosensor, and an additional indication of the biosensor status 1012. The trend arrow 1006 indicates the user's recent ketone trend and may appear when the ketone level is above a threshold, e.g., 0.3 mmol/L. The trend arrow may be angled upward to the right (e.g., in a northeast direction) to indicate that the ketone levels are rising. The trend arrow may be angled downward to the right (e.g., in a southeast direction) to indicate that the ketone levels are falling. The trend arrow may be horizontal and pointed (e.g., pointed East) to indicate that the ketone levels are changing slowly. The biosensor module may report ketone concentrations in different ranges in different ways. When the concentration is less than a low threshold value, the real time concentration may be displayed as <low threshold, e.g., "<0.3 mmol/L" rather than displaying the concentration (e.g., 0.1 mmol/L). The low threshold value may be about 0.2 mmol/L, alternatively about 0.25 mmol/L, alternatively about 0.3 mmol/L, alternatively about 0.35 mmol/L. When the concentration is above a high threshold value, the real time concentration may be displayed as >high threshold, e.g., ">0.6 mmol/l" rather than displaying the concentration (e.g., 0.8 mmol/L). The high threshold value may be about 0.5 mmol/L, alternatively about 0.55 mmol/L, alternatively about 0.6 mmol/L, alternatively about 0.65 mmol/L. When the concentration is between the low and high threshold values, then the application may display the concentration level.

The live home screen GUI 2070 may have an indication of whether or not ketosis that day was reached, such as a different color, icon, and/or text (e.g., "Ketosis Not Reached" or "Ketosis Reached"). In some embodiments, the indication of whether or not ketosis that day was reached may appear in a drop-down notification. The live home screen GUI 2070 may also include a graph 2072 of the ketone levels. The graph 2072 may show a ketone curve 2076 for a 24 hour period, ketosis threshold 2074, and ketosis target 2034. The ketosis threshold may be labeled as "Nutritional Ketosis" in the legend 2036. An area under the ketone curve 2076 may be shaded, e.g., from the ketone curve 2076 to the x-axis (time). The shading may be a partially transparent gradient of a first color, where the gradient is less transparent closer to the ketone curve 2076 and grows more transparent closer to the x-axis (time). The graph 2072 may automatically scale the y-axis (ketone concentrations) to maximize the height of the ketone curve 2076 displayed. Icons (e.g., 2152a, b) may appear on the ketone curve 2076 where a logged entry occurs. The logged entries may relate to eating habits, exercise, appetite, mood, fasting, energy levels, etc. The live home screen GUI 2070 may also display the daily average 2078 for that day, total hours in ketosis for that day 2080, and total hours above target for that day 2082.

Figure 15C:
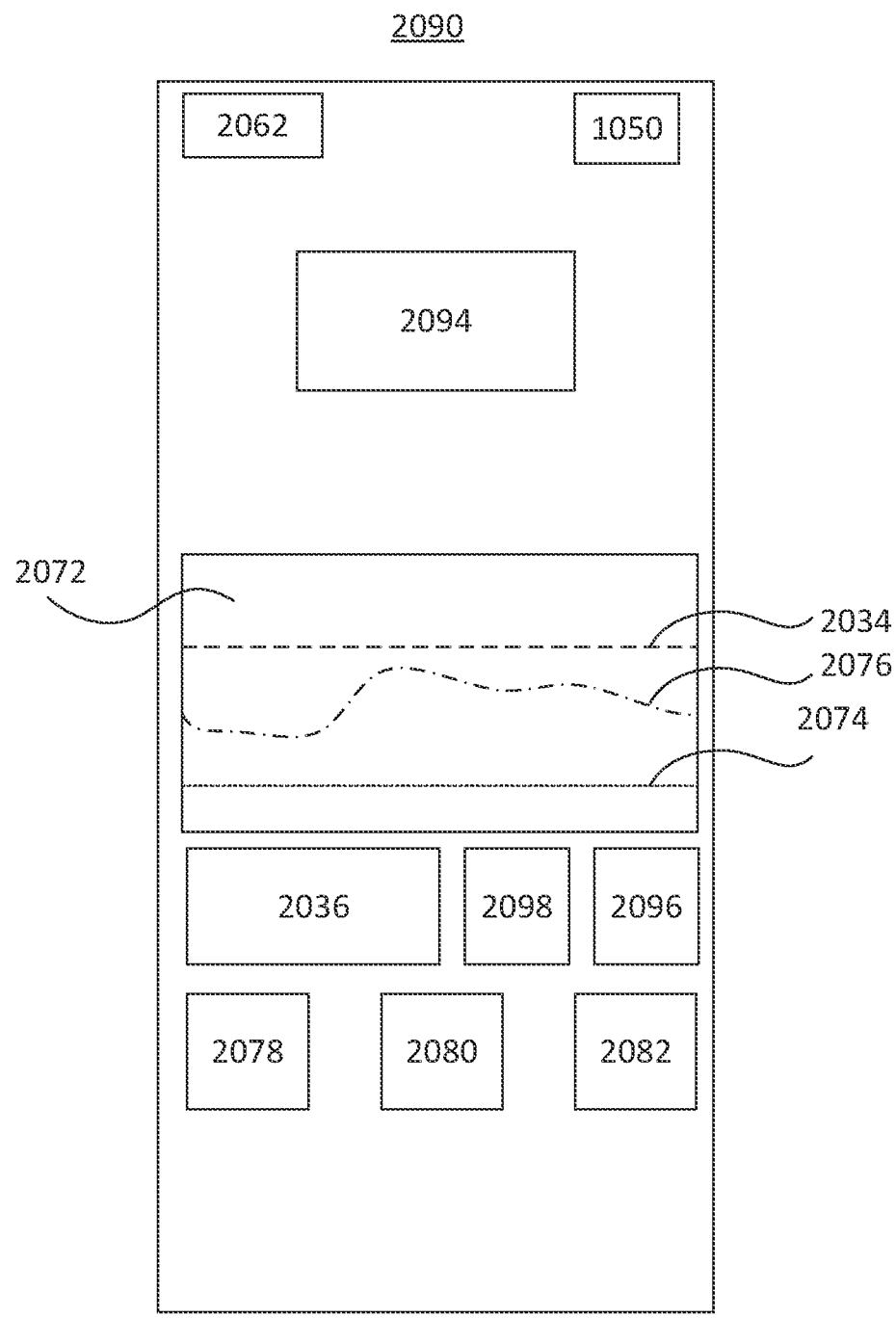
FIG. 15C is a block diagram depicting an example embodiment of a GUI related to a live home screen for a past day.
Figure 15D:
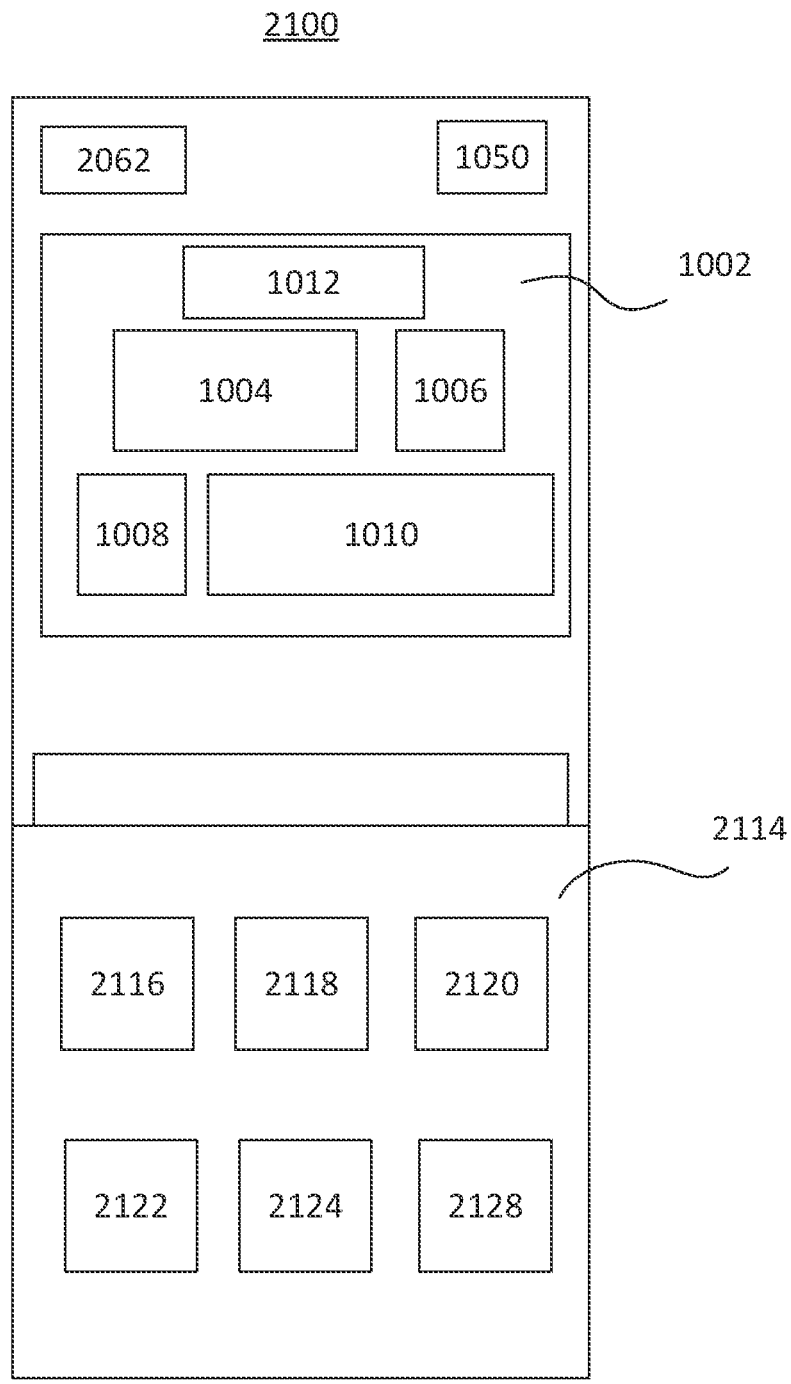
FIG. 15D is a block diagram depicting an example embodiment of a GUI related to a log filter.

The user may swipe to access the live home screen 2070 for past days. As seen in FIG. 15C, the live home screen for a past day 2090 may include all of the same information included in the live home screen 2070 for the current day. The live home screen for a past day 2090 may include a graph 2072 of the ketone levels. The graph 2072 may show a ketone curve 2076 for a 24-hour period, ketosis threshold 2074, and ketosis target 2034. An area under the ketone curve 2076 may be shaded. The shading may be a partially transparent gradient of a first color, where the gradient is less transparent closer to the ketone curve 2076 and grows more transparent closer to the x-axis (time). The graph 2072 may automatically scale the y-axis (ketone concentrations) to maximize the height of the ketone curve 2076 displayed. The graph 2072 may be scaled to keep the highest and lowest point of the graph within the graph. In some embodiments, the graph may be scaled such that the highest point of the graph is within a top 10% of the graph and the lowest point is within a bottom 10% of the graph. Icons (e.g., 2152*a, b*) may appear on the ketone curve 2076 where a logged entry occurs. The logged entries may relate to eating habits, exercise, appetite, mood, fasting, energy levels, etc. As seen in FIG. 15F, if several logged entries are close together in time such that the icons overlap on the ketone curve 2076, a pill 2157 may appear on the ketone curve 2076 that includes the number of logged entries with logging times occurring within a predetermined time period or icons that overlap. The predetermined time period may be within about 2 hours or less, alternatively within about 1.5 hours or less, alternatively within about 1 hours or less, alternatively within about 30 minutes or less, alternatively within about 15 minutes or less. If the user taps on the pill 2157, a tooltip 2159 or pop-up window may appear that includes an entry for each of the overlapping icons. Each entry may include the icon, a time of the log entry, and a brief description of the log entry. In some embodiments, the pill 2157 may only appear when the graph is at a maximum zoom in level, and when there is still overlap in the icons at the maximum zoom level.

In some embodiments, instead of the banner 1002, the live home screen for a past day 2090 may include a message 2094 as to whether ketosis was reached that past day or not. The message 2094 may include a text portion that indicates that "ketosis reached" or "ketosis not reached." The message 2094 may also include an icon that may be different colors depending on whether or not ketosis was reached that day. For instance, the icon may be colored a first color if ketosis was reached or grayed out if ketosis was not reached.

The live GUIs for past days may also include a link (e.g., "Today") that, when selected, will result in the immediate display of the current day's live screen. When scrolling through past live screens, dates when a sensor was inactive (for, e.g., 24 hours) are skipped and the next date when the sensor was active is displayed. A sensor may be inactive if the system did not receive any data for a period of time, e.g., 24 hours, due to error statuses. Error statuses, as described elsewhere, may include but are not limited to check biosensor, replace biosensor, and biosensor ended.

As the user scrolls between days, if the graph's 2072 x-axis shows a beginning of the day on the left (e.g., 12 am), then when the user drags the graph, a small gap may appear, and the current day's graph being viewed moves to the right, and yesterday's graph may snap into place.

For the various GUIs including ketone curve graphs, users may zoom in on the graph 2072, but the display may default to a view beginning at 12 am and extending to 12 pm, with 6-hour increments noted on the x-axis. A user may zoom out by pinching the graph and zoom in by unpinching the graph. In some embodiments, the number of increments listed on the x-axis may stay the same for the various scales. For example, the graph may include about 4, alternatively about 5, alternatively about 6 labeled x-coordinates. In some embodiments, the time increments between the labeled coordinates on the x-axis may vary depending on the time window on which the user focuses. For example, if the user zooms into a 16-hour window, the increments on the x-axis may change to 4-hour increments. If the user zooms into an 8-hour window, the increments on the x-axis may change to 2-hour increments. If the user zooms into a 4-hour window, the increments on the x-axis may change to 1-hour increments. If the user zooms into a 2-hour window, the increments on the x-axis may change to 30-minute increments. Between different time windows in which the time intervals displayed on the x-axis change, the time intervals may remain the same but the spacings between each time interval may stretch. For example, for a zoom screen displaying about 20 hours, the time increments may still be displayed in 6-hour increments noted on the x-axis, but the spacing between the 6-hour increments will be different from the spacing in the 24-hour graph. As the user scrolls between live screens for different days, the zoom level of the x-axis may remain the same as the previous graph's zoom level. The user may change the zoom level for any day's view. When the user swipes to previous or next days, the zoom level may follow that last level set by the user.

The y-axis of the graph 2072 may have a first default scale until the user's ketone levels reach a threshold value for the first time. Then the y-axis may automatically change to a second default scale. For example, the first default scale may be 0 to 3.0 mmol/L. The threshold value may be between about 2.5 mmol/L and about 3.0 mmol/L, alternatively about 2.6 mmol/L, alternatively about 2.7 mmol/L, alternatively about 2.8 mmol/L, alternatively about 2.9 mmol/L. The second default scale may be about 0 to about 6.0 mmol/L. The graph may stay at the second default range unless the user does not access the application for a predetermined period time, after which it will reset the y-axis to the first default scale.

If certain biosensor readings are lost and there is a gap in the data, a gap may appear in the ketone curve 2076 for the time period with the gap. Moreover, the gap may be annotated with a time and an indication that "no data" was measured or received.

The live home screen GUIs 2070, 2090 may also display the daily average 2078, total hours in ketosis for that day 2080, and total hours above target for that day 2082.

The user may select a log button 2098 or link to access the log filter. As seen in FIG. 15D, the log filter 2114 may appear as a pop-up screen in which the user may select which icons they want to see on the ketone curve 2076. The activities included in the log filter 2114 may include, but are not limited to, food and drink 2116, fasting 2118, exercise 2120, mood 2122, appetite 2124, and energy 2128. The user may select one or more of the categories by selecting the button or icon for that category. After closing the log filter 2114, the entries of the selected categories will appear in the live screen along the ketone curve 2076 for that day at the time associated with the log entry (see, e.g., icons 2152*a, b* in FIG. 15B). If the user clicks on a particular icon, additional details that were logged for that entry may appear. For example, a type of food that was consumed and a picture of the food if it was added in the log entry may appear, along with the time associated with the entry.

Moreover, various GUIs of the ketone diet application may include a share link 1050 to enable sharing of various data or information.

Once a sensor has ended, the banner 1002 may include a statement 1010 to start a new biosensor. If the sensor is note replaced for a plurality of days, when the user scrolls to past days, the live screen for the previous day when the sensor was last active may appear. Days when the sensor was inactive may be skipped.

When the user is not browsing the ketone application or when the ketone application is in the background or closed, notifications may appear on the device, e.g., on the lock screen. In some embodiments, the notification may indicate that "Your Biosensor is ready" and suggest that the user start monitoring their real-time ketone level. In some embodiments, the notification may be related to ketone levels reaching ketosis and indicate that "You've reached ketosis!"

and suggest that the user see their real-time ketone level. In some embodiments, the notification may be related to ketone levels being out of ketosis and indicate "Uh-Oh! You dropped out of ketosis" and suggest that the user find out how to get back into ketosis. In some embodiments, the notification may indicate that "Your Biosensor ends in 24 hours" and suggest that the user order a new biosensor to keep learning about their body.

Flags

Figure 15E:
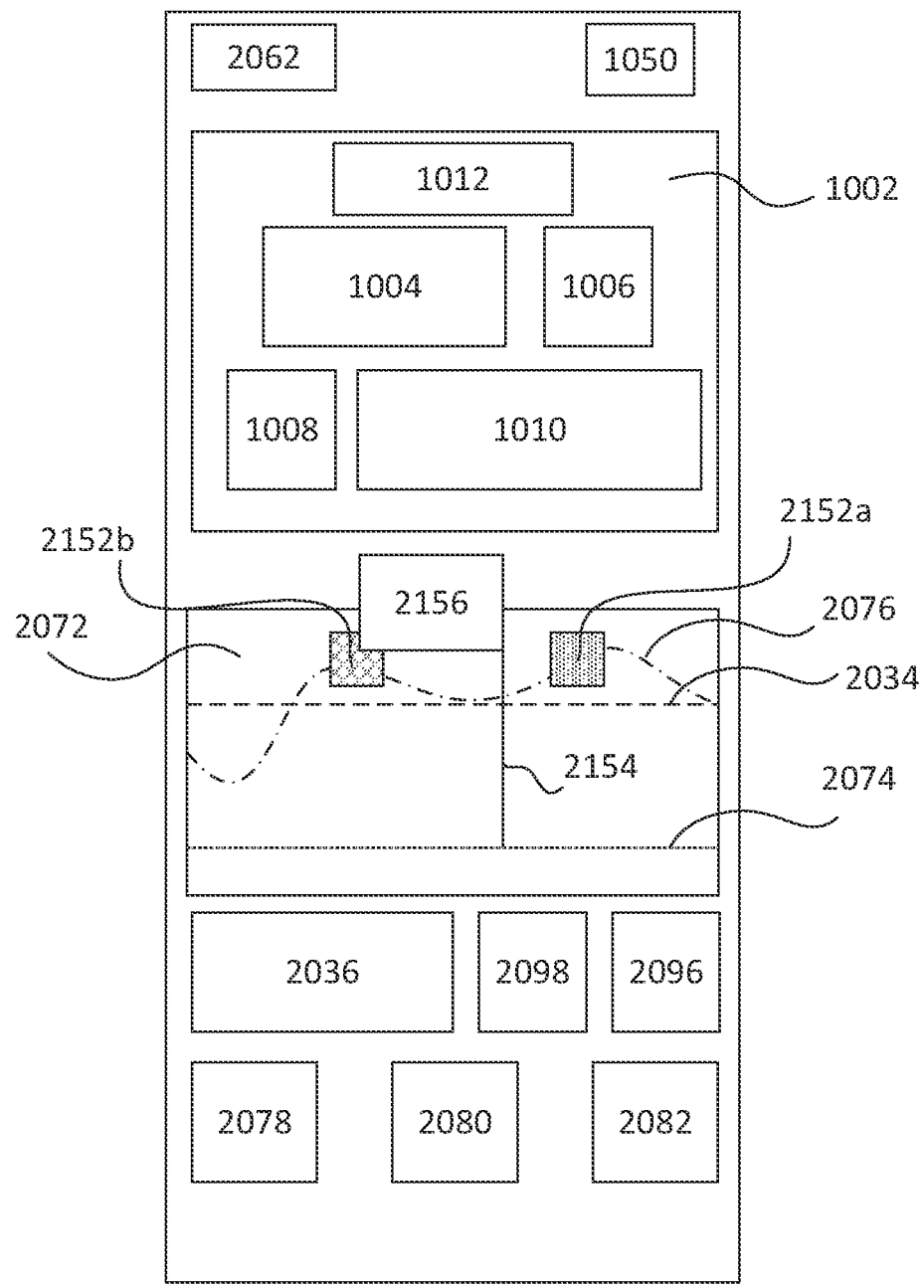
FIG. 15E is a block diagram depicting an example embodiment of a GUI including a flag.
Figure 15F:
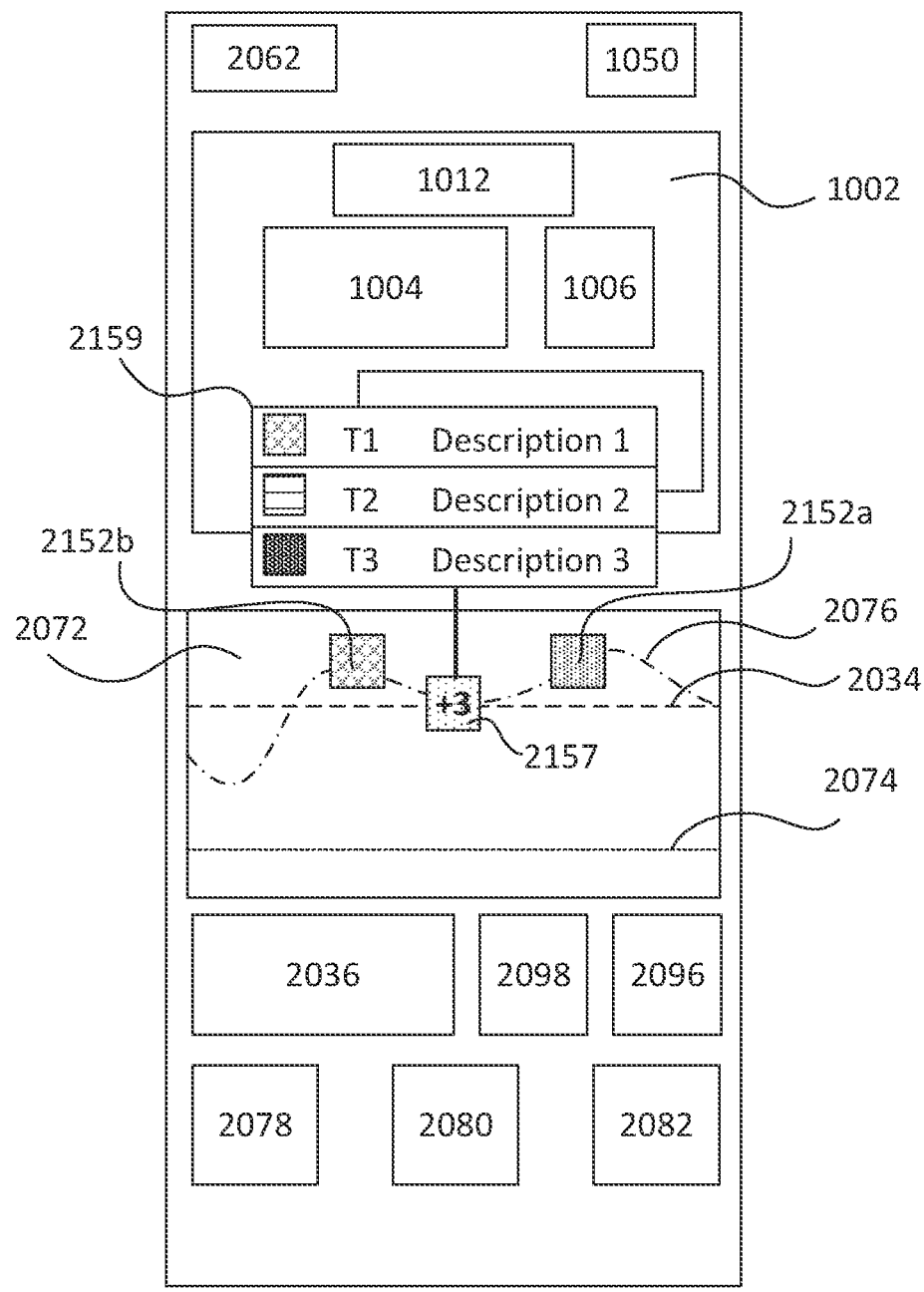
FIG. 15F is a block diagram depicting an example embodiment of a GUI including a tooltip.

As seen in FIG. 15E, a flag 2156 along with a line 2154 indicating the time on the graph that the flag corresponds to may appear if the user presses on the graph for a period of time. In response to a long press on the graph, the mobile device may vibrate and the flag 2156 may appear on the graph. The flag 2156 may include the ketone concentration at a particular time. If the concentration is below the low threshold or above the high threshold, the concentration may be reported as <low threshold or >high threshold, and the flag may additionally include the message that the exact reading is out of the biosensor's range. In some embodiments, the low threshold may be 0.3 mmol/L and the high threshold may be 6.0 mmol/L. If the concentration is between the low and high threshold, the flag may include the relevant time and numerical concentration value. As the user drags their finger across the graph, the flag may move along with the finger and display the concentrations for the different times. The phone may vibrate briefly as the flag moves from point to point. The flag may disappear if the user releases their finger from the graph, e.g., stops pressing on the graph. The flag may also disappear if the flag encounters an empty space or gap in the graph.

Logs

Food and Drink

If the user wants to log an event, they may select the log icon or button 2098 and select the type of log entry.

Figure 16A:
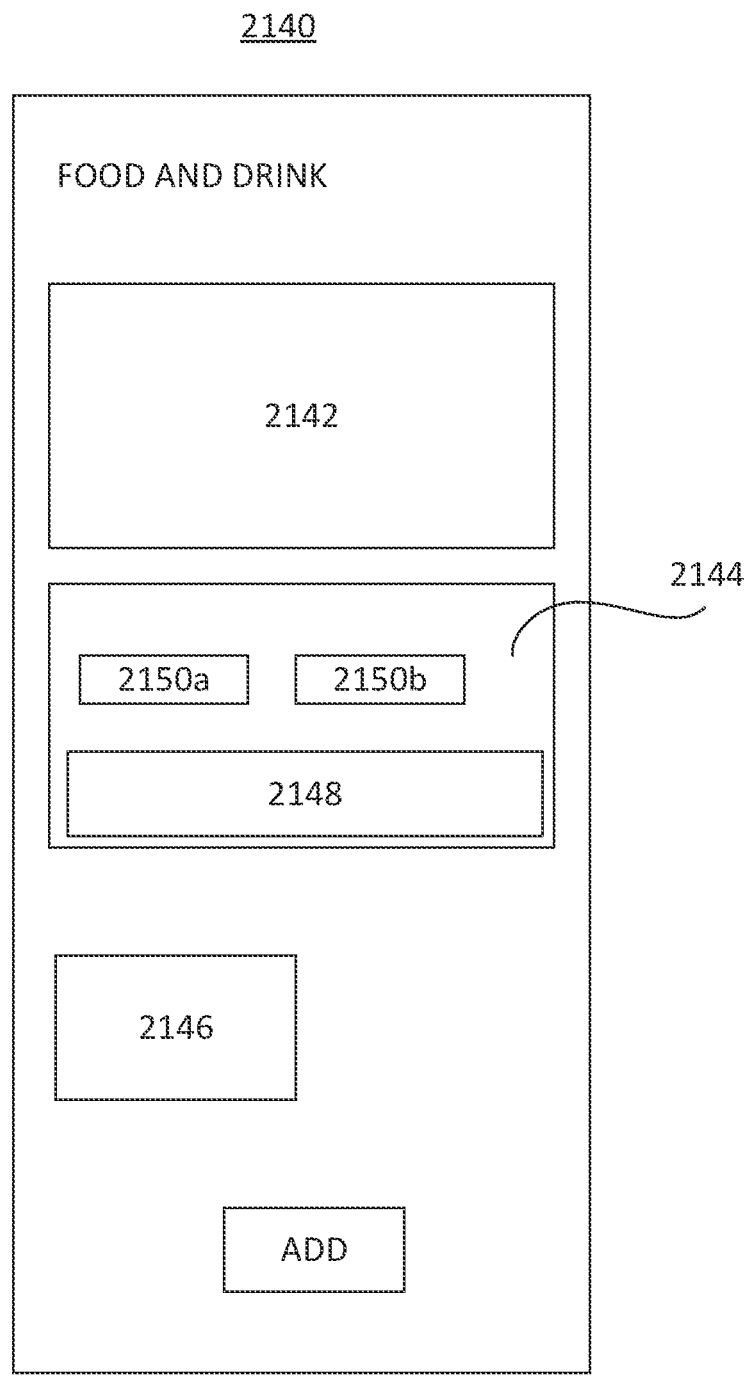
FIGS. 16A-16B are block diagrams depicting example embodiments of GUIs related to log entries for food and drink.

When a user wants to add a food and/or drink, they can select the food and drink icon and a GUI 2140 may appear, as seen in FIG. 16A. The food and drink GUI 2140 may include a section for setting the date and time 2142, a description of what was consumed (food or drinks) 2144, and a link to add photos 2146. In the time and date section 2142, the user may set the date and time by entering a date and time or by spinning a wheel and selecting the date and time. In the food and drink section 2144, the ketone diet application may ask the user what did they eat/drink and provide a text entry field 2148 for the user to enter a description of the food and drink that they just consumed. The user may enter a single food or drink in the text entry field 2148 at a time (e.g., "coconut wrap," "hamburger," or "apple cider vinegar"). After the user enters the item, it may appear as a tag cloud 2150a, which is deletable if the user wishes to edit the entry. The user may then enter another item that was consumed, which may also appear as a tag cloud 2150b. Thus, multiple food and drink entries may be associated with this time entry.

Figure 16B:
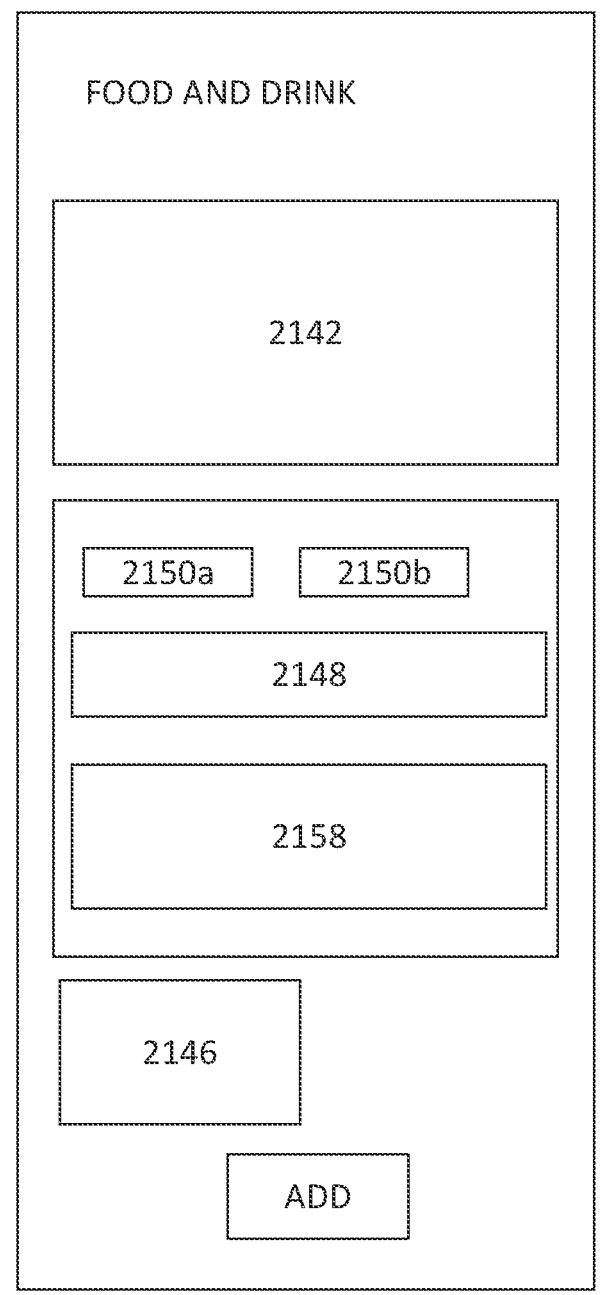

For return users (i.e., after the user has already been using the ketone diet application and has logged some entries), as seen in GUI 2160 in FIG. 16B, when the user enters a new food and drink entry, a list of suggested entries 2158 may appear as the user begins typing. The list of suggested entries 2158 may focus down as more letters are entered to only include the letters that have been typed. For example, if the user begins typing a "C", the list may include words that begin with "C" such as "Canned sardines," "Cheese shell tacos," "Coconut cookie," "Coconut ice cream," and "Coconut wrap." If the user then types an "o" such that the first two letters are "Co", the list 2158 no longer contains the entries that do not begin with "Co" (e.g., "Canned sardines" and "Cheese shell tacos" no longer appear), and only includes the entries that begin with "Co" (e.g., "Coconut cookie," "Coconut ice cream," and "Coconut wrap"). The entries that appear may be entries that the user has previously entered or may be from a general list of food and drinks. As described above, the entered or selected items appear as a tag cloud 2150a, 2150b associated with this time.

The user may then type in another item (e.g., "apple cider vinegar") or select an item from a prepopulated list 2158 as described above. Thus, multiple food and drinks may be associated with this time entry.

Food and drink GUIs 2140 and 2160 may also contain a link to add a photo or photos to associate with this entry. The user may also associate a photo with this entry. The user may select button 2146 and either take a photo of the item or access a photo from their picture gallery. The photos associated with this entry may appear as deletable entries, similar to the tag clouds listing of food and drinks.

After the user enters all of the relevant data and adds the entry to the log, e.g., by selecting "add", a food icon (see, e.g., icon 2152a of FIG. 15B) may appear on the ketone curve 2076 in the live home screen 2070. If the user taps the food icon, additional details may appear in a pop-up, such as the time and food or drink consumed or an abbreviated description of the food or drink consumed. A message may also appear on the live home screen 2070, 2090 indicating that Food and Drink have been added when the icon first appears on the ketone curve 2076. In some instances, the message may appear as a drop-down notification. If the user selects the pop-up description or double taps the food icon, the food and drink entry may open and the user may edit the entry as needed, e.g., by changing the time associated with the entry.

Fasting

If the user wants to log an event, they may select the log icon or button 2098 and select the type of log entry.

When a user wants to add a fasting entry, they may select the fasting icon or entry and a GUI 2170 may appear.

Figure 17A:
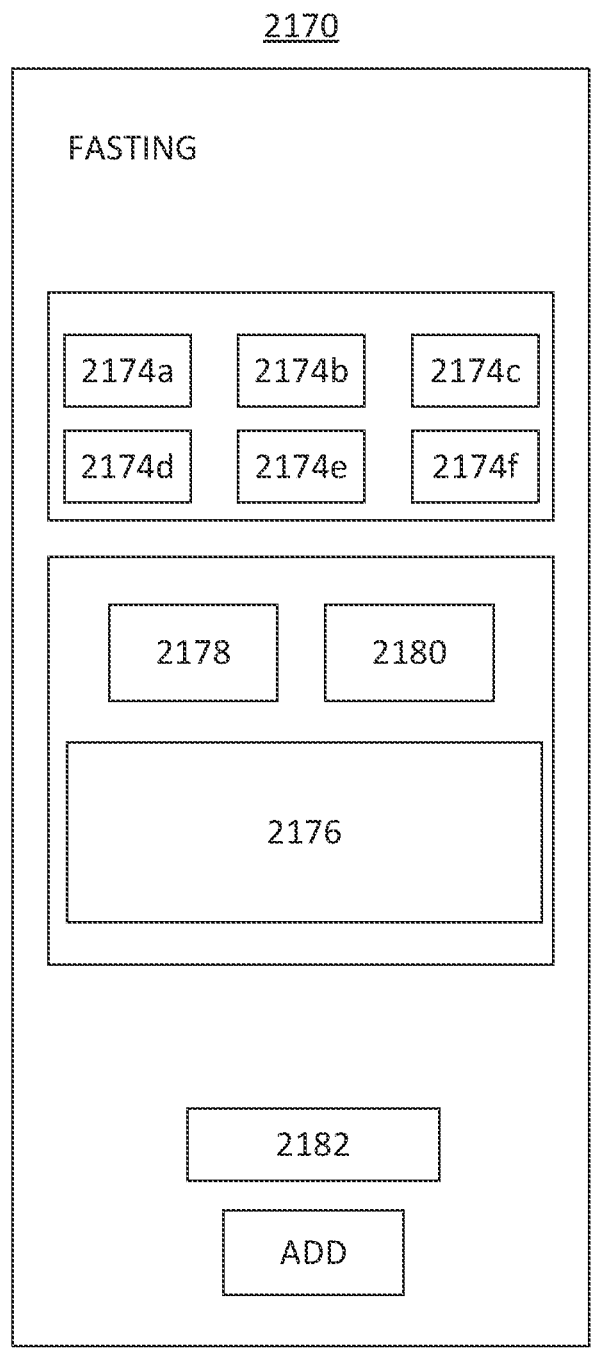
FIGS. 17A-17C are block diagrams depicting example embodiments of GUIs related to log entries for fasting.

The fasting GUI 2170, as seen in FIG. 17A, may include a plurality of preset time intervals 2174a-f that the user may select. The preset time intervals 2174a-f may be, but are not limited to, none, 13 hours, 16 hours, 18 hours, 20 hours, and 36 hours. The user may select the start time of the fasting period by, e.g., selecting the date and time on a wheel 2176 or by entering the date and time manually. The start time 2178 may appear as entered and the end time 2180 may populate automatically based on the selected preset time interval. Alternatively, the user may set both the start and end times by selecting "none" as the preset time interval. The fasting GUI 2170 may contain an additional message 2182 stating how long the fasting period is for this entry, e.g., "fast for 16 h."

After the user enters all of the relevant data and adds the entry to the log, e.g., by selecting "add", a fasting icon (see, e.g., icon 2152b of FIG. 15B) may appear on the ketone curve 2076 in the live home screen 2070, 2090. Moreover, in some embodiments, a color of the gradient below the ketone curve 2076 for the fasting period (start to end time) may be distinguishable from non-fasting periods. For example, the area under the ketone curve 2076 for the fasting period may not be as transparent as the non-fasting period, may not be a gradient, or may be a different color or pattern.

If the user taps the fasting icon, additional details related to the fasting entry may appear, such as start and end times and/or the duration of the fast. A message may also appear on the live home screen 2070, 2090 indicating that fasting has been added when the icon first appears on the ketone curve 2076. In some instances, the message may appear as a drop-down notification. If the user double taps the fasting icon, the fasting entry may open and the user may edit the entry as needed, e.g., by changing the duration of the fasting period.

Figure 17B:
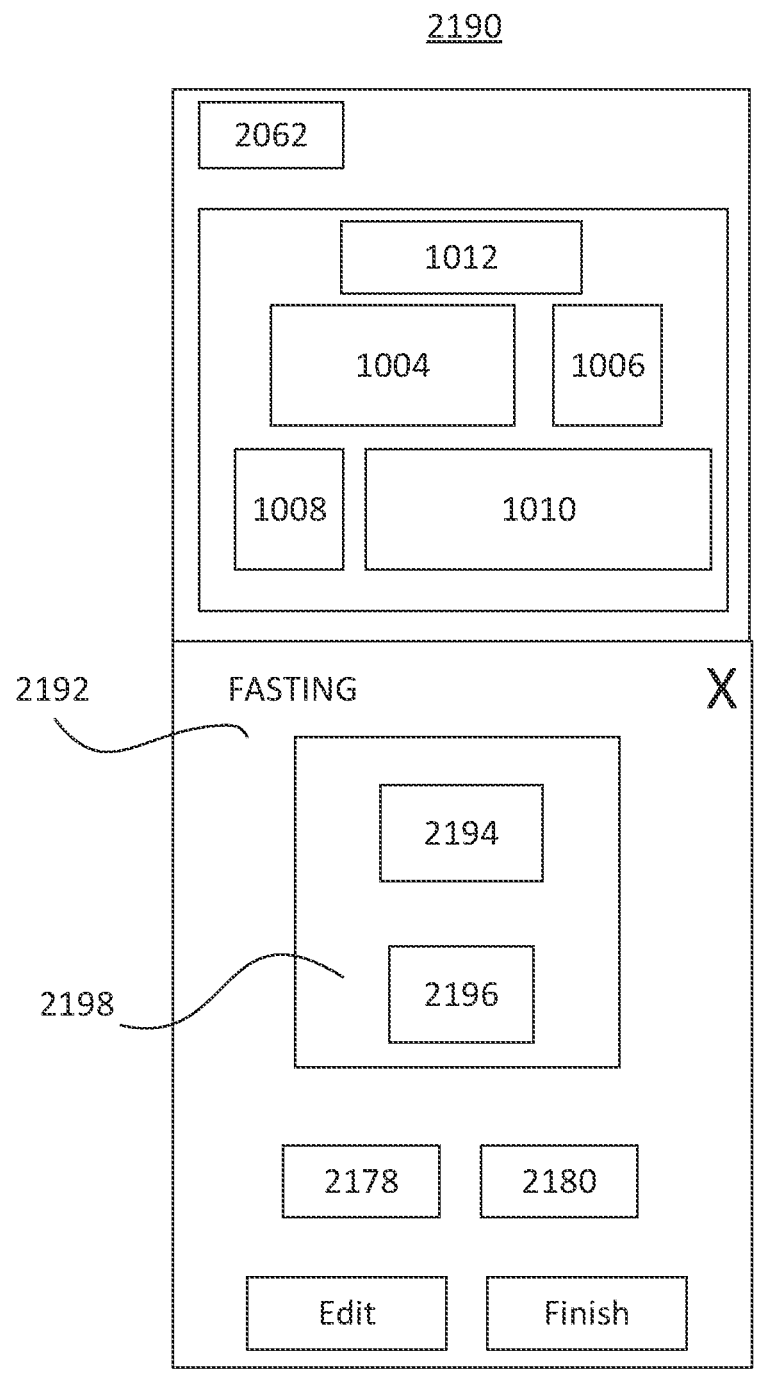

If the user taps on the abbreviated description, as seen in GUI 2190 of FIG. 17B, a pop-up screen or window 2192 may appear that shows the elapsed time 2194, the goal time 2196, the start time 2178, the end time 2180, and a graphic having a progress indicator 2198. The graphic having a progress indicator 2198 may be a bar having a colored portion or may be a colored portion along the perimeter of a circle, where the colored portion is proportional to the amount of time elapsed of the goal time. If the user taps "edit" on GUI 2190, the edit GUI 2170 may appear and the user can change the entry.

Figure 17C:
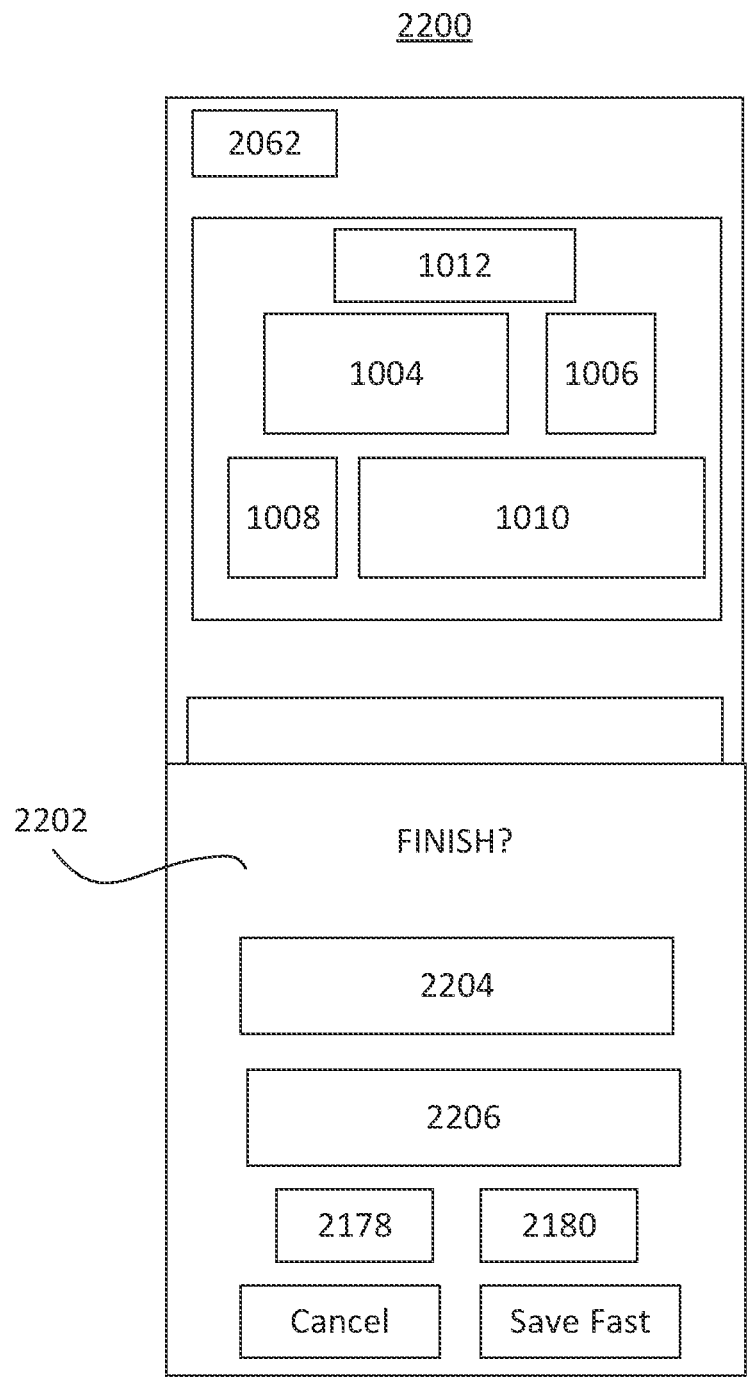

If the user taps "finish", as seen in GUI 2200 of FIG. 17C, another pop-up screen 2202 may appear that asks the user if they have finished fasting. The pop-up screen 2202 may also report to the user what percentage of their goal that they have met in a statement or graphic 2204 and how long they have fasted in hours and minutes 2206. The pop-up screen 2202 may also report the start time 2178 and end time 2180.

Exercise

If the user wants to log an event, they may select the log icon or button 2098 and select the type of log entry.

Figure 18A:
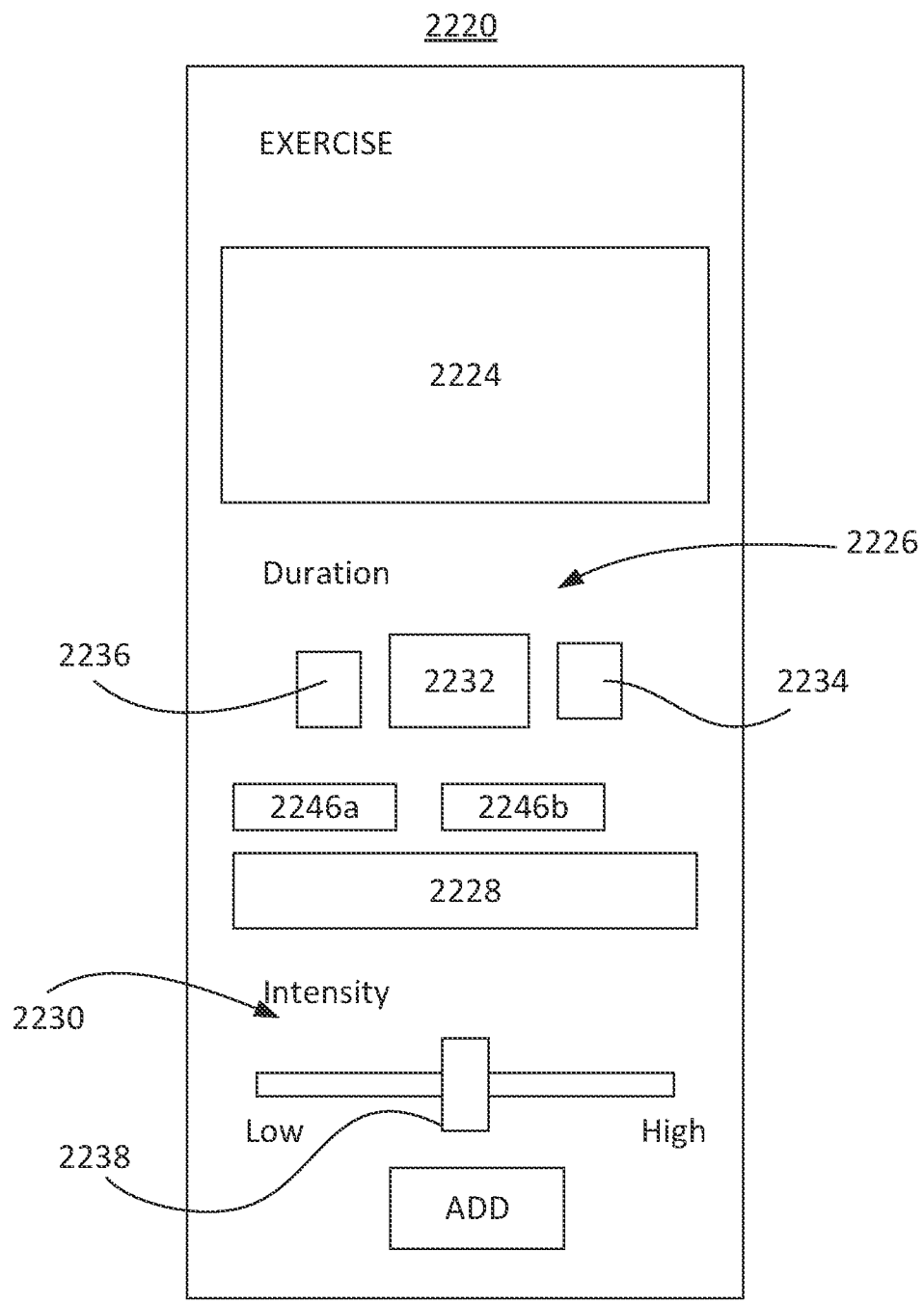
FIGS. 18A-18B are block diagrams depicting example embodiments of GUIs related to log entries for exercise.

When a user wants to add an exercise entry, they may select the exercise icon or entry and a GUI 2220 may appear, as seen in FIG. 18A. The exercise GUI 2220 may include a section for setting the date and start time 2224, a duration of the exercise period 2226, a section to enter what exercise was performed 2228, and a section to indicate the intensity of the exercise 2230. In the time and date section 2224, the user may set the date and time by entering a date and start time or by spinning a wheel and selecting the date and time. The user may set the duration of the exercise 2226 by typing in a number of hours and/or minutes or by tapping a "+" or "−" button 2234, 2236 to add minutes in certain increments, e.g., increments of 5 minutes, 10 minutes, 15 minutes, or 30 minutes, where a total number of minutes 2232 is also displayed.

The ketone diet application may also have a section 2228 for the user to enter the type of exercise performed, e.g., in response to a question of "What exercise did you do?". The user may add a description of the type of exercise in a text entry field. The description may include one or more types of exercise (e.g., "boxing," "jogging," "yoga"). After the user enters the type of exercise, it may appear as a tag cloud 2246a, 2246b, which is deletable if the user wishes to edit the entry. The user may then enter another type of exercise, which may also appear as a tag cloud. Thus, multiple types of exercise be associated with this time entry.

The ketone diet application may also have a section 2230 for the user to indicate the intensity of the exercise performed. In one embodiment, the user may slide a switch 2238 along a spectrum of Low to Medium to High. In another embodiment, the user may select, Low, Medium, or High buttons. Or the user may rate the intensity with a letter grade or a number (e.g., a "1" would indicate low intensity and a "5" would indicate "medium intensity" and a "10" would indicate high intensity).

Figure 18B:
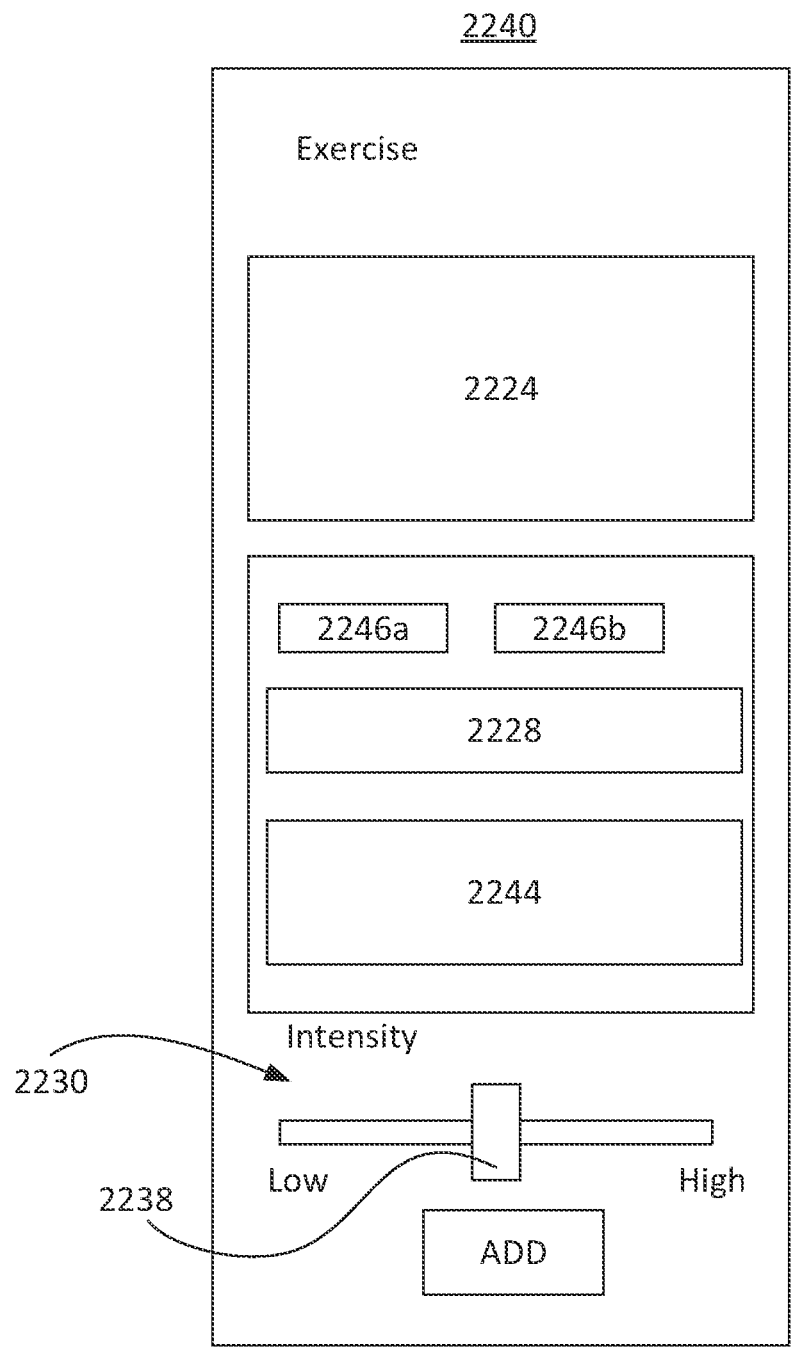

For return users, as seen in GUI 2240 of FIG. 18B, a list of previously entered exercises 2244 may appear that the user may select for quick entry. If any item is selected from a default history list (e.g., the most recent 5 exercises entered), then the selected item may disappear from the list 2244 and the most recent $6^{th}$ item may appear in the list 2244 to replace it. If the user does not select a listed entry, and the user begins to type the new item, a list of suggested entries may appear as the user begins typing. The list may focus down as more letters appear to only include the letters that have been typed. For example, if the user begins typing a "J", the list may include words that begin with "J" such as "Jogging" and "Jump rope." Once the user types in an entry, the entry may appear as a tag cloud 2246a, 2246b, which is deletable if the user wishes to edit the entry.

After the user enters all of the relevant data and adds the entry to the log, e.g., by selecting "add," an exercise icon (see, e.g., icon 2152a or 2152b of FIG. 15B) may appear on the ketone curve 2076 in the live home screen 2070, 2090. Moreover, in some embodiments, a color of the gradient below the ketone curve 2076 for the exercise period may be distinguishable from non-exercise periods. For example, the area under the ketone curve 2076 for the exercise period may not be as transparent as the non-exercise period, may not be a gradient, or may be a different color or pattern.

If the user taps on the exercise icon, additional details related to the exercise entry may appear, such as the time and duration of the exercise or an abbreviated description of the exercise performed. A message may also appear on the live home screen 2070, 2090 indicating that exercise has been added when the icon first appears on the ketone curve 2076. In some instances, the message may appear as a drop-down notification. If the user double taps the exercise icon, the exercise entry 2220 may open and the user may edit the entry as needed, e.g., by changing the duration of the exercise period. In some embodiments, after double tapping the icon, the beginning and ending borders of the exercise period may be dragged forward or backward to adjust the end points of the exercise period quickly. Alternatively, the edit screen may appear and the user may adjust the start time, the end time, and/or the duration selected.

Mood

If the user wants to log an event, they may select the log icon or button 2098 and select the type of log entry.

Figure 19A:
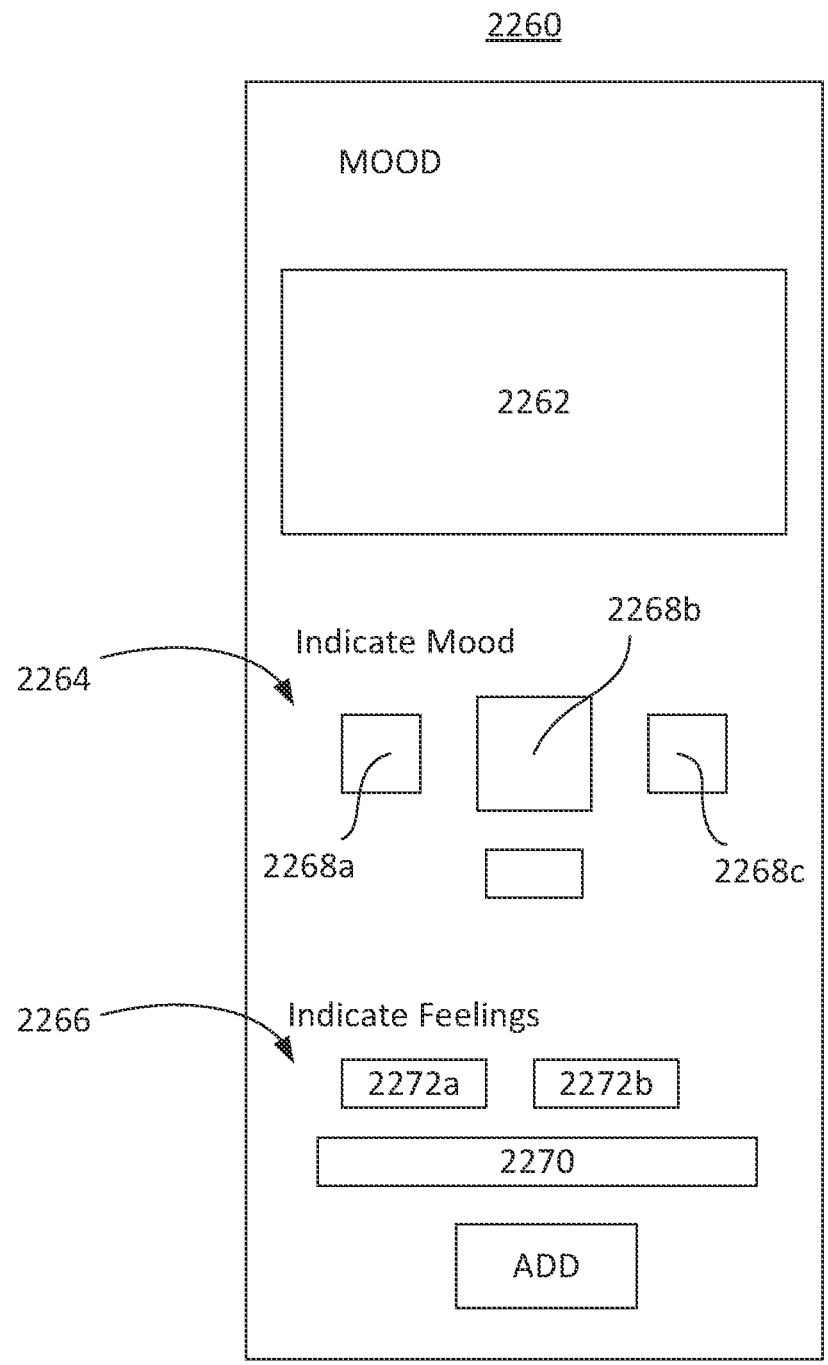
FIGS. 19A-19B are block diagrams depicting example embodiments of GUIs related to log entries for mood.

When a user wants to add a mood entry, they can select the mood icon and a GUI 2260 may appear, as seen in FIG. 19A. The mood GUI 2260 may include a section for setting the date and time 2262, a section to enter the user's mood 2264, and a section to enter the user's feeling 2266. In the time and date section 2262, the user may set the date and time by entering a date and time or by spinning a wheel and selecting the date and time.

In the mood section 2264, the ketone diet application may ask the user "How is your mood?" and the user may select from a plurality of emojis 2268a-2268c indicating different moods and may range from, but are not limited to, great, good, okay, bad, or awful. The plurality of emojis may be presented in a carousel for the user's selection. Alternatively, the user may type in a description for the mood (not shown).

In the mood section 2266, the ketone diet application may ask the user "How would you describe your feeling?" and the ketone diet application may provide a text entry field 2270 for the user to enter a description of a feeling that are experiencing. The user may enter a single feeling in the text entry field 2270 at a time (e.g., "excited"). After the user enters the feeling, it may appear as a tag cloud 2272a, which is deletable if the user wishes to edit the entry. The user may then enter another feeling (e.g., "confident"), which may also appear as a tag cloud 2272b. Thus, multiple feelings may be associated with this time entry.

Figure 19B:
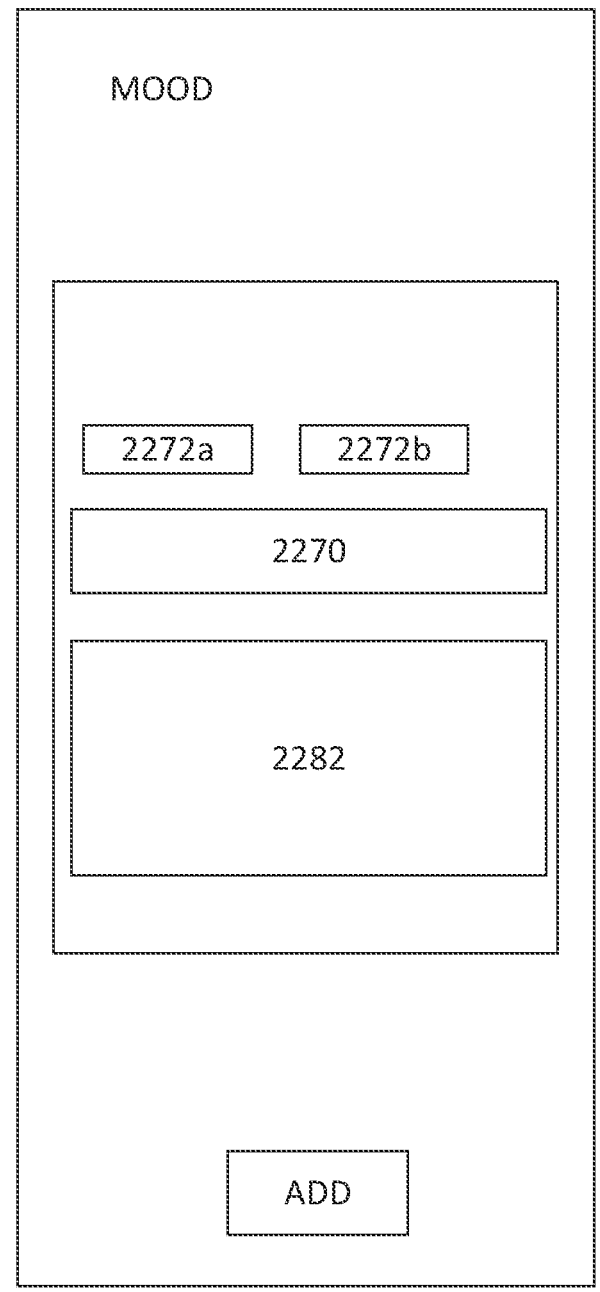

For return users, as seen in GUI 2280 of FIG. 19B, a list of previously entered feelings 2282 may appear that the user may select for quick entry. If any item is selected from a default history list (e.g., the most recent 5 feelings entered), then the selected item may disappear from the list 2282 and the most recent 6$^{th}$ item may appear in the list 2282 to replace it. If the user does not select a listed entry, and the user begins to type the new item, a list of suggested entries may appear as the user begins typing. The list may focus down as more letters appear to only include the letters that have been typed. For example, if the user begins typing an "E", the list may include words that begin with "E" such as "Emotional" and "Excited." Once the user types in an entry, the entry may appear as a tag cloud 2272a, 2272b, which are deletable if the user wishes to edit the entry. The user may then type in another feeling (e.g., confident) or select a feeling from a prepopulated list 2282 as described above. Thus, multiple feelings may be associated with this time entry.

After the user enters all of the relevant data and adds the entry to the log, e.g., by selecting "add", a mood icon (see, e.g., icon 2152b of FIG. 15B) may appear on the ketone curve 2076 in the live home screen 2070.

If the user taps on the mood icon, additional details may appear in a pop-up, such as the time of the entry and/or an abbreviated description of the mood entered. A message may also appear on the live home screen 2070, 2090 indicating that Mood has been added when the icon first appears on the ketone curve 2076. In some instances, the message may appear as a drop-down notification. If the user selects the pop-up description or double taps the mood icon, the mood entry GUI may open and the user may edit the entry as needed, e.g., by changing the time associated with the entry or the current mood or feelings.

Energy

If the user wants to log an event, they may select the log icon or button 2098 and select the type of log entry.

Figure 20A:
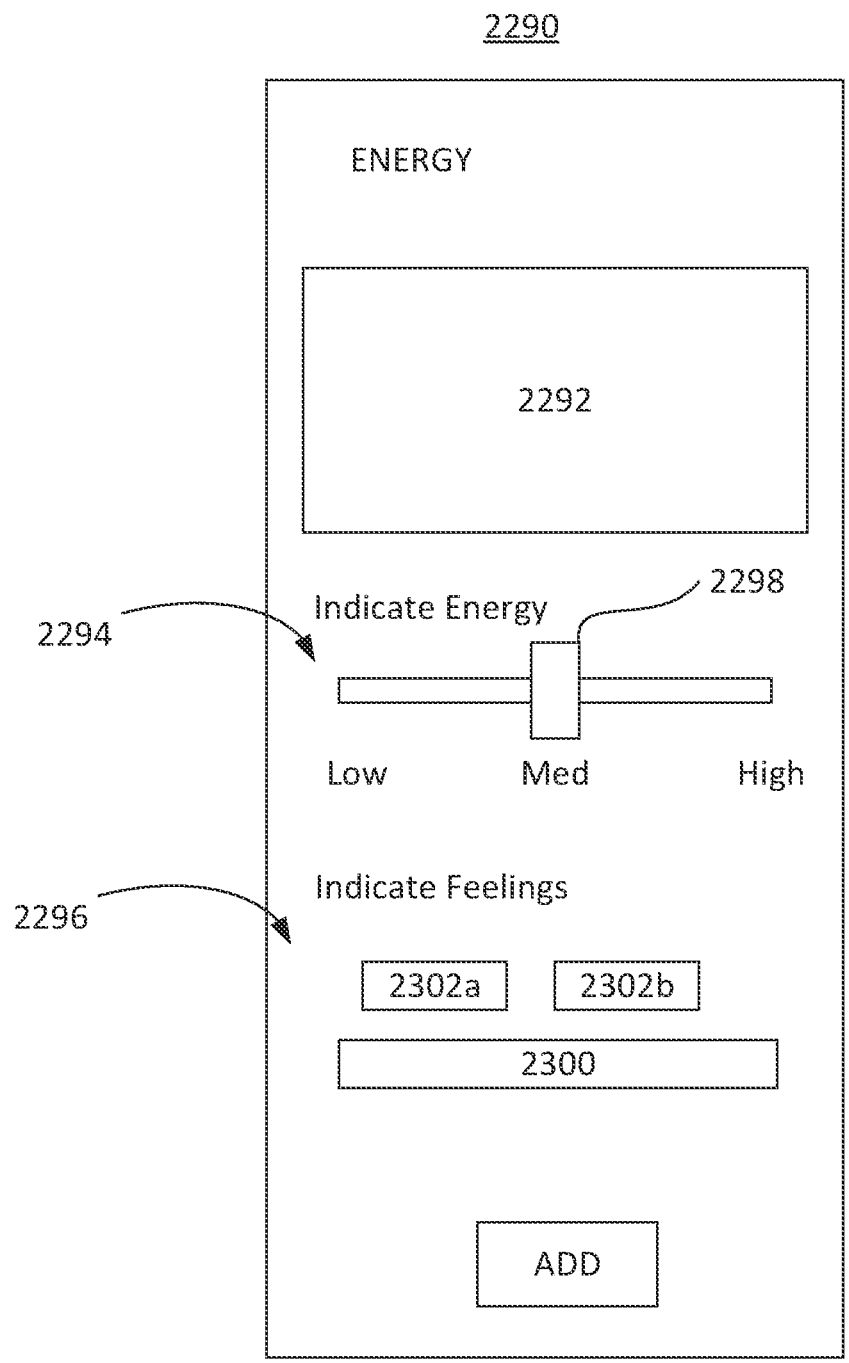
FIGS. 20A-20B are block diagrams depicting example embodiments of GUIs related to log entries for energy.

When a user wants to add an energy level entry, they can select the energy icon and a GUI 2290 may appear, as seen in FIG. 20A. The energy GUI 2290 may include a section for setting the date and time 2292, a section to enter the user's energy level 2294, and a section to enter the user's feeling 2296. In the time and date section 2262, the user may set the date and time by entering a date and time or by spinning a wheel and selecting the date and time.

The ketone diet application may also have a section 2294 for the user to indicate the user's energy level at the selected time. In one embodiment, the user may slide a switch 2298 along a spectrum of Low to Medium to High. In another embodiment, the user may select, Low, Medium, or High buttons. Or the user may rate the energy level with a letter grade or a number (e.g., a "1" would indicate low energy and a "5" would indicate "medium energy" and a "10" would indicate high energy).

As described with respect to other embodiments, the ketone diet application may also ask the user "How would you describe your feeling?" and the ketone diet application may provide a text entry field 2300 for the user to enter a description of a feeling that are experiencing. The user may enter a feeling in the text entry field 2300 at a time (e.g., "excited"). After the user enters the feeling, it may appear as a tag cloud 2302a, which is deletable if the user wishes to edit the entry. The user may then enter another feeling (e.g., "caffeine-free"), which may also appear as a tag cloud 2302b. Thus, multiple feelings may be associated with this energy entry.

Figure 20B:
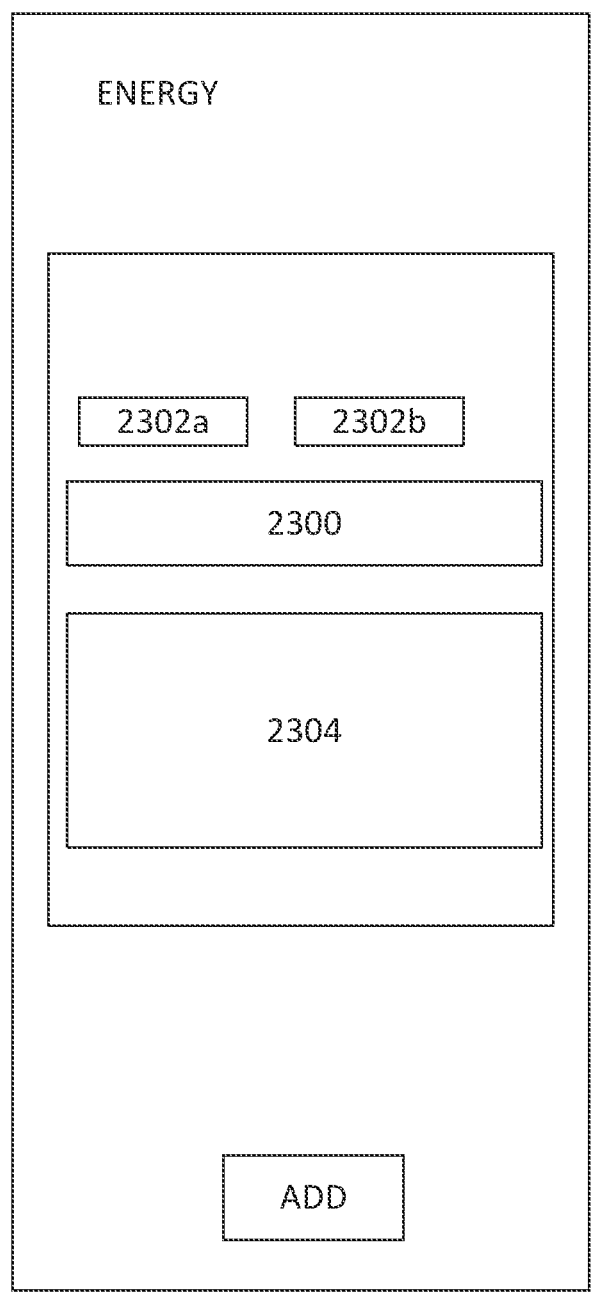

As described with respect to other embodiments, for return users, as seen in GUI 2310 of FIG. 20B, which may appear as a pop-up window or another screen, a list of previously entered feelings 2304 may appear that the user may select for quick entry. If any item is selected from a default history list (e.g., the most recent 5 feelings entered), then the selected item may disappear from the list 2304 and the most recent 6$^{th}$ item may appear in the list 2304 to replace it. If the user does not select a listed entry, and the user begins to type the new item, a list of suggested entries may appear as the user begins typing. The list may focus down as more letters appear to only include the letters that have been typed. For example, if the user begins typing an "E", the list may include words that begin with "E" such as "Emotional" and "Excited." Once the user types in an entry, the entry may appear as a tag cloud 2302a, 2302b, which are deletable if the user wishes to edit the entry. The user may then type in another feeling (e.g., confident) or select a feeling from the prepopulated list 2304 as described above. Thus, multiple feelings may be associated with this time entry.

After the user enters all of the relevant data and adds the entry to the log, e.g., by selecting "add", an energy icon (see, e.g., icon 2152a or 2152b of FIG. 15B) may appear on the ketone curve 2076 in the live home screen 2070.

If the user taps on the energy icon, additional details may appear in a pop-up, such as the time of the entry and/or an abbreviated description of the energy state entered. A message may also appear on the live home screen 2070, 2090 indicating that energy has been added when the icon first appears on the ketone curve 2076. In some instances, the message may appear as a drop-down notification. If the user selects the pop-up description or double taps the energy icon, the energy entry may open and the user may edit the entry as needed, e.g., by changing the time associated with the entry or the current energy level or feelings.

Appetite

If the user wants to log an event, they may select the log icon or button 2098 and select the type of log entry.

Figure 21A:
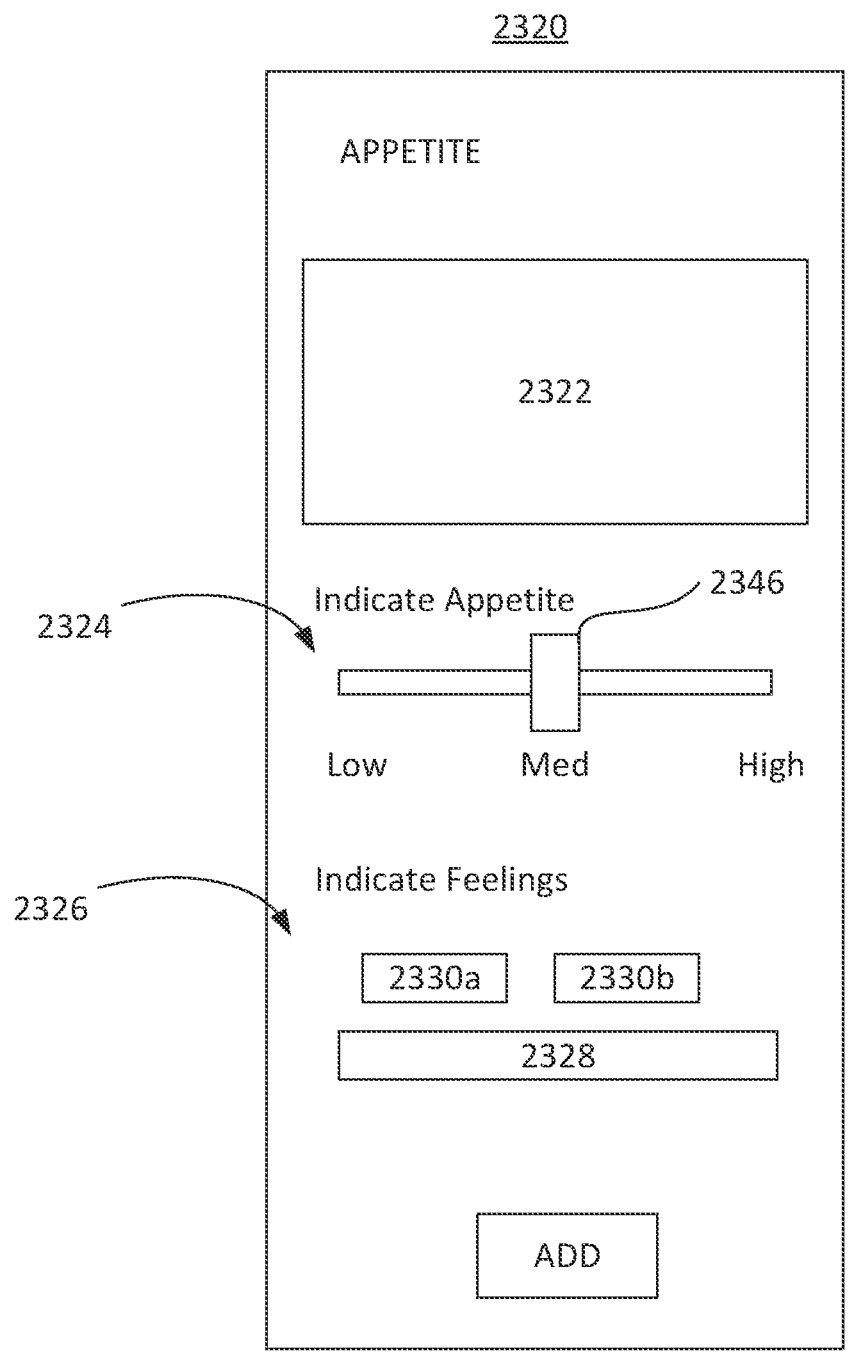
FIGS. 21A-21B are block diagrams depicting example embodiments of GUIs related to log entries for appetite.

When a user wants to add an energy level entry, they can select the appetite icon and a GUI 2320 may appear, as seen in FIG. 21A. The appetite GUI 2320 may include a section for setting the date and time 2322, a section to enter the user's appetite level 2324, and a section to enter the user's feeling 2326. In the time and date section 2322, the user may set the date and time by entering a date and time or by spinning a wheel and selecting the date and time.

The ketone diet application may also have a section 2324 for the user to indicate the user's appetite level at the selected time. In one embodiment, the user may slide a switch 2346 along a spectrum of Low to Medium to High. In another embodiment, the user may select, Low, Medium, or High buttons. Or the user may rate the appetite level with a letter grade or a number (e.g., a "1" would indicate low appetite and a "5" would indicate a medium appetite and a "10" would indicate high or large appetite).

As described with respect to other embodiments, the ketone diet application may also ask the user "How would you describe your feeling?" and the ketone diet application may provide a text entry field 2328 for the user to enter a description of a feeling that are experiencing. The user may enter a single feeling in the text entry field 2328 at a time (e.g., "excited"). After the user enters the feeling, it may appear as a tag cloud 2330a, which is deletable if the user wishes to edit the entry. The user may then enter another feeling (e.g., "caffeine-free"), which may also appear as a tag cloud 2330*b*. Thus, multiple feelings may be associated with this energy entry.

Figure 21B:
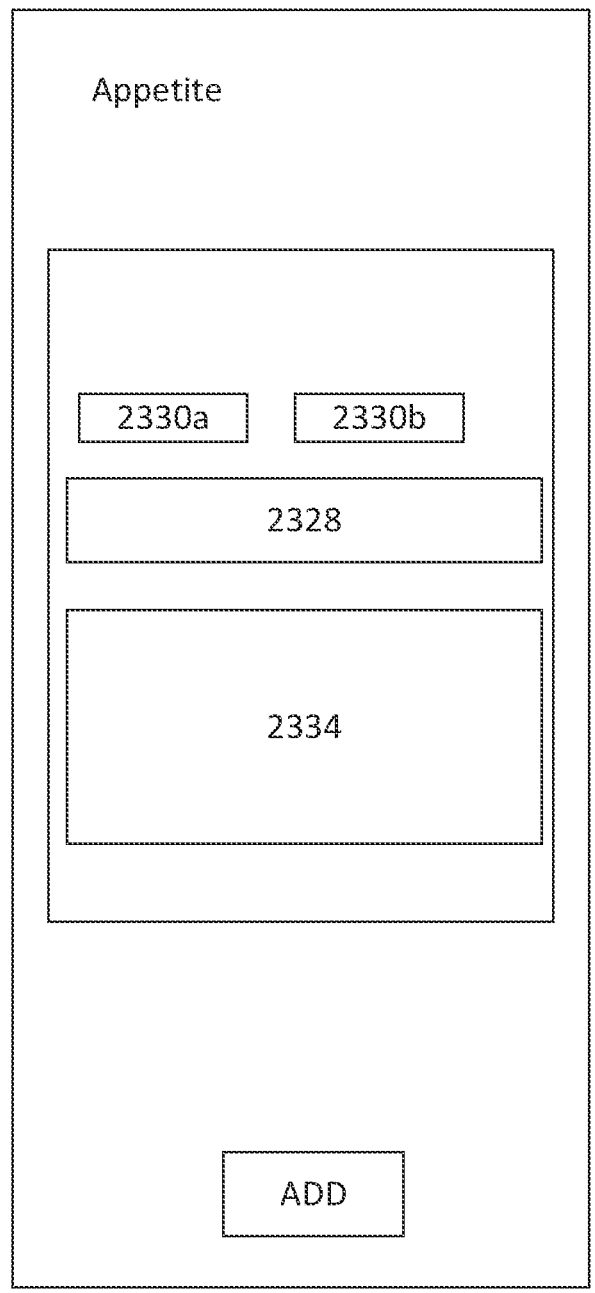

As described with respect to other embodiments, for return users, as seen in GUI 2340 of FIG. 21B, a list of previously entered feelings 2334 may appear that the user may select for quick entry. If any item is selected from a default history list (e.g., the most recent 5 feelings entered), then the selected item may disappear from the list 2334 and the most recent 6$^{th}$ item may appear in the list 2334 to replace it. If the user does not select a listed entry, and the user begins to type the new item, a list of suggested entries may appear as the user begins typing. The list may focus down as more letters appear to only include the letters that have been typed. For example, if the user begins typing an "E", the list may include words that begin with "E" such as "Emotional" and "Excited." Once the user types in an entry, the entry may appear as a tag cloud 2330*a*, 2330*b*, which is deletable if the user wishes to edit the entry. The user may then type in another feeling (e.g., confident) or select a feeling from a prepopulated list 2334 as described above. Thus, multiple feelings may be associated with this time entry.

After the user enters all of the relevant data and adds the entry to the log, e.g., by selecting "add", an appetite icon (see, e.g., icon 2152*a* or 2152*b* of FIG. 15B) may appear on the ketone curve 2076 in the live home screen 2070.

If the user taps on the appetite icon, additional details may appear in a pop-up, such as the time of the entry and/or an abbreviated description of the appetite state entered. A message may also appear on the live home screen 2070 indicating that Appetite has been added when the icon first appears on the ketone curve 2076. In some instances, the message may appear as a drop-down notification. If the user selects the pop-up description or double taps the appetite icon, the appetite entry may open and the user may edit the entry as needed, e.g., by changing the time associated with the entry or the current appetite level or feelings.

Learn and Explore

Figure 22A:
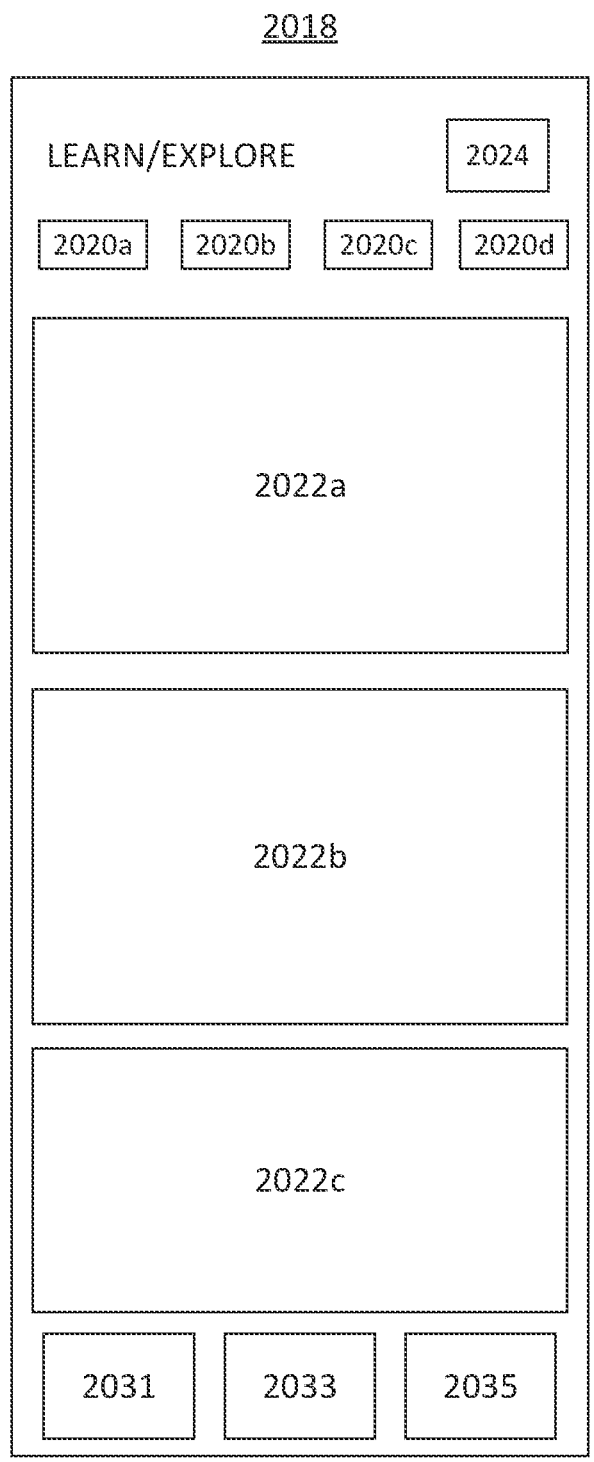
FIGS. 22A-22B are block diagrams depicting example embodiments of GUIs related to learning and exploring.

As seen in FIG. 22A, the user may tap a link to view a learn and explore GUI 2018, which provides additional information regarding various relevant topics. Learn and explore GUI 2018 may have a plurality of selectable tabs 2020*a*-2020*d*, each tab containing content regarding a different topic of interest. The subject matter of the plurality of selectable tabs 2020*a*-2020*d* may include, but are not limited to, content specific to the user (e.g., "for you"), basic content related to ketosis (e.g., "basic"), content related to food (e.g., "food"), content related to health (e.g., "health"), content related to lifestyle (e.g., "lifestyle), etc. Learn and explore GUI 2018 may also have a button 2024 that allows the user to bookmark or save the page for easy access at a later time. Any of the GUIs described herein may include links that can quickly take the user to the live screen 2031, to the learn and explore screens 2033, and to the settings 2035. In some embodiments, the link to the live screen 2031 may only appear active after the biosensor has finished warming up.

Under each selectable tab 2020*a*-2020*d*, a plurality of content may be displayed in selectable cards 2022*a*-2022*c*, including but not limited to, articles, photographs, text, graphs, tips, and summaries. For example, under the tab specific to the user, the content may include articles explaining how to get a person into ketosis, tracking and understanding ketosis levels, how to experiment with different foods and how the different foods affect ketone levels, an explanation of macronutrients, etc.

Figure 22B:
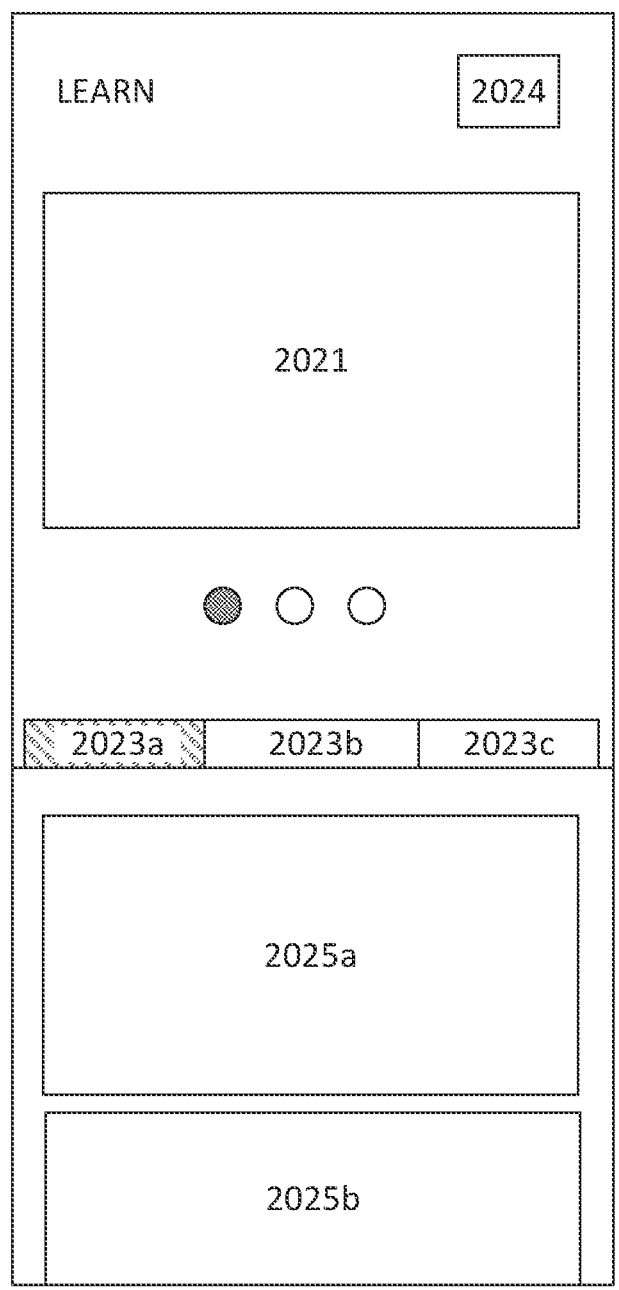

In some embodiments, as seen in FIG. 22B, the user may tap a link to view a learn GUI 2019, which provides additional information regarding various relevant topics. Learn GUI 2019 may have a carousel of cards 2021 that display different articles and content. The Learn GUI 2019 may also have different selectable tabs 2023*a*-2023*c* with articles or content grouped by category. The subject matter of the plurality of selectable tabs 2023*a*-2023*c* may include, but are not limited to, "Latest," "Get Started," "Ketosis," etc.

Under each selectable tab 2023*a*-2023*c*, a plurality of content may be displayed in selectable cards 2025*a*-2025*b*, including but not limited to, articles, photographs, text, graphs, tips, and summaries. For example, under the "Latest" tab, the content may include articles explaining what the application is about or a shopping guide.

The order of presentation of the content as seen in the displayed selectable cards 2022*a*-2022*c*, 2025*a*-2025*b* may vary. For example, if the host application is a keto diet application, in the beginning of the user experience, content related to getting started, learning about ketosis, and other basic information may be shown first to the user. As the ketone diet application gathers more data on the user, e.g., from answers to questions or prompts, from their ketone levels, or from patterns identified in their ketone data, the ketone diet application may personalize and tailor the content that is presented to the user. For instance, if the user has reached ketosis for several days, the ketone diet application may present an article to the user about the benefits of reaching ketosis. The ketone diet application may also seek input from the user at the end of the article or in another GUI to further personalize their experience.

Settings

Figure 24A:
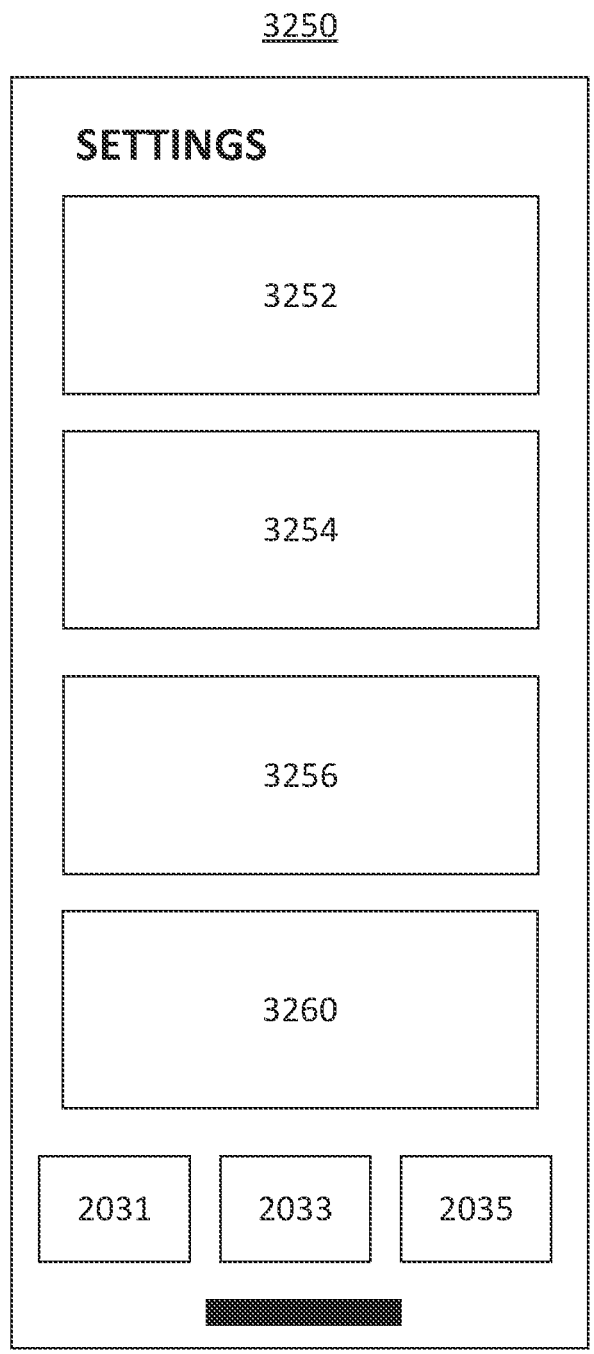
FIGS. 24A-24C are block diagrams depicting example embodiments of GUIs related to settings.

If the user taps the settings link 2035, as seen in FIG. 24A, a settings GUI may appear that includes sections relating to daily macro goals 3252, notifications 3254, ordering a biosensor 3256, and privacy and legal matters 3260.

If the user has finished the personalization process, the daily macro goals section 3252 may list the recommended total calories, the recommended amount of carbs, the recommended amount of protein, and the recommended amount of fat to get into ketosis quickly. If the user had previously skipped the personalization section, and if the user selects the daily macro goals section 3252, GUIs related to customizing the user's journey and setting goals, as described elsewhere with respect to e.g., FIGS. 13A-13F, may be displayed.

Figure 24B:
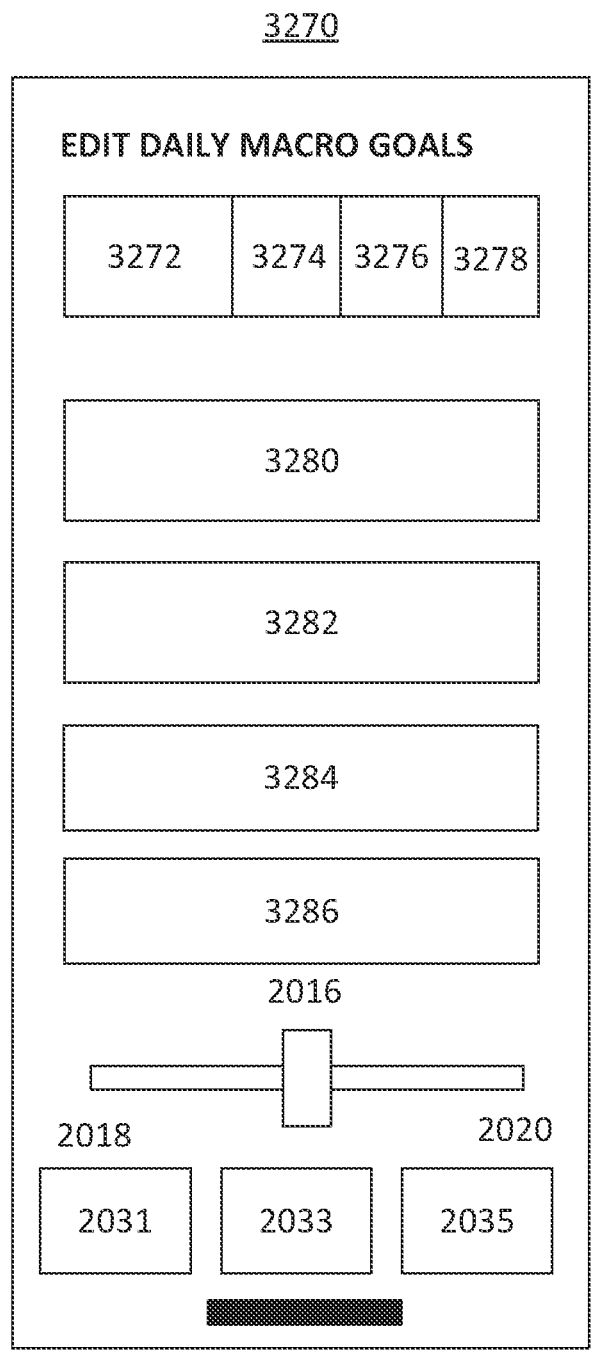

As seen in FIG. 24B, if the user selects or taps the daily macro goals section 3252, a daily macro goals GUI 3270 with editable fields may be presented. The GUI 3270 may display the recommended total calories 3272, the recommended amount of carbs 3274, the recommended amount of protein 3276, and the recommended amount of fat 3278 to get into ketosis quickly. The GUI 3270 may also include a goals section 3280, which states the user's goal that they entered during the personalization process. The goals section 3280 may include a drop down menu or a pop-up window that enables the user to change their goal. The goals may be lose weight, maintain weight, or gain weight. The goals section 3280 may optionally include a text box that enables the user to enter a custom goal. The GUI 3270 may also include a measurements section 3282, which lists the user's height and weight that was entered during the personalization process. The user may switch between metric and imperial units using a pull down menu or a pop-up window. The user may also enter new measurements by tapping the measurements section 3282, which will result in the display of a wheel in which the user can dial their new measurements or alternatively, a text box where the user can enter their new measurements. The GUI 3270 may also include a date of birth section 3284, which lists the user's date of birth that was entered during the personalization process. The user may also edit their date of birth by tapping the date of birth section 3284, which will result in the display of a wheel in which the user can dial a different date or alternatively, a text box where the user can enter a new date. The GUI 3270 may also include an activity level section 3286, which lists the activity level that was entered during the personalization process. The user may also change their activity level by tapping the activity level section 3286, which will result in the display of a pop-up window listing the activity level options. The GUI 3270 may also include a switch (not shown) or a slide toggle 2016, which may be slid to one side 2018 to view a female estimate and the other side 2020 to view the male estimate.

Figure 24C:
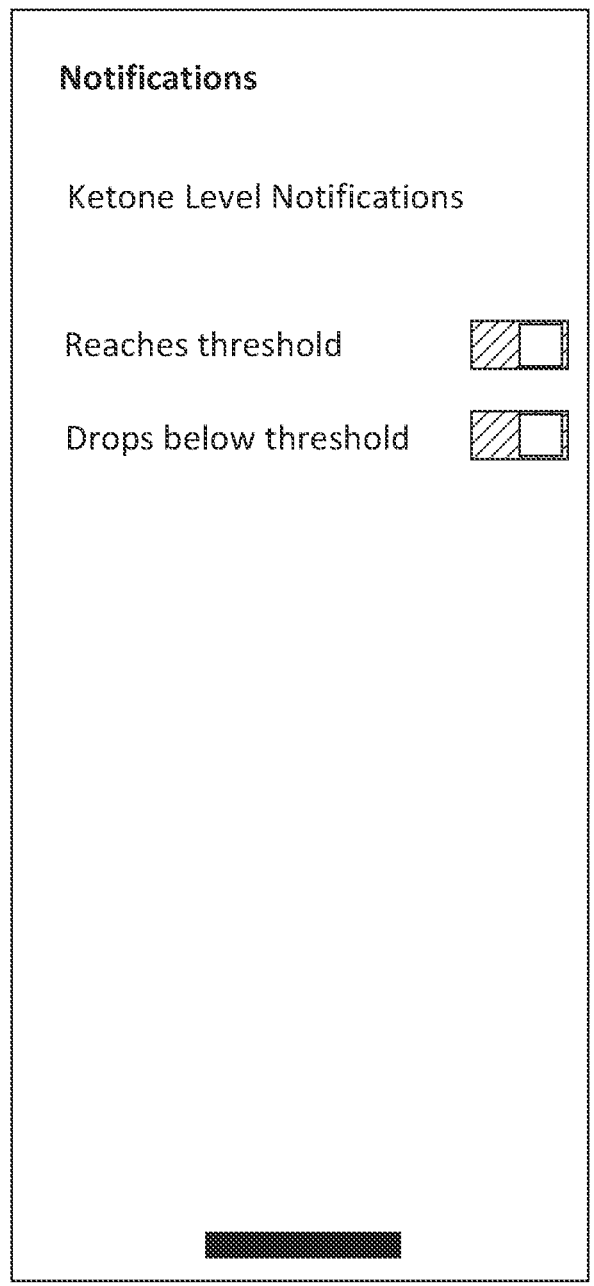

As seen in FIG. 24C, if the user selects or taps the notifications section 3254, the user may have the option to turn on or off available notifications. The notifications may include notifying the user when their ketone levels reach a threshold and notifying the user when their ketone levels drop below a threshold. The threshold may be a ketosis threshold. The threshold may be about 0.4 mmol/L, alternatively about 0.45 mmol/L, alternatively about 0.5 mmol/L, alternatively about 0.55 mmol/L, alternatively about 0.6 mmol/L.

In some embodiments, the system may determine if a ketone level is above a threshold ketone concentration. The system may then output a notification in response to a determination that the ketone level is above the threshold ketone concentration. In some embodiments, the ketone level may need to be above the threshold ketone concentration for a minimum period of time before the notification is outputted. The minimum period of time may be, e.g., at least about 2 minutes, alternatively at least about 5 minutes, alternatively at least about 10 minutes, alternatively at least about 15 minutes, alternatively at least about 30 minutes. The threshold ketone concentration may be predetermined, set by the application, or set by the user. The notification may include a tactile component, such as a vibration. The notification may include an audible component, such as a sound like a beep. The notification may be an alert that states that the user has reached a state of ketosis.

In some embodiments, the system may determine if a ketone level has dropped below the threshold ketone concentration. The system may then output a notification in response to a determination that the ketone level has dropped below the threshold ketone concentration. In some embodiments, the ketone level may need to be below the threshold ketone concentration for a minimum period of time before the notification is outputted. The minimum period of time may be, e.g., at least about 2 minutes, alternatively at least about 5 minutes, alternatively at least about 10 minutes, alternatively at least about 15 minutes, alternatively at least about 30 minutes. In some embodiments, the ketone level may need to have been above the ketone threshold concentration for a period of time and then drop below the ketone threshold concentration before a notification will be outputted regarding the ketone levels dropping below the ketone threshold concentration. The notification regarding the ketone levels dropping below the ketone threshold concentration may include a tactile component, such as a vibration. The notification regarding the ketone levels dropping below the ketone threshold concentration may include audible component, such as a sound like a beep. The notification regarding the ketone levels dropping below the ketone threshold concentration may be an alert that states that the user is no longer in a state of ketosis or that the user has dropped out of ketosis.

The notifications described in various embodiments herein may include toast alerts, banner alerts, lock screen alerts, slide-up notifications, or any other alert well known in mobile application design.

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible. The embodiments described herein are restated and expanded upon in the following paragraphs without explicit reference to the figures.

A software library for providing a uniform framework for various applications or third-party applications access to sensor data. The system further includes a sensor control module and a remote management module. The sensor control module includes logic for communicating with the sensors and receiving sensor data and to communicate that sensor data to the remote management module or various applications. The sensor control module may include a user interface that may display a banner containing numerous components. The content of the banner may differ depending on the host application. The system may further include a host application that incorporates the banner.

In many embodiments, an analyte monitoring system includes a receiving device, comprising: one or more processors; wireless communication circuitry configured to receive data indicative of an analyte level from a sensor control device comprising an analyte sensor, wherein at least a portion of the analyte sensor is configured to be in fluid contact with a bodily fluid of a subject; memory coupled with the one or more processors, the memory storing a host application and a software library, wherein the software library comprises a sensor control module configured to be executed by the one or more processors, the sensor control module comprising instructions that, when executed by the one or more processors, cause the one or more processors to: provide, by a sensor control module interface of the sensor control module, a first portion of the data indicative of the analyte level to the host application, determine a status of the analyte sensor, and display, by a user interface of the sensor control module, a second portion of the data indicative of the analyte level and the status of the analyte sensor.

In some embodiments, the first portion of the data indicative of the analyte level is displayed in a first section of the host application. In some embodiments, the second portion of the data indicative of the analyte level and the status of the analyte sensor are displayed in a second section of the host application. In some embodiments, the second section is a banner. In some embodiments, the second section is the only display of a real-time concentration of an analyte detected by the analyte sensor. In some embodiments, the second section is the only display of the status of the analyte sensor. In some embodiments, the second section is the primary display of the status of the analyte sensor. In some embodiments, the first section and the second section are displayed on the host application at a same time.

In some embodiments, the first portion of the data indicative of the analyte level and the second portion of the data indicative of the analyte level are overlapping.

In some embodiments, the first portion of the data indicative of the analyte level and the second portion of the data indicative of the analyte level are non-overlapping.

In some embodiments, the sensor control module interface of the sensor control module is configured to provide the first portion of the data indicative of the analyte level to the host application in response to a request from the host application.

In some embodiments, the first portion of the data indicative of the analyte level comprises analyte data received at a first interval. In some embodiments, the second portion of the data indicative of the analyte level comprises analyte data received at a second interval different from the first interval.

In some embodiments, the first portion of the data indicative of the analyte level comprises real time analyte data, and wherein the second portion of the data indicative of the analyte level comprises historical analyte data.

In some embodiments, the host application comprises the software library.

In some embodiments, the host application comprises instructions that, when executed by the one or more processors, cause the one or more processors to: determine at least one metric based on the first portion of the data indicative of the analyte level provided by the sensor control module, and display the at least one metric on the user interface.

In some embodiments, the first portion of the data indicative of the analyte level comprises a concentration of an analyte detected by the analyte sensor.

In some embodiments, the first portion of the data indicative of the analyte level is provided periodically.

In some embodiments, the first portion of the data indicative of the analyte level is provided every minute.

In some embodiments, the second portion of the data indicative of the analyte level comprises a real-time concentration of an analyte detected by the analyte sensor.

In some embodiments, the second portion of the data indicative of the analyte level comprises a trend arrow.

In some embodiments, the status of the analyte sensor comprises an icon and a description.

In some embodiments, the status of the analyte sensor comprises an indication of a remaining lifetime of the analyte sensor. In some embodiments, the indication of the remaining lifetime of the analyte sensor comprises a graphical indication, wherein the graphical indication comprises a progress indicator that is visually illustrates the remaining lifetime of the analyte sensor. In some embodiments, the graphical indication is a circle and the progress indicator is a colored portion of a perimeter of the circle, wherein a ratio of the colored portion of the perimeter of the circle and a total perimeter of the circle is proportional to a ratio of the remaining lifetime of the analyte sensor and a total lifetime of the analyte sensor. In some embodiments, the total lifetime of the analyte sensor is about 14 days. In some embodiments, the colored portion is a first color when the remaining lifetime of the sensor is greater than about 1 day, and wherein the colored portion is a second color when the remaining lifetime of the sensor is less than about 1 day.

In some embodiments, the indication of the remaining lifetime of the analyte sensor comprises a text description comprising a numerical value. In some embodiments, if the remaining lifetime of the sensor is greater than about 1 day, the numerical value of the text description comprises a number of days of the remaining lifetime of the sensor. In some embodiments, if the remaining lifetime of the sensor is less than about 1 day but greater than about 1 hour, the numerical value of the text description comprises a number of hours of the remaining lifetime of the sensor. In some embodiments, if the remaining lifetime of the sensor is less than about 1 hour, the numerical value of the text description comprises a number of minutes of the remaining lifetime of the sensor.

In some embodiments, the host application comprises instructions that, when executed by the one or more processors, further causes the one or more processors to: in response to selection of the second section, display, by a second user interface of the sensor control module, further details of the status of the analyte sensor. In some embodiments, the further details of the status of the analyte sensor comprises an amount of life remaining of the analyte sensor. In some embodiments, the further details of the status of the analyte sensor comprises a serial number of the analyte sensor. In some embodiments, the further details of the status of the analyte sensor comprises an identification number of the analyte sensor. In some embodiments, the further details of the status of the analyte sensor comprises an error message. In some embodiments, the error message comprises instructions to pair a new analyte sensor. In some embodiments, the error message comprises instructions to check an application of the analyte sensor to a user. In some embodiments, the error message comprises instructions to enable BLUETOOTH® on the receiving device. In some embodiments, the error message comprises a notification related to a temperature of the analyte sensor. In some embodiments, the temperature of the analyte sensor is too hot. In some embodiments, the temperature of the analyte sensor is too cold. In some embodiments, the further details of the status of the analyte sensor comprises a message to pair a new analyte sensor. In some embodiments, the further details of the status of the analyte sensor comprises an indication of an amount of time remaining until the analyte sensor is active. In some embodiments, the further details of the status of the analyte sensor comprises a message to start a new session.

In some embodiments, the host application comprises instructions that, when executed by the one or more processors, further cause the one or more processors to: in response to selection of the second section, display, by a third user interface of the sensor control module, details of pairing a new analyte sensor.

In some embodiments, the third user interface is only displayed after selection of the second section.

In many embodiments, a method includes the steps of: receiving, by a sensor control module, data indicative of an analyte level from a sensor control device comprising an analyte sensor, wherein at least a portion of the analyte sensor is configured to be in fluid contact with a bodily fluid of a subject; providing, by a sensor control module interface of the sensor control module, a first portion of the data indicative of the analyte level to a host application; determining a status of the analyte sensor; and displaying, by a user interface of the sensor control module, a second portion of the data indicative of the analyte level and the status of the analyte sensor to a user interface.

In some embodiments, the first portion of the data indicative of the analyte level is displayed in a first section of the host application. In some embodiments, the second portion of the data indicative of the analyte level is displayed in a second section of the host application. In some embodiments, the second section is a banner. In some embodiments, the second section is the only display of a real-time concentration of an analyte detected by the analyte sensor. In some embodiments, the second section is the only display of the status of the analyte sensor. In some embodiments, the second section is the primary display of the status of the analyte sensor.

In some embodiments, the first section and the second section are displayed on the host application at a same time.

In some embodiments, the first portion of the data indicative of the analyte level and the second portion of the data indicative of the analyte level are overlapping.

In some embodiments, the first portion of the data indicative of the analyte level and the second portion of the data indicative of the analyte level are non-overlapping.

In some embodiments, the sensor control module interface of the sensor control module provides the first portion of the data indicative of the analyte level to the host application in response to a request from the host application.

In some embodiments, the first portion of the data indicative of the analyte level comprises analyte data received at a first interval. In some embodiments, the second portion of the data indicative of the analyte level comprises analyte data received at a second interval different from the first interval.

In some embodiments, the first portion of the data indicative of the analyte level comprises real time analyte data, and wherein the second portion of the data indicative of the analyte level comprises historical analyte data.

In some embodiments, the host application comprises a software library. In some embodiments, the software library comprises the sensor control module.

In some embodiments, the method further comprises the steps of: determining at least one metric based on the first portion of the data indicative of the analyte level provided by the sensor control module; and displaying the at least one metric on the user interface.

In some embodiments, the first portion of the data indicative of the analyte level comprises a concentration of an analyte detected by the analyte sensor.

In some embodiments, the first portion of the data indicative of the analyte level is provided periodically.

In some embodiments, the first portion of the data indicative of the analyte level is provided every minute.

In some embodiments, the second portion of the data indicative of the analyte level comprises a real-time concentration of an analyte detected by the analyte sensor.

In some embodiments, the second portion of the data indicative of the analyte level comprises a trend arrow.

In some embodiments, the status of the analyte sensor comprises an icon and a description.

In some embodiments, the status of the analyte sensor comprises an indication of a remaining lifetime of the analyte sensor. In some embodiments, the indication of the remaining lifetime of the analyte sensor comprises a graphical indication, wherein the graphical indication comprises a progress indicator that is visually illustrates the remaining lifetime of the analyte sensor. In some embodiments, the graphical indication is a circle and the progress indicator is a colored portion of a perimeter of the circle, wherein a ratio of the colored portion of the perimeter of the circle and a total perimeter of the circle is proportional to a ratio of the remaining lifetime of the analyte sensor and a total lifetime of the analyte sensor. In some embodiments, the total lifetime of the analyte sensor is about 14 days. In some embodiments, the colored portion is a first color when the remaining lifetime of the sensor is greater than about 1 day, and wherein the colored portion is a second color when the remaining lifetime of the sensor is less than about 1 day.

In some embodiments, the indication of the remaining lifetime of the analyte sensor comprises a text description comprising a numerical value. In some embodiments, if the remaining lifetime of the sensor is greater than about 1 day, the numerical value of the text description comprises a number of days of the remaining lifetime of the sensor. In some embodiments, if the remaining lifetime of the sensor is less than about 1 day but greater than about 1 hour, the numerical value of the text description comprises a number of hours of the remaining lifetime of the sensor. In some embodiments, if the remaining lifetime of the sensor is less than about 1 hour, the numerical value of the text description comprises a number of minutes of the remaining lifetime of the sensor.

In some embodiments, the method further comprises the step of: in response to a selection of the second section by a user, displaying, by a second user interface of the sensor control module, further details of the status of the analyte sensor. In some embodiments, the further details of the status of the analyte sensor comprises an amount of life remaining of the analyte sensor. In some embodiments, the further details of the status of the analyte sensor comprises a serial number of the analyte sensor. In some embodiments, the further details of the status of the analyte sensor comprises an identification number of the analyte sensor. In some embodiments, the further details of the status of the analyte sensor comprises an error message. In some embodiments, the error message comprises instructions to pair a new analyte sensor. In some embodiments, the error message comprises instructions to check an application of the analyte sensor to a user. In some embodiments, the error message comprises instructions to enable BLUETOOTH® on the receiving device. In some embodiments, the error message comprises a notification related to a temperature of the analyte sensor. In some embodiments, the temperature of the analyte sensor is too hot. In some embodiments, the temperature of the analyte sensor is too cold. In some embodiments, the further details of the status of the analyte sensor comprises a message to pair a new analyte sensor. In some embodiments, the further details of the status of the analyte sensor comprises an indication of an amount of time remaining until the analyte sensor is active.

In some embodiments, the method further comprises the step of: in response to selection of the second section, displaying, by a third user interface of the sensor control module, details of pairing a new analyte sensor.

In some embodiments, the third user interface is only displayed after selection of the second section.

In many embodiments, an apparatus for displaying metrics relating to a subject includes: an input configured to receive measured analyte data; a display configured to visually present information; and one or more processors coupled with the input, the display, and a memory storing instructions that, when executed by the one or more processors, cause the apparatus to: determine a first recommended daily nutrient goal for a male and a second recommended daily nutrient goal for a female; determine a first recommended total daily calorie recommendation for a male and a second recommended daily nutrient goal for a female; in response to a selection of a male option, display a first graphical element indicative of the first recommended daily nutrient goal, wherein the first graphical element comprises a first graph having a first portion indicative of a daily carbohydrate recommendation, a second portion indicative of a daily protein recommendation, and a third portion indicative of a daily fat recommendation; display the first recommended total daily calorie recommendation; in response to a selection of a female option, display a second graphical element indicative of the second recommended daily nutrient goal, wherein the second graphical element comprises a second graph having a first portion indicative of a daily carbohydrate recommendation, a second portion indicative of a daily protein recommendation, and a third portion indicative of a daily fat recommendation; display the second recommended total daily calorie recommendation.

In some embodiments, each of the first graph and the second graph are a pie chart.

In some embodiments, the first graphical element further comprises a numerical value associated with each of the daily carbohydrate recommendation, the daily protein recommendation, and the daily fat recommendation. In some embodiments, the numerical value associated with each of the daily carbohydrate recommendation, the daily protein recommendation, and the daily fat recommendation is a percentage of the first recommended daily nutrient goal for each of the daily carbohydrate recommendation, the daily protein recommendation, and the daily fat recommendation. In some embodiments, the numerical value associated with each of the daily carbohydrate recommendation, the protein recommendation, and the daily fat recommendation is a gram amount for each of the daily carbohydrate recommendation, the daily protein recommendation, and the daily fat recommendation.

In some embodiments, the second graphical element further comprises a numerical value associated with each of the daily carbohydrate recommendation, the daily protein recommendation, and the daily fat recommendation. In some embodiments, the numerical value associated with each of the daily carbohydrate recommendation, the daily protein recommendation, and the daily fat recommendation is a percentage of the second recommended daily nutrient goal for each of the daily carbohydrate recommendation, the daily protein recommendation, and the daily fat recommendation. In some embodiments, the numerical value associated with each of the daily carbohydrate recommendation, the daily protein recommendation, and the daily fat recommendation is a gram amount for each of the daily carbohydrate recommendation, the protein recommendation, and the daily fat recommendation.

In some embodiments, the instructions further cause the apparatus to display a selectable option for a male and a selectable option for a female. In some embodiments, the selectable option for the male and the selectable option for the female is a slidable switch.

In some embodiments, the first and second recommended daily nutrient goals are determined based at least on a weight of the subject and an age of the subject.

In some embodiments, the first and second recommended daily nutrient goals are determined based at least on the received measured analyte data. In some embodiments, the received measured analyte data is ketone level data.

In many embodiments, an apparatus for displaying metrics relating to a subject includes: an input configured to receive measured ketone data; a display configured to visually present information; and one or more processors coupled with the input, the display, and a memory storing instructions that, when executed by the one or more processors, cause the apparatus to: display a graph comprising a ketone profile and a ketsosis threshold, wherein the ketone profile displays received measured ketone data for a period of time; display an average of a ketone level for the time period; and display a total amount of time in ketosis for the time period.

In some embodiments, the time period is one day.

In some embodiments, the graph further comprises a target threshold. In some embodiments, the instructions further cause the apparatus to display a total amount of time above the target threshold for the time period.

In some embodiments, the instructions further cause the apparatus to display a real time concentration of a ketone level.

In some embodiments, the instructions further cause the apparatus to display a trend arrow related to a concentration of a ketone level.

In some embodiments, the instructions further cause the apparatus to display a status of a biosensor, wherein the biosensor is configured to transmit the measured ketone data to the apparatus.

In some embodiments, the graph further comprises a shading in an area under the ketone profile. In some embodiments, the shading is a gradient, and wherein the shading is darker closer to a graph of the ketone profile.

In some embodiments, the graph further comprises at least one icon on the ketone profile corresponding to a logged entry. In some embodiments, the logged entry comprises a food and drink entry, a fasting entry, an exercise entry, a mood entry, an appetite entry, or an energy entry. In some embodiments, the at least one icon is a plurality of icons, and wherein the instructions further cause the apparatus to display a subset of the plurality of icons according to a filter.

In some embodiments, the graph further comprises at least one fasting icon on the ketone profile corresponding to a logged fasting entry having a fasting time duration having a start time and an end time, wherein a shading in an area under the ketone profile from the start time to the end time of the fasting time duration is distinguishable from a shading in an area under the ketone profile that that is before the start time and after the end time of the fasting time.

In some embodiments, the graph further comprises at least one exercise icon on the ketone profile corresponding to a logged exercise entry having an exercise time duration having a start time and an end time, wherein a shading in an area under the ketone profile from the start time to the end time of the exercise time duration is distinguishable from a shading in an area under the ketone profile that that is before the start time and after the end time of the exercise time.

In some embodiments, the instructions further cause the apparatus to display a pill in response to a plurality of logged entries with corresponding to logged times occurring during a small, predetermined time period. In some embodiments, the small, predetermined time period is about an hour. In some embodiments, the pill comprises a display of a number of the plurality of logged entries corresponding to the logged time during the small, predetermined time period. In some embodiments, the instructions further cause the apparatus to display a tooltip in response to selection of or pressure applied to the pill. In some embodiments, the tooltip comprises a display listing the logged entries. In some embodiments, each of the logged entries in the listing comprise an icon, a logging time, and a brief description.

In some embodiments, the instructions further cause the apparatus to display a flag in response to pressure applied to the display for a minimum period of time. In some embodiments, the flag comprises a display of an indication of a concentration of ketone at a first time, wherein the first time corresponds to a time on the graph at or near where the pressure was applied to the display. In some embodiments, if the concentration is below a low threshold concentration, the indication of the concentration of ketone at the first time is a statement that the concentration is below the low threshold. In some embodiments, if the concentration is below a low threshold concentration, the indication of the concentration of ketone does not include a numeric value for the concentration of ketone. In some embodiments, if the concentration is above a high threshold concentration, the indication of the concentration of ketone at the first time is a statement that the concentration is above the high threshold. In some embodiments, if the concentration is above the high threshold concentration, the indication of the concentration of ketone does not include a numeric value for the concentration of ketone. In some embodiments, if the concentration is between a low threshold and a high threshold, the indication of the concentration of ketone includes a numeric value for the concentration of ketone.

In some embodiments, the instructions further cause the apparatus to display a plurality of additional flags in response to the pressure being moved along the graph. In some embodiments, each of the plurality of additional flags comprises a display of an indication of a concentration of ketone at a plurality of different times, wherein each of the plurality of different times corresponds to a time on the graph at or near where pressure is being applied to the display.

In some embodiments, the instructions further cause the apparatus to stop displaying the flag in response to a termination of the pressure applied to the display for the minimum period of time.

In many embodiments, an apparatus for displaying metrics relating to a subject includes: an input configured to receive measured ketone data; a display configured to visually present information; and one or more processors coupled with the input, the display, and a memory storing instructions that, when executed by the one or more processors, cause the apparatus to: display a graph comprising a ketone profile and at least one fasting icon on a first graphic user interface, wherein the ketone profile displays received measured ketone data for a time period; and display a second graphic user interface comprising an elapsed fasting time, a goal time, and a graphical element indicative of an amount of time the subject has been fasting.

In some embodiments, the second graphic user interface is configured to be displayed in response to a selection of the at least one fasting icon in the graph.

In some embodiments, the second graphic user interface is a pop-up screen.

In some embodiments, the second graphic user interface further comprises a start time and an end time of the goal time.

In some embodiments, the graph of the first graphic user interface further comprises a target threshold and a ketsosis threshold.

In some embodiments, the first graphic user interface further comprises a display of an average of a ketone level for the time period, a display of a total amount of time in ketosis for the time period, and a display of a total amount of time above the target threshold for the time period.

In many embodiments, an apparatus for displaying metrics relating to a subject includes: an input configured to receive measured ketone data; a display configured to visually present information; and one or more processors coupled with the input, the display, and a memory storing instructions that, when executed by the one or more processors, cause the apparatus to: display, on a graphic user interface, a graph comprising a ketone profile and at least one exercise icon corresponding to a logged exercise entry having an exercise time duration having a start time and an end time, wherein the ketone profile displays received measured ketone data for a time period, and wherein a shading in an area under the ketone profile from the start time to the end time of the exercise time duration is distinguishable from a shading in an area under the ketone profile that that is before the start time and after the end time of the exercise time.

In some embodiments, the logged exercise entry comprises a description of the exercise and an intensity of the exercise.

In some embodiments, the instructions further cause the one or more processors to display a first vertical line at the start time and a second vertical line at the end time, wherein the first vertical line and the second vertical line are configured to be moved to change the start time and the end time, respectively.

In many embodiments, a method of logging a fasting period includes the steps of: selecting a time period of a fasting period from a plurality of predetermined fasting periods; and entering a start time of the fasting period, wherein an end time of the fasting period is automatically determined based on the start time of the fasting period and the selected predetermined fasting period.

In some embodiments, the plurality of predetermined fasting periods comprise at least one of none, 13 hours, 16 hours, 18 hours, 20 hours, and 36 hours.

In some embodiments, the start time of the fasting period is selected on a wheel.

In some embodiments, the start time of the fasting period is entered in a text field.

In many embodiments, a method of logging an exercise period includes the steps of: setting a start time and a start date of the exercise period; setting a duration of the exercise period; entering a description of an exercise performed during the exercise period; and entering an intensity of the exercise performed during the exercise period.

In some embodiments, the intensity of the exercise performed during the exercise period is entered by adjusting a slide bar to indicate an intensity from a range of low to high.

In some embodiments, entering the description of the exercise performed comprises typing a description of the exercise into a text field.

In some embodiments, entering the description of the exercise performed comprises selecting an exercise from a suggested list of exercises.

In some embodiments, the suggested list of exercises comprises a list of past exercises entered by a user.

In some embodiments, the suggested list of exercises comprises a list of five most recent exercises entered by a user.

In many embodiments, a method of logging a mood includes the steps of: setting a time and a date of a mood entry; selecting a mood from a plurality of mood options; and entering a description of a feeling associated with the time and the date of the mood entry.

In some embodiments, the plurality of mood options comprises a plurality of emojis depicting different expressions.

In some embodiments, entering the description of the feeling comprises typing a description of the feeling into a text field.

In some embodiments, entering the description of the feeling comprises selecting a feeling from a suggested list of feelings. In some embodiments, the suggested list of feelings comprises a list of past feelings entered by a user. In some embodiments, the suggested list of feelings comprises a list of five most recent feelings entered by a user.

In many embodiments, a method of logging an energy level comprises the steps of: setting a time and date of an energy level entry; entering an energy level; and entering a description of a feeling associated with the time and date of the energy level entry.

In some embodiments, the energy level is entered by adjusting a slide bar to indicate an energy level from a range of low to medium to high.

In some embodiments, entering the description of the feeling comprises typing a description of the feeling into a text field.

In some embodiments, entering the description of the feeling comprises selecting a feeling from a suggested list of feelings. In some embodiments, the suggested list of feelings comprises a list of past feelings entered by a user. In some embodiments, the suggested list of feelings comprises a list of five most recent feelings entered by a user.

In many embodiments, a method of logging an appetite level includes the steps of: setting a time and date of an appetite level entry; entering an appetite level; and entering a description of a feeling associated with the time and date of the appetite level entry.

In some embodiments, the appetite level is entered by adjusting a slide bar to indicate a level from a range of low to medium to high.

In some embodiments, entering the description of the feeling comprises typing a description of the feeling into a text field.

In some embodiments, entering the description of the feeling comprises selecting a feeling from a suggested list of feelings. In some embodiments, the suggested list of feelings comprises a list of past feelings entered by a user. In some embodiments, the suggested list of feelings comprises a list of five most recent feelings entered by a user.

In many embodiments, an apparatus for analyzing metrics relating to a subject includes: an input configured to receive measured ketone data; a display configured to visually present information; and one or more processors coupled with the input, the display, and a memory storing instructions that, when executed by the one or more processors, cause the apparatus to: determine if a ketone level is above a threshold ketone concentration; and output a notification in response to a determination that the ketone level is above the threshold ketone concentration.

In some embodiments, the threshold ketone concentration is predetermined.

In some embodiments, the threshold ketone concentration is set by the subject.

In some embodiments, the threshold ketone concentration is about 0.5 mmol/L.

In some embodiments, the notification in response to the determination that the ketone level is above the threshold ketone concentration comprises a tactile component. In some embodiments, the tactile component is a vibration.

In some embodiments, the notification in response to the determination that the ketone level is above the threshold ketone concentration comprises a sound.

In some embodiments, the notification in response to the determination that the ketone level is above the threshold ketone concentration comprises a message stating that a user has reached a state of ketosis.

In some embodiments, the instructions further cause the apparatus to: determine if a ketone level drops below the threshold ketone concentration after a determination that the ketone level was above the threshold ketone concentration; and output a notification in response to a determination that the ketone level dropped below the threshold ketone concentration. In some embodiments, wherein the notification in response to the determination that the ketone level dropped below the threshold ketone concentration comprises a tactile component. In some embodiments, the tactile component is a vibration. In some embodiments, the notification in response to the determination that the ketone level dropped below the threshold ketone concentration comprises a sound. In some embodiments, the notification in response to the determination that the ketone level dropped below the threshold ketone concentration comprises a message stating that a user has dropped out of ketosis.

CONCLUSION

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Thus, the foregoing description of specific embodiments of the disclosed subject matter has been presented for purposes of illustration and description. It is explicitly acknowledged that express recitation of every possible combination and substitution is overly burdensome, especially given that the permissibility of each and every such combination and substitution will be readily recognized by those of ordinary skill in the art.

While the embodiments are susceptible to various modifications and alternative forms, specific examples thereof have been shown in the drawings and are herein described in detail. It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents. Furthermore, any features, functions, steps, or elements of the embodiments may be recited in or added to the claims, as well as negative limitations that define the inventive scope of the claims by features, functions, steps, or elements that are not within that scope.

Clauses

Exemplary embodiments are set out in the following numbered clauses.

Clause 1. An analyte monitoring system, comprising:
a receiving device, comprising:
one or more processors;
wireless communication circuitry configured to receive data indicative of an analyte level from a sensor control device comprising an analyte sensor, wherein at least a portion of the analyte sensor is configured to be in fluid contact with a bodily fluid of a subject;
memory coupled with the one or more processors, the memory storing a host application and a software library, wherein the software library comprises a sensor control module configured to be executed by the one or more processors, the sensor control module comprising instructions that, when executed by the one or more processors, cause the one or more processors to:
provide, by a sensor control module interface of the sensor control module, a first portion of the data indicative of the analyte level to the host application, determine a status of the analyte sensor, and
display, by a user interface of the sensor control module, a second portion of the data indicative of the analyte level and the status of the analyte sensor.

Clause 2. The system of clause 1, wherein the first portion of the data indicative of the analyte level is displayed in a first section of the host application.

Clause 3. The system of clause 2, wherein the second portion of the data indicative of the analyte level and the status of the analyte sensor are displayed in a second section of the host application.

Clause 4. The system of clause 3, wherein the second section is a banner.

Clause 5. The system of clause 3, wherein the second section is the only display of a real-time concentration of an analyte detected by the analyte sensor.

Clause 6. The system of clause 3, wherein the second section is the only display of the status of the analyte sensor.

Clause 7. The system of clause 3, wherein the second section is the primary display of the status of the analyte sensor.

Clause 8. The system of clause 3, wherein the first section and the second section are displayed on the host application at a same time.

Clause 9. The system of clause 1, wherein the first portion of the data indicative of the analyte level and the second portion of the data indicative of the analyte level are overlapping.

Clause 10. The system of clause 1, wherein the first portion of the data indicative of the analyte level and the second portion of the data indicative of the analyte level are non-overlapping.

Clause 11. The system of clause 1, wherein the sensor control module interface of the sensor control module is configured to provide the first portion of the data indicative of the analyte level to the host application in response to a request from the host application.

Clause 12. The system of clause 1, wherein the first portion of the data indicative of the analyte level comprises analyte data received at a first interval.

Clause 13. The system of clause 12, wherein the second portion of the data indicative of the analyte level comprises analyte data received at a second interval different from the first interval.

Clause 14. The system of clause 1, wherein the first portion of the data indicative of the analyte level comprises real time analyte data, and wherein the second portion of the data indicative of the analyte level comprises historical analyte data.

Clause 15. The system of clause 1, wherein the host application comprises the software library.

Clause 16. The system of clause 1, wherein the host application comprises instructions that, when executed by the one or more processors, cause the one or more processors to:
determine at least one metric based on the first portion of the data indicative of the analyte level provided by the sensor control module, and
display the at least one metric on the user interface.

Clause 17. The system of clause 1, wherein the first portion of the data indicative of the analyte level comprises a concentration of an analyte detected by the analyte sensor.

Clause 18. The system of clause 1, wherein the first portion of the data indicative of the analyte level is provided periodically.

Clause 19. The system of clause 1, wherein the first portion of the data indicative of the analyte level is provided every minute.

Clause 20. The system of clause 1, wherein the second portion of the data indicative of the analyte level comprises a real-time concentration of an analyte detected by the analyte sensor.

Clause 21. The system of clause 1, wherein the second portion of the data indicative of the analyte level comprises a trend arrow.

Clause 22. The system of clause 1, wherein the status of the analyte sensor comprises an icon and a description.

Clause 23. The system of clause 1, wherein the status of the analyte sensor comprises an indication of a remaining lifetime of the analyte sensor.

Clause 24. The system of clause 23, wherein the indication of the remaining lifetime of the analyte sensor comprises a graphical indication, wherein the graphical indication comprises a progress indicator that is visually illustrates the remaining lifetime of the analyte sensor.

Clause 25. The system of clause 24, wherein the graphical indication is a circle and the progress indicator is a colored portion of a perimeter of the circle, wherein a ratio of the colored portion of the perimeter of the circle and a total perimeter of the circle is proportional to a ratio of the remaining lifetime of the analyte sensor and a total lifetime of the analyte sensor.

Clause 26. The system of clause 25, wherein the total lifetime of the analyte sensor is about 14 days.

Clause 27. The system of clause 25, wherein the colored portion is a first color when the remaining lifetime of the sensor is greater than about 1 day, and wherein the colored portion is a second color when the remaining lifetime of the sensor is less than about 1 day.

Clause 28. The system of clause 23, wherein the indication of the remaining lifetime of the analyte sensor comprises a text description comprising a numerical value.

Clause 29. The system of clause 28, wherein if the remaining lifetime of the sensor is greater than about 1 day, the numerical value of the text description comprises a number of days of the remaining lifetime of the sensor.

Clause 30. The system of clause 28, wherein if the remaining lifetime of the sensor is less than about 1 day but greater than about 1 hour, the numerical value of the text description comprises a number of hours of the remaining lifetime of the sensor.

Clause 31. The system of clause 28, wherein if the remaining lifetime of the sensor is less than about 1 hour, the numerical value of the text description comprises a number of minutes of the remaining lifetime of the sensor.

Clause 32. The system of clause 3, wherein the host application comprises instructions that, when executed by the one or more processors, further causes the one or more processors to:
in response to selection of the second section, display, by a second user interface of the sensor control module, further details of the status of the analyte sensor.

Clause 33. The system of clause 32, wherein the further details of the status of the analyte sensor comprises an amount of life remaining of the analyte sensor.

Clause 34. The system of clause 32, wherein the further details of the status of the analyte sensor comprises a serial number of the analyte sensor.

Clause 35. The system of clause 32, wherein the further details of the status of the analyte sensor comprises an identification number of the analyte sensor.

Clause 36. The system of clause 32, wherein the further details of the status of the analyte sensor comprises an error message.

Clause 37. The system of clause 36, wherein the error message comprises instructions to pair a new analyte sensor.

Clause 38. The system of clause 36, wherein the error message comprises instructions to check an application of the analyte sensor to a user.

Clause 39. The system of clause 36, wherein the error message comprises instructions to enable BLUETOOTH® on the receiving device.

Clause 40. The system of clause 36, wherein the error message comprises a notification related to a temperature of the analyte sensor.

Clause 41. The system of clause 40, wherein the temperature of the analyte sensor is too hot.

Clause 42. The system of clause 40, wherein the temperature of the analyte sensor is too cold.

Clause 43. The system of clause 32, wherein the further details of the status of the analyte sensor comprises a message to pair a new analyte sensor.

Clause 44. The system of clause 32, wherein the further details of the status of the analyte sensor comprises an indication of an amount of time remaining until the analyte sensor is active.

Clause 45. The system of clause 32, wherein the further details of the status of the analyte sensor comprises a message to start a new session.

Clause 46. The system of clause 3, wherein the host application comprises instructions that, when executed by the one or more processors, further cause the one or more processors to:

in response to selection of the second section, display, by a third user interface of the sensor control module, details of pairing a new analyte sensor.

Clause 47. The system of clause 46, wherein the third user interface is only displayed after selection of the second section.

Clause 48. A method comprising:

receiving, by a sensor control module, data indicative of an analyte level from a sensor control device comprising an analyte sensor, wherein at least a portion of the analyte sensor is configured to be in fluid contact with a bodily fluid of a subject;

providing, by a sensor control module interface of the sensor control module, a first portion of the data indicative of the analyte level to a host application;

determining a status of the analyte sensor; and displaying, by a user interface of the sensor control module, a second portion of the data indicative of the analyte level and the status of the analyte sensor to a user interface.

Clause 49. The method of clause 48, wherein the first portion of the data indicative of the analyte level is displayed in a first section of the host application.

Clause 50. The method of clause 49, wherein the second portion of the data indicative of the analyte level is displayed in a second section of the host application.

Clause 51. The method of clause 50, wherein the second section is a banner.

Clause 52. The method of clause 50, wherein the second section is the only display of a real-time concentration of an analyte detected by the analyte sensor.

Clause 53. The method of clause 50, wherein the second section is the only display of the status of the analyte sensor.

Clause 54. The method of clause 50, wherein the second section is the primary display of the status of the analyte sensor.

Clause 55. The method of clause 50, wherein the first section and the second section are displayed on the host application at a same time.

Clause 56. The method of clause 48, wherein the first portion of the data indicative of the analyte level and the second portion of the data indicative of the analyte level are overlapping.

Clause 57. The method of clause 48, wherein the first portion of the data indicative of the analyte level and the second portion of the data indicative of the analyte level are non-overlapping.

Clause 58. The method of clause 48, wherein the sensor control module interface of the sensor control module provides the first portion of the data indicative of the analyte level to the host application in response to a request from the host application.

Clause 59. The method of clause 48, wherein the first portion of the data indicative of the analyte level comprises analyte data received at a first interval.

Clause 60. The method of clause 59, wherein the second portion of the data indicative of the analyte level comprises analyte data received at a second interval different from the first interval.

Clause 61. The method of clause 48, wherein the first portion of the data indicative of the analyte level comprises real time analyte data, and wherein the second portion of the data indicative of the analyte level comprises historical analyte data.

Clause 62. The method of clause 48, wherein the host application comprises a software library.

Clause 63. The method of clause 62, wherein the software library comprises the sensor control module.

Clause 64. The method of clause 48, further comprising the steps of:

determining at least one metric based on the first portion of the data indicative of the analyte level provided by the sensor control module; and displaying the at least one metric on the user interface.

Clause 65. The method of clause 48, wherein the first portion of the data indicative of the analyte level comprises a concentration of an analyte detected by the analyte sensor.

Clause 66. The method of clause 48, wherein the first portion of the data indicative of the analyte level is provided periodically.

Clause 67. The method of clause 48, wherein the first portion of the data indicative of the analyte level is provided every minute.

Clause 68. The method of clause 48, wherein the second portion of the data indicative of the analyte level comprises a real-time concentration of an analyte detected by the analyte sensor.

Clause 69. The method of clause 48, wherein the second portion of the data indicative of the analyte level comprises a trend arrow.

Clause 70. The method of clause 48, wherein the status of the analyte sensor comprises an icon and a description.

Clause 71. The method of clause 48, wherein the status of the analyte sensor comprises an indication of a remaining lifetime of the analyte sensor.

Clause 72. The method of clause 71, wherein the indication of the remaining lifetime of the analyte sensor comprises a graphical indication, wherein the graphical indication comprises a progress indicator that is visually illustrates the remaining lifetime of the analyte sensor.

Clause 73. The method of clause 72, wherein the graphical indication is a circle and the progress indicator is a colored portion of a perimeter of the circle, wherein a ratio of the colored portion of the perimeter of the circle and a total perimeter of the circle is proportional to a ratio of the remaining lifetime of the analyte sensor and a total lifetime of the analyte sensor.

Clause 74. The method of clause 73, wherein the total lifetime of the analyte sensor is about 14 days.

Clause 75. The method of clause 73, wherein the colored portion is a first color when the remaining lifetime of the sensor is greater than about 1 day, and wherein the colored portion is a second color when the remaining lifetime of the sensor is less than about 1 day.

Clause 76. The method of clause 71, wherein the indication of the remaining lifetime of the analyte sensor comprises a text description comprising a numerical value.

Clause 77. The method of clause 76, wherein if the remaining lifetime of the sensor is greater than about 1 day, the numerical value of the text description comprises a number of days of the remaining lifetime of the sensor.

Clause 78. The method of clause 76, wherein if the remaining lifetime of the sensor is less than about 1 day but greater than about 1 hour, the numerical value of the text description comprises a number of hours of the remaining lifetime of the sensor.

Clause 79. The method of clause 76, wherein if the remaining lifetime of the sensor is less than about 1 hour, the numerical value of the text description comprises a number of minutes of the remaining lifetime of the sensor.

Clause 80. The method of clause 50, further comprising the step of:
in response to a selection of the second section by a user, displaying, by a second user interface of the sensor control module, further details of the status of the analyte sensor.

Clause 81. The method of clause 80, wherein the further details of the status of the analyte sensor comprises an amount of life remaining of the analyte sensor.

Clause 82. The method of clause 80, wherein the further details of the status of the analyte sensor comprises a serial number of the analyte sensor.

Clause 83. The method of clause 80, wherein the further details of the status of the analyte sensor comprises an identification number of the analyte sensor.

Clause 84. The method of clause 80, wherein the further details of the status of the analyte sensor comprises an error message.

Clause 85. The method of clause 84, wherein the error message comprises instructions to pair a new analyte sensor.

Clause 86. The method of clause 84, wherein the error message comprises instructions to check an application of the analyte sensor to a user.

Clause 87. The method of clause 84, wherein the error message comprises instructions to enable BLUETOOTH® on the receiving device.

Clause 88. The method of clause 84, wherein the error message comprises a notification related to a temperature of the analyte sensor.

Clause 89. The method of clause 88, wherein the temperature of the analyte sensor is too hot.

Clause 90. The method of clause 88, wherein the temperature of the analyte sensor is too cold.

Clause 91. The method of clause 84, wherein the further details of the status of the analyte sensor comprises a message to pair a new analyte sensor.

Clause 92. The method of clause 84, wherein the further details of the status of the analyte sensor comprises an indication of an amount of time remaining until the analyte sensor is active.

Clause 93. The method of clause 80, further comprising the step of:
in response to selection of the second section, displaying, by a third user interface of the sensor control module, details of pairing a new analyte sensor.

Clause 94. The method of clause 93, wherein the third user interface is only displayed after selection of the second section.

Clause 95. An apparatus for displaying metrics relating to a subject, the apparatus comprising:
an input configured to receive measured analyte data;
a display configured to visually present information; and
one or more processors coupled with the input, the display, and a memory storing instructions that, when executed by the one or more processors, cause the apparatus to:
determine a first recommended daily nutrient goal for a male and a second recommended daily nutrient goal for a female;
determine a first recommended total daily calorie recommendation for a male and a second recommended daily nutrient goal for a female;
in response to a selection of a male option,
display a first graphical element indicative of the first recommended daily nutrient goal, wherein the first graphical element comprises a first graph having a first portion indicative of a daily carbohydrate recommendation, a second portion indicative of a daily protein recommendation, and a third portion indicative of a daily fat recommendation;
display the first recommended total daily calorie recommendation;
in response to a selection of a female option,
display a second graphical element indicative of the second recommended daily nutrient goal, wherein the second graphical element comprises a second graph having a first portion indicative of a daily carbohydrate recommendation, a second portion indicative of a daily protein recommendation, and a third portion indicative of a daily fat recommendation;
display the second recommended total daily calorie recommendation.

Clause 96. The apparatus of clause 95, wherein each of the first graph and the second graph are a pie chart.

Clause 97. The apparatus of clause 95, wherein the first graphical element further comprises a numerical value associated with each of the daily carbohydrate recommendation, the daily protein recommendation, and the daily fat recommendation.

Clause 98. The apparatus of clause 97, where the numerical value associated with each of the daily carbohydrate recommendation, the daily protein recommendation, and the daily fat recommendation is a percentage of the first recommended daily nutrient goal for each of the daily carbohydrate recommendation, the daily protein recommendation, and the daily fat recommendation.

Clause 99. The apparatus of clause 97, where the numerical value associated with each of the daily carbohydrate recommendation, the protein recommendation, and the daily fat recommendation is a gram amount for each of the daily carbohydrate recommendation, the daily protein recommendation, and the daily fat recommendation.

Clause 100. The apparatus of clause 95, wherein the second graphical element further comprises a numerical value associated with each of the daily carbohydrate recommendation, the daily protein recommendation, and the daily fat recommendation.

Clause 101. The apparatus of clause 100, where the numerical value associated with each of the daily carbohydrate recommendation, the daily protein recommendation, and the daily fat recommendation is a percentage of the second recommended daily nutrient goal for each of the daily carbohydrate recommendation, the daily protein recommendation, and the daily fat recommendation.

Clause 102. The apparatus of clause 100, where the numerical value associated with each of the daily carbohydrate recommendation, the daily protein recommendation, and the daily fat recommendation is a gram amount for each of the daily carbohydrate recommendation, the protein recommendation, and the daily fat recommendation.

Clause 103. The apparatus of clause 95, wherein the instructions further cause the apparatus to display a selectable option for a male and a selectable option for a female.

Clause 104. The apparatus of clause 103, wherein the selectable option for the male and the selectable option for the female is a slidable switch.

Clause 105. The apparatus of clause 95, wherein the first and second recommended daily nutrient goals are determined based at least on a weight of the subject and an age of the subject.

Clause 106. The apparatus of clause 95, wherein the first and second recommended daily nutrient goals are determined based at least on the received measured analyte data.

Clause 107. The apparatus of clause 106, wherein the received measured analyte data is ketone level data.

Clause 108. An apparatus for displaying metrics relating to a subject, the apparatus comprising:
an input configured to receive measured ketone data;
a display configured to visually present information; and
one or more processors coupled with the input, the display, and a memory storing instructions that, when executed by the one or more processors, cause the apparatus to:
display a graph comprising a ketone profile and a ketsosis threshold, wherein the ketone profile displays received measured ketone data for a time period;
display an average of a ketone level for the time period; and
display a total amount of time in ketosis for the time period.

Clause 109. The apparatus of clause 108, wherein the time period is one day.

Clause 110. The apparatus of clause 108, wherein the graph further comprises a target threshold.

Clause 111. The apparatus of clause 110, wherein the instructions further cause the apparatus to display a total amount of time above the target threshold for the time period.

Clause 112. The apparatus of clause 108, wherein the instructions further cause the apparatus to display a real time concentration of a ketone level.

Clause 113. The apparatus of clause 108, wherein the instructions further cause the apparatus to display a trend arrow related to a concentration of a ketone level.

Clause 114. The apparatus of clause 108, wherein the instructions further cause the apparatus to display a status of a biosensor, wherein the biosensor is configured to transmit the measured ketone data to the apparatus.

Clause 115. The apparatus of clause 108, wherein the graph further comprises a shading in an area under the ketone profile.

Clause 116. The apparatus of clause 115, wherein the shading is a gradient, and wherein the shading is darker closer to a graph of the ketone profile.

Clause 117. The apparatus of clause 108, wherein the graph further comprises at least one icon on the ketone profile corresponding to a logged entry.

Clause 118. The apparatus of clause 117, wherein the logged entry comprises a food and drink entry, a fasting entry, an exercise entry, a mood entry, an appetite entry, or an energy entry.

Clause 119. The apparatus of clause 117, wherein the at least one icon is a plurality of icons, and wherein the instructions further cause the apparatus to display a subset of the plurality of icons according to a filter.

Clause 120. The apparatus of clause 108, wherein the graph further comprises at least one fasting icon on the ketone profile corresponding to a logged fasting entry having a fasting time duration having a start time and an end time, wherein a shading in an area under the ketone profile from the start time to the end time of the fasting time duration is distinguishable from a shading in an area under the ketone profile that that is before the start time and after the end time of the fasting time.

Clause 121. The apparatus of clause 108, wherein the graph further comprises at least one exercise icon on the ketone profile corresponding to a logged exercise entry having an exercise time duration having a start time and an end time, wherein a shading in an area under the ketone profile from the start time to the end time of the exercise time duration is distinguishable from a shading in an area under the ketone profile that that is before the start time and after the end time of the exercise time.

Clause 122. The apparatus of clause 108, wherein the instructions further cause the apparatus to display a pill in response to a plurality of logged entries with corresponding to logged times occurring during a small, predetermined time period.

Clause 123. The apparatus of clause 122, wherein the small, predetermined time period is about an hour.

Clause 124. The apparatus of clause 122, wherein the pill comprises a display of a number of the plurality of logged entries corresponding to the logged time during the small, predetermined time period.

Clause 125. The apparatus of clause 122, wherein the instructions further cause the apparatus to display a tooltip in response to selection of or pressure applied to the pill.

Clause 126. The apparatus of clause 125, wherein the tooltip comprises a display listing the logged entries.

Clause 127. The apparatus of clause 126, wherein the each of the logged entries in the listing comprise an icon, a logging time, and a brief description.

Clause 128. The apparatus of clause 108, wherein the instructions further cause the apparatus to display a flag in response to pressure applied to the display for a minimum period of time.

Clause 129. The apparatus of clause 128, wherein the flag comprises a display of an indication of a concentration of ketone at a first time, wherein the first time corresponds to a time on the graph at or near where the pressure was applied to the display.

Clause 130. The apparatus of clause 129, wherein if the concentration is below a low threshold concentration, the indication of the concentration of ketone at the first time is a statement that the concentration is below the low threshold.

Clause 131. The apparatus of clause 129, wherein if the concentration is below a low threshold concentration, the indication of the concentration of ketone does not include a numeric value for the concentration of ketone.

Clause 132. The apparatus of clause 129, wherein if the concentration is above a high threshold concentration, the indication of the concentration of ketone at the first time is a statement that the concentration is above the high threshold.

Clause 133. The apparatus of clause 129, wherein if the concentration is above the high threshold concentration, the indication of the concentration of ketone does not include a numeric value for the concentration of ketone.

Clause 134. The apparatus of clause 129, wherein if the concentration is between a low threshold and a high threshold, the indication of the concentration of ketone includes a numeric value for the concentration of ketone.

Clause 135. The apparatus of clause 128, wherein the instructions further cause the apparatus to display a plurality of additional flags in response to the pressure being moved along the graph.

Clause 136. The apparatus of clause 135, wherein the each of the plurality of additional flags comprises a display of an indication of a concentration of ketone at a plurality of different times, wherein each of the plurality of different times corresponds to a time on the graph at or near where pressure is being applied to the display.

Clause 137. The apparatus of clause 128, wherein the instructions further cause the apparatus to stop displaying the flag in response to a termination of the pressure applied to the display for the minimum period of time.

Clause 138. An apparatus for displaying metrics relating to a subject, the apparatus comprising:
  an input configured to receive measured ketone data;
  a display configured to visually present information; and
  one or more processors coupled with the input, the display, and a memory storing instructions that, when executed by the one or more processors, cause the apparatus to:
    display a graph comprising a ketone profile and at least one fasting icon on a first graphic user interface, wherein the ketone profile displays received measured ketone data for a time period; and
    display a second graphic user interface comprising an elapsed fasting time, a goal time, and a graphical element indicative of an amount of time the subject has been fasting.

Clause 139. The apparatus of clause 138, wherein the second graphic user interface is configured to be displayed in response to a selection of the at least one fasting icon in the graph.

Clause 140. The apparatus of clause 138, wherein the second graphic user interface is a pop-up screen.

Clause 141. The apparatus of clause 138, wherein the second graphic user interface further comprises a start time and an end time of the goal time.

Clause 142. The apparatus of clause 138, wherein the graph of the first graphic user interface further comprises a target threshold and a ketsosis threshold.

Clause 143. The apparatus of clause 138, wherein the first graphic user interface further comprises a display of an average of a ketone level for the time period, a display of a total amount of time in ketosis for the time period, and a display of a total amount of time above the target threshold for the time period.

Clause 144. An apparatus for displaying metrics relating to a subject, the apparatus comprising:
  an input configured to receive measured ketone data;
  a display configured to visually present information; and
  one or more processors coupled with the input, the display, and a memory storing instructions that, when executed by the one or more processors, cause the apparatus to:
    display, on a graphic user interface, a graph comprising a ketone profile and at least one exercise icon corresponding to a logged exercise entry having an exercise time duration having a start time and an end time, wherein the ketone profile displays received measured ketone data for a time period, and wherein a shading in an area under the ketone profile from the start time to the end time of the exercise time duration is distinguishable from a shading in an area under the ketone profile that that is before the start time and after the end time of the exercise time.

Clause 145. The apparatus of clause 144, wherein the logged exercise entry comprises a description of the exercise and an intensity of the exercise.

Clause 146. The apparatus of clause 144, wherein the instructions further cause the one or more processors to display a first vertical line at the start time and a second vertical line at the end time, wherein the first vertical line and the second vertical line are configured to be moved to change the start time and the end time, respectively.

Clause 147. A method of logging a fasting period, comprising:
  selecting a time period of a fasting period from a plurality of predetermined fasting periods; and
  entering a start time of the fasting period, wherein an end time of the fasting period is automatically determined based on the start time of the fasting period and the selected predetermined fasting period.

Clause 148. The method of clause 147, wherein the plurality of predetermined fasting periods comprise at least one of none, 13 hours, 16 hours, 18 hours, 20 hours, and 36 hours.

Clause 149. The method of clause 147, wherein the start time of the fasting period is selected on a wheel.

Clause 150. The method of clause 147, wherein the start time of the fasting period is entered in a text field.

Clause 151. A method of logging an exercise period, comprising the steps of:
  setting a start time and a start date of the exercise period;
  setting a duration of the exercise period;
  entering a description of an exercise performed during the exercise period; and
  entering an intensity of the exercise performed during the exercise period.

Clause 152. The method of clause 151, wherein the intensity of the exercise performed during the exercise period is entered by adjusting a slide bar to indicate an intensity from a range of low to high.

Clause 153. The method of clause 151, wherein entering the description of the exercise performed comprises typing a description of the exercise into a text field.

Clause 154. The method of clause 151, wherein entering the description of the exercise performed comprises selecting an exercise from a suggested list of exercises.

Clause 155. The method of clause 154, wherein the suggested list of exercises comprises a list of past exercises entered by a user.

Clause 156. The method of clause 154, wherein the suggested list of exercises comprises a list of five most recent exercises entered by a user.

Clause 157. A method of logging a mood, comprising the steps of:
setting a time and a date of a mood entry;
selecting a mood from a plurality of mood options; and
entering a description of a feeling associated with the time and the date of the mood entry.

Clause 158. The method of clause 157, wherein the plurality of mood options comprises a plurality of emojis depicting different expressions.

Clause 159. The method of clause 157, wherein entering the description of the feeling comprises typing a description of the feeling into a text field.

Clause 160. The method of clause 157, wherein entering the description of the feeling comprises selecting a feeling from a suggested list of feelings.

Clause 161. The method of clause 160, wherein the suggested list of feelings comprises a list of past feelings entered by a user.

Clause 162. The method of clause 161, wherein the suggested list of feelings comprises a list of five most recent feelings entered by a user.

Clause 163. A method of logging an energy level, comprising the steps of:
setting a time and date of an energy level entry;
entering an energy level; and
entering a description of a feeling associated with the time and date of the energy level entry.

Clause 164. The method of clause 163, wherein the energy level is entered by adjusting a slide bar to indicate an energy level from a range of low to medium to high.

Clause 165. The method of clause 163, wherein entering the description of the feeling comprises typing a description of the feeling into a text field.

Clause 166. The method of clause 163, wherein entering the description of the feeling comprises selecting a feeling from a suggested list of feelings.

Clause 167. The method of clause 166, wherein the suggested list of feelings comprises a list of past feelings entered by a user.

Clause 168. The method of clause 167, wherein the suggested list of feelings comprises a list of five most recent feelings entered by a user.

Clause 169. A method of logging an appetite level, comprising the steps of:
setting a time and date of an appetite level entry;
entering an appetite level; and
entering a description of a feeling associated with the time and date of the appetite level entry.

Clause 170. The method of clause 169, wherein the appetite level is entered by adjusting a slide bar to indicate a level from a range of low to medium to high.

Clause 171. The method of clause 169, wherein entering the description of the feeling comprises typing a description of the feeling into a text field.

Clause 172. The method of clause 169, wherein entering the description of the feeling comprises selecting a feeling from a suggested list of feelings.

Clause 173. The method of clause 172, wherein the suggested list of feelings comprises a list of past feelings entered by a user.

Clause 174. The method of clause 173, wherein the suggested list of feelings comprises a list of five most recent feelings entered by a user.

Clause 175. An apparatus for analyzing metrics relating to a subject, the apparatus comprising:
an input configured to receive measured ketone data;
a display configured to visually present information; and
one or more processors coupled with the input, the display, and a memory storing instructions that, when executed by the one or more processors, cause the apparatus to:
determine if a ketone level is above a threshold ketone concentration; and
output a notification in response to a determination that the ketone level is above the threshold ketone concentration.

Clause 176. The apparatus of clause 175, wherein the threshold ketone concentration is predetermined.

Clause 177. The apparatus of clause 175, wherein the threshold ketone concentration is set by the subject.

Clause 178. The apparatus of clause 175, wherein the threshold ketone concentration is about 0.5 mmol/L.

Clause 179. The apparatus of clause 175, wherein the notification in response to the determination that the ketone level is above the threshold ketone concentration comprises a tactile component.

Clause 180. The apparatus of clause 179, wherein the tactile component is a vibration.

Clause 181. The apparatus of clause 183, wherein the notification in response to the determination that the ketone level is above the threshold ketone concentration comprises a sound.

Clause 182. The apparatus of clause 175, wherein the notification in response to the determination that the ketone level is above the threshold ketone concentration comprises a message stating that a user has reached a state of ketosis.

Clause 183. The apparatus of clause 175, wherein the instructions further cause the apparatus to:
determine if a ketone level drops below the threshold ketone concentration after a determination that the ketone level was above the threshold ketone concentration; and
output a notification in response to a determination that the ketone level dropped below the threshold ketone concentration.

Clause 184. The apparatus of clause 183, wherein the notification in response to the determination that the ketone level dropped below the threshold ketone concentration comprises a tactile component.

Clause 185. The apparatus of clause 184, wherein the tactile component is a vibration.

Clause 186. The apparatus of clause 183, wherein the notification in response to the determination that the ketone level dropped below the threshold ketone concentration comprises a sound.

Clause 187. The apparatus of clause 183, wherein the notification in response to the determination that the ketone level dropped below the threshold ketone concentration comprises a message stating that a user has dropped out of ketosis.

I claim:
1. A system for monitoring metrics relating to a subject, the system comprising:
a sensor control device comprising a ketone sensor, at least a portion of which is configured to be in fluid contact with a bodily fluid of the subject;

a reader device, comprising:
wireless communication circuitry configured to receive measured ketone data continuously from the sensor control device;
a display configured to visually present information; and
one or more processors coupled with the wireless communication circuitry, the display, and a memory storing instructions that, when executed by the one or more processors, cause the one or more processors to:
display a graph comprising a ketone profile and a ketosis threshold, wherein the ketone profile displays the received measured ketone data for a time period;
display an indication of a concentration of ketone, wherein the indication is a numeric value when the concentration of ketone is at or above a low concentration threshold, and wherein the indication does not include the numeric value for the concentration of ketone if the concentration of ketone is below the low concentration threshold;
display an average of a ketone level for the time period; and
display a total amount of time in ketosis for the time period.

2. The system of claim 1, wherein the graph further comprises a target threshold.

3. The system of claim 2, wherein the instructions further cause the one or more processors to display a total amount of time above the target threshold for the time period.

4. The system of claim 1, wherein the concentration of ketone is a real time concentration of ketone.

5. The system of claim 1, wherein the instructions further cause the one or more processors to display a trend arrow related to the concentration of ketone.

6. The system of claim 1, wherein the instructions further cause the one or more processors to display a status of the ketone sensor, wherein the sensor control device is configured to transmit the measured ketone data to the reader device.

7. The system of claim 1, wherein the graph further comprises a shading in an area under the ketone profile.

8. The system of claim 7, wherein the shading is a gradient, and wherein the shading is less transparent closer to a curve of the ketone profile.

9. The system of claim 1, wherein the graph further comprises at least one icon on the ketone profile corresponding to a logged entry.

10. The system of claim 9, wherein the logged entry comprises a food and drink entry, a fasting entry, an exercise entry, a mood entry, an appetite entry, or an energy entry.

11. The system of claim 1, wherein the graph further comprises at least one fasting icon on the ketone profile corresponding to a logged fasting entry, wherein the logged fasting entry comprises a fasting time duration, a start time, and an end time, wherein the graph further comprises a shading in an area under the ketone profile from the start time to the end time of the logged fasting entry.

12. The system of claim 1, wherein the graph further comprises at least one exercise icon on the ketone profile corresponding to a logged exercise entry, wherein the logged exercise entry comprises an exercise time duration, a start time, and an end time, wherein the graph further comprises a shading in an area under the ketone profile from the start time to the end time of the logged exercise entry.

13. The system of claim 1, wherein the instructions further cause the one or more processors to display a pill corresponding to a plurality of logged entries that have corresponding logged times that occur within a predetermined time period.

14. The system of claim 13, wherein the pill comprises a number of entries in the plurality of logged entries.

15. The system of claim 13, wherein the instructions further cause the one or more processors to display a tooltip in response to selection of or pressure applied to the pill.

16. The system of claim 15, wherein the tooltip comprises a listing of the plurality of logged entries.

17. The system of claim 16, wherein the each of the logged entries of the plurality of logged entries comprise an icon, a logging time, and a brief description.

18. The system of claim 1, wherein the instructions further cause the one or more processors to display a flag in response to pressure applied to the display for a minimum period of time.

19. The system of claim 18, wherein the flag comprises the indication of the concentration of ketone at a first time, wherein the first time corresponds to a time on the graph at or near where the pressure was applied to the display.

20. The system of claim 19, wherein if the concentration is below a low concentration threshold, the indication of the concentration of ketone does not include a numeric value for the concentration of ketone.

21. The system of claim 19, wherein the indication of the concentration of ketone at the first time is a numeric value if the concentration at the first time is above the low concentration threshold.

22. The system of claim 1, wherein the indication is the numeric value if the concentration of ketone is between the low concentration threshold and a high concentration threshold, and wherein the indication does not include the numeric value if the concentration is above the high concentration threshold.

23. The system of claim 1, wherein, if the concentration is below the low concentration threshold, the indication is displayed as <the low concentration threshold.

24. The system of claim 22, wherein, if the concentration is above the high concentration threshold, the indication is displayed as >the high concentration threshold.

* * * * *